United States Patent
Trager et al.

(10) Patent No.: US 11,433,146 B2
(45) Date of Patent: Sep. 6, 2022

(54) FORMULATIONS FOR SMALL INTESTINAL DELIVERY OF RSV AND NOROVIRUS ANTIGENS

(71) Applicant: Vaxart, Inc., San Francisco, CA (US)

(72) Inventors: George Trager, Redwood City, CA (US); Sean Tucker, San Francisco, CA (US); Leesun Kim, Pacifica, CA (US); Ciaran Scallan, San Francisco, CA (US)

(73) Assignee: Vaxart, Inc., San Francisco, CA (US)

( * ) Notice: Subject to any disclaimer, the term of this patent is extended or adjusted under 35 U.S.C. 154(b) by 0 days.

(21) Appl. No.: 15/580,651

(22) PCT Filed: Jun. 8, 2016

(86) PCT No.: PCT/US2016/036461
§ 371 (c)(1),
(2) Date: Dec. 7, 2017

(87) PCT Pub. No.: WO2016/200951
PCT Pub. Date: Dec. 15, 2016

(65) Prior Publication Data
US 2018/0161458 A1    Jun. 14, 2018

Related U.S. Application Data

(60) Provisional application No. 62/175,081, filed on Jun. 12, 2015.

(51) Int. Cl.
*A61K 39/12* (2006.01)
*A61K 48/00* (2006.01)
(Continued)

(52) U.S. Cl.
CPC ........ *A61K 48/0058* (2013.01); *A61K 9/0053* (2013.01); *A61K 9/2009* (2013.01);
(Continued)

(58) Field of Classification Search
None
See application file for complete search history.

(56) References Cited

U.S. PATENT DOCUMENTS

| 4,152,413 A | 5/1979 | Goodnow | |
| 5,609,871 A * | 3/1997 | Michael | ............... A61K 9/5078 |
| | | | 424/184.1 |

(Continued)

FOREIGN PATENT DOCUMENTS

| CN | 104302278 A | 1/2015 |
| EP | 1041149 A2 | 10/2000 |

(Continued)

OTHER PUBLICATIONS

Mercier et al., "Oral Immunization of Rhesus Macaques with Adenoviral HIV Vaccines Using Enteric-coated Capsules," Vaccine 25(52): 8687-8701 (Year: 2007).*

(Continued)

*Primary Examiner* — M Franco G Salvoza
(74) *Attorney, Agent, or Firm* — Kilpatrick Townsend & Stockton LLP

(57) ABSTRACT

Provided herein are compositions and methods for generating an immunogenic response in humans. Further provided are methods for designing such compositions, e.g., for vaccines.

16 Claims, 37 Drawing Sheets

Specification includes a Sequence Listing.

(51) Int. Cl.
  *A61K 9/28*  (2006.01)
  *A61K 9/20*  (2006.01)
  *A61K 9/00*  (2006.01)
(52) U.S. Cl.
  CPC .......... *A61K 9/2054* (2013.01); *A61K 9/2059* (2013.01); *A61K 9/282* (2013.01); *A61K 9/2813* (2013.01); *A61K 9/2846* (2013.01); *A61K 39/12* (2013.01); *C12N 2710/10341* (2013.01); *C12N 2710/10343* (2013.01); *C12N 2760/18534* (2013.01); *C12N 2770/16034* (2013.01)

(56) References Cited

U.S. PATENT DOCUMENTS

| | | | |
|---|---|---|---|
| 5,762,904 A | 6/1998 | Okada et al. | |
| 6,174,529 B1 | 1/2001 | Michael et al. | |
| 6,224,911 B1 | 5/2001 | Chowhan et al. | |
| 6,228,396 B1 | 5/2001 | Watts | |
| 6,458,389 B1 | 10/2002 | Debregeas et al. | |
| 2001/0026800 A1 | 10/2001 | Michael | |
| 2001/0043949 A1 | 11/2001 | Delgado | |
| 2003/0133950 A1 | 7/2003 | Michael et al. | |
| 2006/0134216 A1 | 6/2006 | Farrell et al. | |
| 2007/0269410 A1* | 11/2007 | Tucker | A61P 31/22 424/93.2 |
| 2010/0111989 A1 | 5/2010 | Grundwald et al. | |
| 2010/0221329 A1 | 9/2010 | Shailubhai et al. | |
| 2011/0081375 A1 | 4/2011 | Tucker | |
| 2012/0244185 A1 | 9/2012 | Tucker et al. | |
| 2012/0276167 A1 | 11/2012 | Lam et al. | |
| 2013/0171185 A1* | 7/2013 | Settembre | C12N 7/00 424/192.1 |
| 2013/0195800 A1* | 8/2013 | Roeth | C07K 14/5434 424/93.2 |
| 2013/0273154 A1 | 10/2013 | Fayad et al. | |
| 2013/0337055 A1 | 12/2013 | Schentag et al. | |
| 2014/0199389 A1 | 7/2014 | Sparling, II | |
| 2015/0071994 A1 | 3/2015 | Schentag et al. | |
| 2017/0224805 A1 | 8/2017 | Tucker et al. | |

FOREIGN PATENT DOCUMENTS

| | | |
|---|---|---|
| JP | S55-47617 A | 4/1980 |
| JP | H9-510478 A | 10/1997 |
| JP | 2002-534485 A | 10/2002 |
| JP | 2003-517440 A | 5/2003 |
| JP | 2007-509903 A | 4/2007 |
| JP | 2008-523096 A | 7/2008 |
| JP | 2009-298707 A | 12/2009 |
| JP | 2011-526888 A | 10/2011 |
| JP | 2015-512400 A | 4/2015 |
| WO | 98/18453 A1 | 5/1998 |
| WO | 99/45904 A1 | 9/1999 |
| WO | 00/12065 A1 | 3/2000 |
| WO | 2011/026111 A1 | 3/2011 |
| WO | 2013/148258 A1 | 10/2013 |
| WO | 2015/127278 A1 | 8/2015 |

OTHER PUBLICATIONS

International Search Report and Written Opinion as received in International Patent Application No. PCT/US16/36461, filed Jun. 8, 2016. Received Sep. 2, 2016. 13 pages.
International Preliminary Report on Patentability received in International Patent Application No. PCT/US2016/036461, dated Dec. 21, 2017. 6 pages.
Meeus, L. "Direct Compression Versus Granulation." *Pharmaceutical Technology Europe,* vol. 23, Issue 3. Published Mar. 7, 2011. 3 pages.
Scallan, C. et al. "An Adenovirus-Based Vaccine with a Double-Stranded RNA Adjuvant Protects Mice and Ferrets against H5N1 Avian Influenza in Oral Delivery Models." *Clinical and Vaccine Immunology,* vol. 20, Issue 1. Published Jan. 2013. pp. 85-94.
Eudragit. Evonik Industries. Published Dec. 1, 2015. Retrieved Jul. 13, 2016. Retrieved from the Internet: URL<http://eudragit.evonik.com/sites/lists/HN/Documents/evonik-brochure-eudragit-EN.pdf>. 16 pages.
Extended European Search Report received in European Patent Application No. 15752216.0, dated Sep. 8, 2017. 9 pages.
First Office Action received in Eurasian Patent Application No. 201691458/28, dated Dec. 8, 2017. English translation provided. 7 Pages.
Huyghebaert, N. et al. *In Vitro Evaluation of Coating Polymers for Enteric Coating and Human Ileal Targeting.* International Journal of Pharmaceutics, vol. 298, Issue 1. Published Jul. 2005. pp. 26-37.
International Application No. PCT/US2015/016921, International Preliminary Report on Patentability dated Sep. 1, 2016, 6 pages.
International Search Report of the International Searching Authority for International Application No. PCT/US15/16921 dated May 15, 2015, 4 pages.
Kim, L. et al. *Systemic and Mucosal Immune Responses Following Oral Adenoviral Delivery of Influenza Vaccine to the Human Intestine by Radio Controlled Capsule.* Scientific Reports, Nature, 6:37295. Published Nov. 24, 2016. 11 pages.
Thakral, S. et al. *Eudragit: A Technology Evaluation.* Abstract only. Expert Opinion on Drug Delivery, vol. 10, Issue 1. Published Jan. 2013. 1 page.
Wang Lishan, Written Opinion received in Singapore Application No. 11201606814R, Filing Date Feb. 20, 2015. Received Aug. 18, 2017. 10 pages.
Written Opinion of the International Searching Authority for International Application No. PCT/US15/16921 dated May 15, 2015, 4 pages.
Office Action received in Chinese Patent Application No. 201580015312.2, dated Apr. 2, 2019. 12 pages.
Hao, S. *Preparation Of Eudragit L 100-55 Enteric Nanoparticles By A Novel Emulsion Diffusion Method.* Colloids and Surfaces B: Biointerfaces, vol. 108. Published Mar. 14, 2013. 7 pages.
Petereit, H. *EUDRAGIT Application Guidelines.* TalkeTPE.com. Published Aug. 31, 2009. 199 pages.
Advisory Action received in U.S. Appl. No. 15/120,069, dated Feb. 7, 2019. 7 pages.
Final Office Action received in U.S. Appl. No. 15/120,069, dated Oct. 18, 2018. 27 pages.
Non-Final Office Action received in U.S. Appl. No. 15/120,069, dated Mar. 29, 2018. 14 pages.
Restriction Requirement received in U.S. Appl. No. 15/120,069, dated Jan. 4, 2018. 10 pages.
Non-Final Office Action received in U.S. Appl. No. 15/120,069, dated Feb. 25, 2019. 18 pages.
Extended European Search Report Received in EP Application No. 16808196.6, received Jan. 22, 2019. 10 pages.
Sonje, A. et al. *Comprehensive Review of Eudragit Polymers.* International Research Journal of Pharmacy, vol. 4, No. 5. Published Nov. 2013. 4 pages.
Tacket, C. et al. *Humoral, Mucosal, and Cellular Immune Response to Oral Norwalk Virus-Like Particles in Volunteers.* Clinical Immunology, vol. 108. Published Apr. 2003. 7 pages.
Kohlmann et al., "Protective Efficacy and Immunogenicity of an Adenoviral Vector Vaccine Encoding the Codon-Optimized F Protein of Respiratory Syncytial Virus", Journal of Virology, 2009, vol. 83, No. 23, pp. 12601-12610.
Ma etal., "Vesicular Stomatitis Virus as a Vector To Deliver Virus-Like Particles of Human Norovirus; a New Vaccine Candidate against an Important Noncultivable Virus", Journal of Virology, 2011, vol. 85, No. 6, pp. 2942-2952.
U.S. Appl. No. 15/120,069 , "Final Office Action", dated Sep. 6, 2019, 16 pages.
U.S. Appl. No. 15/120,069 , "Non-Final Office Action", dated May 14, 2020, 16 pages.
Application EP 0 706 792 A1, "Method of Potentiating an Immune Response and Compositions Therefor", Apr. 17, 1996, 39 pages.
U.S. Appl. No. 15/120,069, filed Aug. 15, 2016, "Final Office Action", dated Nov. 25, 2020, 21 pages.

(56) References Cited

OTHER PUBLICATIONS

Application EP 15 752 216.0, "Communication Pursuant to Article 94(3) EPC", dated Oct. 21, 2020, 7 pages.
Application EP 20195995.4, "Communication—Extended Search Report", dated Feb. 16, 2021, 9 pages.
Evans et al, "Measurement of Gastrointestinal PH Profiles in Normal Ambulant Human Subjects", Gut microbiota, Aug. 1, 1988, pp. 1035-1041, vol. 29, No. 8.
Hardy et al., "Evaluation of an Enteric-Coated Delayed-Release 5-Aminosalicylic Acid Tablet in Patients With Inflammatory Bowel Disease", Aliment. Pharmacol. Therap., Aug. 1987, pp. 273-280, vol. 1, Issue 4.
Mutwiri et al., "Ileal and Jejunal Peyer's Patches Play Distinct Roles in Mucosal Immunity of Sheep", Immunology, Jul. 1999, pp. 455-461, 97 (3).
"Polymethacrylates—Extract of the Handbook of Pharmaceutical Excipients", Royal Pharmaceutical Society of Great Britain, Pharmaceutical Press, Edition 5, 2006, pp. 553-560.
"Talc—Extract of the Handbook of Pharmaceutical Excipients", Royal Pharmaceutical Society of Great Britain, Pharmaceutical Press, 2006, pp. 767-769.
"Triethyl Citrate—Extract of the Handbook of Pharmaceutical Excipients", Royal Pharmaceutical Society of Great Britain, Pharmaceutical Press, 2006, pp. 796-797.
EP16808196.6 , "Notice of Opposition", Jun. 30, 2021, 26 pages.
U.S. Appl. No. 15/120,069 , "Non-Final Office Action", dated Apr. 29, 2021, 27 pages.
Barros et al., "A Laminated Polymer Film Formulation for Enteric Delivery of Live Vaccine and Probiotic Bacteria", Journal of Pharmaceutical Sciences, vol. 103, No. 7, 2014, pp. 2022-2032.
Dvorackova et al., "Coated Capsules for Drug Targeting to Proximal and Distal Part of Human Intestine", Acta Poloniae Pharmaceutica—Drug Research, vol. 67, No. 2, 2010, pp. 191-199.
Khan et al., "A Ph-dependent Colon Targeted Oral Drug Delivery System Using Methacrylic Acid Copolymers. I. Manipulation of Drug Release Using Eudragit L 100-55 and Eudragit S100 Combinations", Journal of Controlled Release, vol. 58, 1999, pp. 215-222.
"Peyer's Patch", Wikipedia, Nov. 11, 2021, 4 pages.
U.S. Appl. No. 15/120,069 , Final Office Action, dated Dec. 29, 2021, 31 pages.
Foreman et al., "Adenovirus-Mediated Transduction of Intestinal Cells in Vivo", Human Gene Therapy, vol. 9, No. 9, Jun. 10, 1998, pp. 1313-1321.
Evans et al., "Measurement of Gastrointestinal pH Profiles in Normal Ambulant Human Subjects", Gut, 1988, pp. 1035-1041 (29).
Opposition to European Patent No. 3307239 (EP Application No. 16808196.6), "Opponent Further Submissions", Mar. 10, 2022, 6 pages.
EP16808196.6, "Summons to Attend Oral Proceedings", dated Apr. 13, 2022, 17 pages.

* cited by examiner

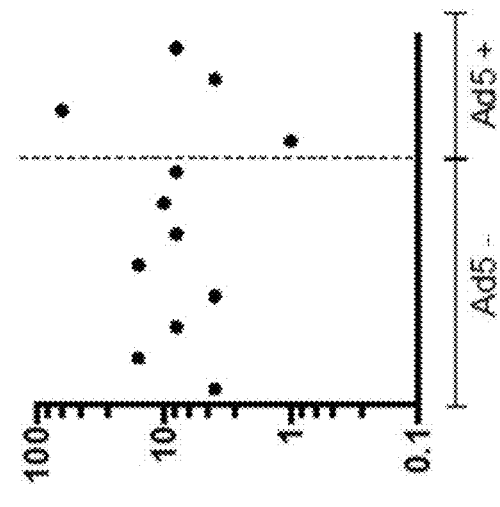
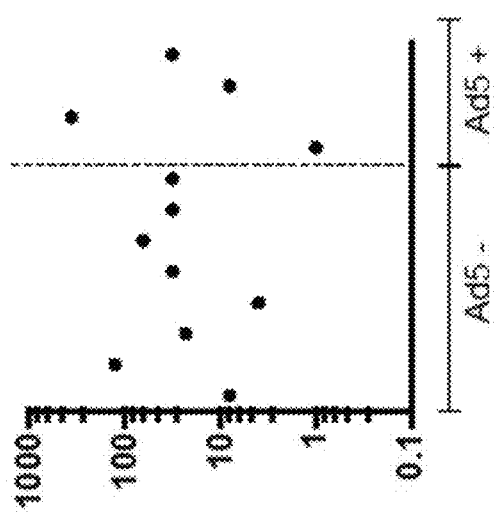
FIG. 21A
FIG. 21B

FORMULATIONS FOR SMALL INTESTINAL DELIVERY OF RSV AND NOROVIRUS ANTIGENS

CROSS-REFERENCES TO RELATED APPLICATIONS

The present application claims priority and is a 371 application of PCT Application No. PCT/US16/36461, filed Jun. 8, 2016, which claims priority to U.S. Provisional Application No. 62/175,081, filed Jun. 12, 2015, the disclosure of which is incorporated herein in its entirety.

REFERENCE TO SUBMISSION OF A SEQUENCE LISTING AS A TEXT FILE

The Sequence Listing written in file SubstitureSequencListing-1068823.txt, created on Oct. 12, 2018, 62,588 bytes, machine format IBM-PC, MS-Windows operating system, is hereby incorporated by reference.

BACKGROUND OF THE INVENTION

Vaccines are an important means for preventing and/or treating a number of diseases and disorders (e.g., viral infection, bacterial infection, and cancer). Vaccinization is typically carried out using injection, which reduces participation due to inconvenience of traveling to a vaccination site and aversion to injections. Furthermore, injection of vaccines requires use of sterile kit, such as syringes and needles, and a skilled practitioner to administer.

For the influenza vaccine, large-scale yearly campaigns are conducted to collect enough fertilized eggs to harvest and process sufficient virus to meet the needs of the market. Cell culture or plant derived hemagglutinin (HA) may reduce the burden of egg acquisition and processing, but these approaches still require expensive sterile fill and finish to produce individual syringe needles, that need to be disposed of as a biohazard. During a pandemic, schools can be closed and social distancing mandated, yet mass influenza immunization typically requires lining up subjects at health clinics for injections. Oral vaccines, for influenza or other pathogens, could be sent through the mail thus avoiding most human to human contact. Further, tableting is a rapid, sanitary process that does not require the expensive sterile fill and finishing process that injected vaccines require.

Vaccines that can be delivered in a non-parenteral manner, e.g., orally or mucosally, are described in U.S. Pat. No. 8,222,224.

BRIEF SUMMARY OF THE INVENTION

Provided herein are methods and compostions for more effective vaccination of a subject (human or non-human) involving delivery of an immunogenic biological agent specifically to the ileum of the subject. The present disclosure thus provides more efficient and effective vaccines, and demonstrates their effectiveness in humans.

Provided herein are immunogenic compositions for eliciting an immune response in a subject comprising: an immunogenic biological agent encompassed by a delivery agent that directs delivery of the immunogenic biological agent to the ileum of the subject. In some embodiments, the subject is a human. In some embodiments, the subject is a non-human animal, e.g., primate, mouse, rat, rabbit, horse, dog, cat, or poultry. In some embodiments, the immunogenic biological agent is selected from an immunogenic polypeptide (e.g., virus like particle, glycoprotein, phosphoprotein), carbohydrate, and lipid. In some embodiments, the immunologenic biological agent is an adenoviral vector encoding the viral protein 1 of norovirus or the fusion protein (F) of Respiratory syncytial virus (RSV). In some embodiments, the viral protein 1 of norovirus is SEQ ID NO: 2 or SEQ ID NO: 4. In some embodiments, the fusion protein (F) of RSV is SEQ ID NO: 6. In some embodiments, the adenoviral vector comprises a nucleotide sequence of SEQ ID NO: 7.

In some embodiments, the immunogenic biological agent is an expression vector encoding an immunogenic polypeptide. In some embodiments, the expression vector is a viral vector (e.g., adenoviral, AAV, retroviral, or lentiviral). In some embodiments, the viral vector is attenuated or replication incompetent. In some embodiments, the expression vector comprises a promoter (e.g., CMV, SV40 early or late, β-actin, etc.) operably linked to the sequence encoding the immunogenic polypeptide. In some embodiments, the expression vector further encodes double stranded (dsRNA). In some embodiments, the dsRNA encoding sequence is operably linked to a promoter, e.g., either the same promoter (using an Internal Ribosomal Entry Site (IRES)) or a different promoter as the promoter operably linked to the immunogenic polypeptide encoding sequence.

In some embodiments, the immunogenic composition further comprises at least one adjuvant, e.g., a TLR3 agonist. In some embodiments, the TLR3 agonist is dsRNA or a dsRNA mimetic.

In some embodiments, at least 50% of the immunogenic biological agent is delivered (released) in the ileum, e.g., at least 60%, 70%, 75%, 80%, 90%, 95%, or more of the immunogenic biological agent present in the administered composition. In some embodiments, the enteric coating or matrix begins to dissolve before the immunogenic composition reaches the ileum, but retains at least 50% of the immunogenic biological agent until the immunogenic composition reaches the ileum. In some embodiments, the enteric coating retains the immunogenic biological agent through the stomach, duodenum, and jejunum, but releases the immunogenic biological agent in the ileum.

In some embodiments the immunogenic biological agent is covered by an enteric coating. In some embodiments, the enteric coating disintegrates at pH≥5, e.g., 5.2, 5.5, 5.7, 5.8, 5.9, 6, 6.1, 6.2, 6.3, 6.4, 6.5, 6.6, 6.7, 6.8, 7.0, 5.5-6.8, 5.8-6.8, etc. In some embodiments, the enteric coating is selected from the group consisting of methacrylic acid-ethyl acrylate copolymer (e.g., 1:1), type A; methacrylic acid copolymer, type C; a mixture of methacrylic copolymer types A and C; and Time Clock®. In some embodiments, the enteric coating does not include cellulose acetate phthalate (CAP). In some embodiments, the enteric coating is of a thickness that results in release of the immunogenic biological agent in the ileum. In some embodiments, the enteric coating is methacrylic acid copolymer-based with a coverage of 5.5-10 milligram per square centimeter. In some embodiments, the delivery agent is a radio-controlled capsule.

In some embodiments, the enteric coating comprises poly(methacrylic acid-co-methyl methacrylate) 1:1. In some embodiments, the enteric coating comprises Eudragit® L 100. In some embodiments, the enteric coating comprises Eudragit® L-100, triethyl citrate, and talc, e.g., 1, 2, 3, 4 or 1-4 parts Eudragit® L-100, 1-2 parts triethyl citrate, and 1-2 parts talc. In some embodiments, enteric coating comprises a mixture of poly(methacrylic acid-co-methyl methacrylate) 1:1 and poly(methacrylic acid-co-ethyl acrylate) 1:1. In some embodiments, the ratio of poly(methacrylic acid-co-methyl methacrylate) 1:1 to poly(methacrylic acid-co-ethyl acrylate) 1:1 is 1:4 to 4:1, e.g., 1:3, 1:2, 1:1, 2:1, 3:1. In some embodiments, the enteric coating comprises a mixture of Eudragit® L-100 and Eudragit®L100-55. In some embodiments, the enteric coating comprises Eudragit® L-100 and Eudragit®L100-55, triethyl citrate, and talc, e.g., 1-4 parts Eudragit® L-100 and Eudragit®L100-55, 1-2 parts triethyl citrate, and 1-2 parts talc. In some embodiments, the enteric coating comprises poly(methacrylic acid-co-methyl methacrylate) 1:1 and poly(methacylic acid-co-methyl methacrylate) 1:2. In some embodiments, the ratio of poly(methacylic acid-co-methyl methacrylate) 1:1 to poly(methacrylic acid-co-methyl acrylate) 1:2 is 1:2 to 2:1. In some embodiments, the enteric coating comprises a mixture of Eudragit® L-100 and Eudragit®S100. In some embodiments, the enteric coating comprises Eudragit® L-100 and Eudragit®S100, triethyl citrate, and talc, e.g., 1-4 parts Eudragit® L-100 and Eudragit®S100, 1-2 parts triethyl citrate, and 1-2 parts talc. In some embodiments, the enteric coating comprises a mixture of poly(methacrylic acid-co-methyl methacrylate) 1:2 and poly(methacrylic acid-co-ethyl acrylate) 1:1. In some embodiments, the ratio of poly(methacrylic acid-co-methyl methacrylate) 1:2 and poly(methacrylic acid-co-ethyl acrylate) 1:1 is 1:4 to 4:1, e.g., 1:3, 1:2, 1:1, 2:1, or 3:1. In some embodiments, the enteric coating comprises a mixture of Eudragit® L-100-55 and Eudragit®S100. In some embodiments, the enteric coating comprises Eudragit® L-100-55 and Eudragit®S100, triethyl citrate, and talc, e.g., 1-4 parts Eudragit® L-100-55 and Eudragit®S100, 1-2 parts triethyl citrate, and 1-2 parts talc.

In some embodiments, the immunogenic composition is in the form of a tablet or capsule, e.g., in the form of a compressed tablet covered by enteric coating. In some embodiments, the immunogenic composition is encapsulated in a polymeric capsule comprising gelatin, hydroxypropylmethylcellulose, starch, or pullulan. In some embodiments, the immunogenic composition is in the form of microparticles less than 2 mm in diameter, e.g., each microparticle covered with enteric coating as described herein:

Further provided is a method of delivering an immunogenic composition to the ileum of subject comprising orally administering the immunogenic composition as described above (i.e., an immunogenic biological agent encompassed by a delivery agent that directs delivery of the immunogenic biological agent to the ileum, optionally including an adjuvant) to the subject. In some embodiments, the subject is a human. In some embodiments, the subject is a non-human animal. In some embodiments, the method results in an immune response in the subject that is at least 10% higher, e.g., at least 20%, 30%, 40%, 50%, 60%, 75%, 80%, 100% or more, than the immune response in a subject (either the same subject at a different time, or a different subject) receiving the same immunogenic composition not directed to the ileum. In some embodiments, the immune response in the subject is at least 1.5-fold higher (e.g., 2-fold, 2.5-fold, 5-fold, or more) than the immune response in a subject (either the same subject at a different time, or a different subject) receiving the same immunogenic composition not directed to the ileum. In some embodiments, the immune response is an increase in antibodies specific for the immunogenic biological agent. In some embodiments, the immune response is a cellular immune response, e.g., an increase in cytokines such as IFN-γ. In some embodiments, the immune response is immunization (e.g., the subject is resistant to infection by the virus, bacteria, etc. from which the immunogenic biological agent was derived).

Further provided are methods of eliciting an increased immune response in a subject comprising orally administering the immunogenic composition as described above (i.e., an immunogenic biological agent encompassed by a delivery agent that directs delivery of the immunogenic biological agent to the ileum, optionally including an adjuvant) to the subject, e.g., human subject. In some embodiments, the immune response is increased by at least 10%, e.g., at least 20%, 30%, 40%, 50%, 60%, 75%, 80%, 100% or more, compared to the immune response in a subject (either the same subject at a different time, or a different subject) receiving the same immunogenic composition not directed to the ileum. In some embodiments, the immune response in the subject is increased at least 1.5-fold (e.g., 2-fold, 2.5-fold, 5-fold, or more) compared the immune response in a subject (either the same subject at a different time, or a different subject) receiving the same immunogenic composition not directed to the ileum. In some embodiments, the immune response is an increase in antibodies specific for the immunogenic biological agent. In some embodiments, the immune response is a cellular immune response, e.g., an increase in cytokines such as IFN-γ. In some embodiments, the immune response is immunization (e.g., the subject is resistant to infection by the virus, bacteria, etc. from which the immunogenic biological agent was derived).

BRIEF DESCRIPTION OF THE DRAWINGS

FIG. 4A. Tablet in the stomach with the arrow pointing toward the tablet. FIG. 4B. One hour later, the tablet can be seen in the intestine, the white spot to the left of the spinal column with an arrow point toward it. It dissolved in the intestine within the next two hours, and cannot be seen.

FIG. 7A. Hemagglutination Inhibition ("HAI") antibody titers pre and post immunization (days 0 and 28 respectively) are shown for individual subjects. FIG. 7B HAI Geometric Mean Titers (GMT) vs Time. HAI titers were measured at 0, 1, and 6 months post immunization to evaluate the durability of the antibody response. FIG. 7C. MN titers, pre and post immunization are shown for individual subjects. FIG. 7D. ASC responses following immunization. The numbers of IgG and IgA ASCs are reported (per $10^6$ PMBCs) 7 days after immunization.

FIG. 20A shows HAI antibody titers pre and post immunization (days 0 and 28 respective) are shown for individual subjects. FIG. 20B shows HAI GMT v. time. HAI titers were measured at 0, 1, and 6 months post immunization to evaluate the durability of the antivody response. FIG. 20C shows MN titers pre and post immunization for individual subjects. FIG. 20D shows ASC response following immunization. The numbers of IgG and IgA ASCs are reported (per 1e6 PMBCs) 7 days after immunization.

FIGS. 21A-21B. Anti-Ad5 immunity and effects on neutralizing antibody responses. FIG. 21A shows Fold change in MN versus starting anti-Ad5 titer for vaccine treated subjects. Subjects were not pre-screened for anti-Ad5 titers, but retrospectively measured. FIG. 21B shows fold change in HAI responses that were plotted for etiher M5 titer positive or negative, analogous as performed in FIG. 2. No trend was observed for Ad5 starting titers on the ability to elicit a neutralizing antibody response (by MN or HAI) to influenza virus.

FIG. 23A shows female cotton rats were immunized on week 0 and 4, and antibody titers against RSV-f were measured on week 8. VXA-RSV-f immunization was significantly better than using RSV2 virus or FI-RSV for inducing IgG ELISA liters to RSV. (p<0.0022 by Mann-Whitney) FIG. 23B shows palivizumab competitive ELISA titers were evaluated using pooled serum samples from each of the previously described groups. FI-RSV vaccine was not able to induce epitope specific antibodies that compete for the binding of palivizumab, but the VXA-RSV-f vaccine and RSV2 treated groups were able to induce these titers. FIG. 23C shows the VXA-RSV-f vaccine induced neutralizing antibody responses to RSV following immunization of cotton rats. VXA-RSV-f and RSV2 groups were superior to the FI-RSV; and the no vaccine controls (no infection and buffer groups) at inducing neutralizing titers against RSV. N=6 per group, except the "no infection" control (N=3).

In FIG. 24A, female cotton rats were immunized with VXA-RSV-f on week 0.0 and 4, and the total IgG antibody ELISA titers were measured on weeks 4 and 8. Dose dependent antibody responses were observed with $1\times10^9$ and $1\times10^{10}$ trending better than the $1\times10^8$ IU dose group. In FIG. 24B, Palivizumab competitive ELISA titers were evaluated for the same groups as described before, but at week 8. Higher vaccine doses trended with higher Palivizumab competitive antibody titers, but the results were not significantly different. FIG. 24C shows oral immunization of VXA-RSV-f also induced dose dependent neutralizing antibody titers to RSV, with the 1×1010 group preforming significantly better than the 1×108 group (p=0.018 by Mann-Whitney). N=8 per oral group, N=6 for buffer control group.

FIG. 25A shows animals immunized with VXA-RSV-f before RSV challenge were completely protected against RSV replication in lung and nasal samples. Animals immunized with either buffer, adjuvant alone, or FI-RSV were not protected. Two different doses of vaccine were given for the i.n. treated animals ($1\times10^8$=low). Nom, except the no infection control animals (N=3). In FIG. 25B, inflammation in the lungs was scored by immunohistology. The vaccine groups (VXA-RSV-f and RSV2) did not cause adaptive immune enhanced inflammation (PB, PA, A, IP) as did the FI-RSV group. In FIG. 25C, cytokine abundance levels were measured by qRT-PCR. Only the FI-RSV immunized group had substantial increases in the relative abundance of IL-4 and IL-13, the Th2 cytokines measured.

In FIG. 26A, animals immunized orally show dose dependent immune responses to RSV infection, with the highest dose leading to complete protection in the lungs and almost complete protection in the nose. In contrast, there was no protection in the buffer control group. In FIG. 26B, inflammation was compared between vaccine doses and the buffer control group. In FIG. 26C, cytokine abundance levels were measured by qRT-PCR. No group had substantial increases in the relative abundance of either IL-4 or IL-13, the Th2 cytokines measured. (N=8 with the exception of buffer control N=6).

DETAILED DESCRIPTION OF THE INVENTION

Figure 1:
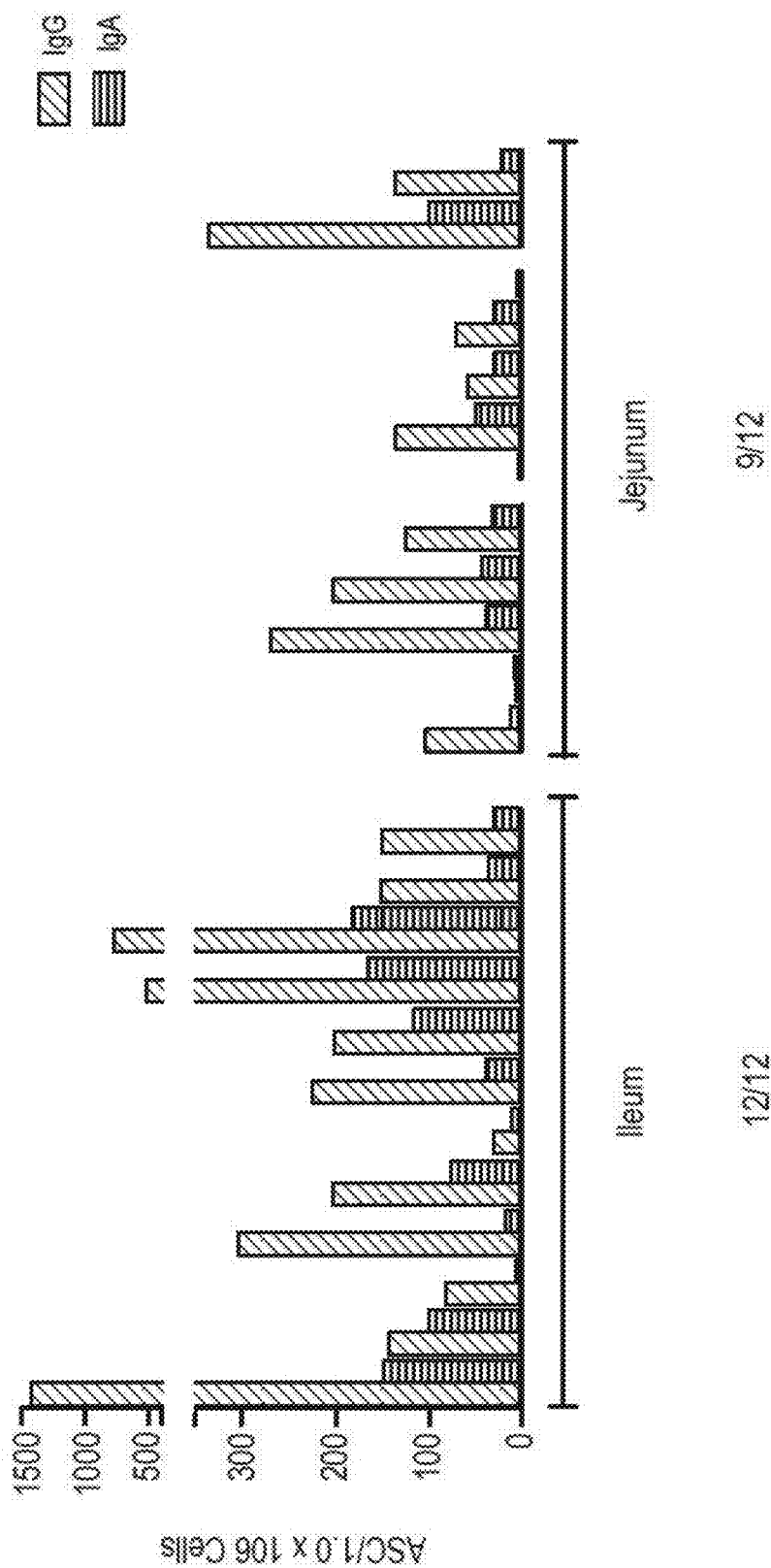
FIG. 1. Antibody Secreting Cells (ASCs) specific for HA were measured in the peripheral blood 7 days after subjects were given a radio-controlled capsule containing rAd-HA-dsRNA. Subjects were randomized to have the vaccine released in either the ileum or jejunum. (N=12 per group). Results show, that 12 of 12 subjects with vaccine delivered to the ileum were able to generate antibody secreting B cells that recognize HA, whereas only 9 of 12 subjects given the vaccine to the jejunum were able to generate antigen specific B cells. The average number of IgA and IgG ASCs was significantly higher for the ileum than the jejunum.

The inventors have discovered that delivery of an immunogenic biological agent to a particular part of the small intestine, i.e., the ileum, results in a much greater therapeutic response than when the agent is not targeted, or is targeted to a different site. This allows for design of more effective vaccines, reduced costs for materials, and reduced side effects for the recipient.

I. DEFINITIONS

The term "immunogenic" refers to the ability of an agent to give rise to an immune response in a host, either humoral or cell-mediated. Immunogenic agents are typically "foreign" to the host, e.g., from a different species, or from a bacteria, virus, or fungus. A non-foreign agent can be immunogenic, e.g., in the case of an autoimmune response. Certain cancer cell-specific agents can be exploited as immunogenic agents, allowing the host's immune system to attack the cancer.

The term "biological agent" refers to a nucleic acid, polypeptide, glycoprotein, carbohydrate, lipid, or modified form thereof (e.g. methylated, glycosylated, detestably labeled). Biological agents are distinguished from small molecule drugs in that they can be created by biological processes (including recombinant techniques) instead of chemical synthesis. Biological agents can, however, be chemically modified or include non-natural nucleotides or amino acids. Biological agents can also be non-naturally occurring, e.g., recombinant or chimeric entities.

As used herein, an "immunogenic biological agent" refers to an agent that acts directly as an antigen (e.g., is recognized by a T cell receptor or antibody), or an agent that, once expressed in a cell, acts as an antigen. For example, an immunogenic biological agent can include an expression vector encoding an immunogenic polypeptide.

The term "antigen" refers to a polypeptide, glycoprotein, lipoprotein, lipid, carbohydrate, or other agent that is bound (e.g., recognized as "foreign") by a T cell receptor and/or antibody. Antigens are commonly derived from bacterial, viral, or fungal sources. The term "derived from" indicates that the antigen is essentially as it exists in its natural antigenic context, or that it has been modified to be expressed under certain conditions, to include only the most immunogenic portion, or to remove other potentially harmful associated components, etc.

An "immunogenically effective dose or amount" of a composition as described herein is an amount that elicits or modulates an immune response specific for an antigen selected for vaccination. Immune responses include humoral immune responses and cell-mediated immune responses. An immunogenic composition can be used therapeutically or prophylactically to treat or prevent disease at any stage.

"Humoral immune responses" are mediated by cell free components of the blood, e.g., plasma or serum; transfer of the serum or plasma from one individual to another transfers humoral immunity. Humoral immune responses are typically B cell-mediated, e.g., antibody production.

"Cell mediated immune responses" are mediated by antigen specific lymphocytes; transfer of the antigen specific lymphocytes from one individual to another transfers immunity. Cell-mediated immune responses are mediated at least in part by T cells, and can be detected, e.g., by detecting T cell-specific cytokines or increase in T cell proliferation.

The "ileum" is the longest of the three segments that form the small intestine, along with the duodenum and jejunum. It is makes up the terminal portion, between the jejunum and cecum.

An enteric coating is a barrier applied to oral medications that prevents the therapeutic agent inside from being digested in the low pH environment of the stomach and duodenum (~pH 3).

A delivery agent, such as an enteric coating, matrix, or capsule, is said to retain an encompassed or embedded therapeutic agent when at least 60%, e.g., at least about 70%, 75%, 80%, 85%, 90%, 95%, or 100% of the original administered amount of therapeutic agent remains encompassed or embedded within the agent. The delivery agent, e.g., enteric coating or matrix, is typically designed to disintegrate under certain conditions and release the therapeutic agent. Disintegration can be gradual, e.g., in the case of a thicker or more chemically complex coating. The enteric coating is said to "disintegrate" once the coating thickness is reduced at least 10%, e.g., at least 25%, 50%, or 75% compared to the original administered thickness. Disintegration is not an absolute term, as it can occur over a different time course depending on conditions. For example, a coating that is designed to disintegrate in 5 minutes at pH 6.5 may disintegrate, albeit slowly, at pH 6 (e.g., in 1 hour). Disintegration does not necessarily indicate that the encompassed or embedded therapeutic agent is released. The therapeutic agent can, however, begin to be released before the enteric coating or matrix is entirely disintegrated.

The term "chimeric" or "recombinant" as used herein with reference, e.g., to a nucleic acid, protein, or vector, indicates that the nucleic acid, protein or vector, has been modified by, the introduction of a heterologous nucleic acid or protein or the alteration of a native nucleic acid or protein. Thus, for example, chimeric and recombinant vectors include nucleic acid sequences that are not found within the native (non-chimeric or non-recombinant) form of the vector. A chimeric viral expression vector refers to a viral expression vector comprising a nucleic acid sequence encoding a heterologous (e.g., immunogenic) polypeptide.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter. Viral expression vectors are typically rendered replication incompetent or attenuated. A virally-derived vector can include the components of the expression vector required for expression of a desired sequence, but omit those involved in, e.g., replication or other pathogenic effects.

The terms "promoter" and "expression control sequence" are used herein to refer to a nucleic acid control sequence that directs transcription of a nucleic acid. Promoter sequences are typically near the start site of transcription, such as a TATA element in the case of a polymerase II type promoter. A promoter can also include distal enhancer or repressor elements, which can be located as much as several thousand base pairs from the start site of transcription. Promoters include constitutive and inducible promoters. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, heterologous portions of a protein indicates that the protein comprises two or more subsequences that are not found in the same relationship to each other in nature (e.g., a fusion protein). A heterologous nucleic acid or protein is one that is not found in a particular environment in nature, e.g., a heterologous mouse protein in a human cell.

The terms "nucleic acid" and "polynucleotide" are used interchangeably herein to refer to polymers of deoxyribonucleotides or ribonucleotides in either single- or double-stranded form. The terms encompass genes, cDNA, RNA, and oligonucleotides (short polynucleotides). The terms encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The term "nucleotide" typically refers to a nucleic acid monomer.

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al, J. Biol. Chem. 260:2605-2608 (1985); Rossolini et al., Mol. Cell. Probes 8:91-98 (1994)).

A "therapeutic dose" or "therapeutically effective amount" or "effective amount" of a composition as described herein is an amount that prevents, alleviates, abates, or reduces the severity of symptoms of diseases and disorders associated with the source of the antigen selected for vaccination (e.g., a virus, bacteria, a parasite, or a cancer).

The term "antibody" refers to a polypeptide encoded by an immunoglobulin gene or fragments thereof that specifically bind and recognizes an antigen. Immunoglobulin sequences include the kappa, lambda, alpha, gamma, delta, epsilon, and mu constant region sequences, as well as myriad immunoglobulin variable region sequences. Light chains are classified as either kappa or lambda. Heavy chains are classified as gamma, mu, alpha, delta, or epsilon, which in turn define the immunoglobulin classes, IgG, IgM, IgA, IgD and IgE, respectively.

T cells refer to a particular class of lymphocytes that express a specific receptor (T cell receptor) encoded by a family of genes. The recognized T cell receptor genes include alpha, beta, delta, and gamma loci, and the T cell receptors typically (but not universally) recognize a combination of MHC plus a short peptide. T cells are typically broadly classified as T helper cells (CD4+) and cytotoxic T cells (CD8+). Antibodies are naturally produced by B cells, e.g., Antibody Secreting Cells (ASCs): Mature B cells can be naïve, plasma B cells (activated and antibody-producing), memory, B-1, marginal-zone B cells, follicular B cells, and regulatory B cells.

An adaptive immune response refers to T cell and/or B cell and/or antibody recognition of antigen.

Antigen presenting cells (APCs) are cells that are able to present immunogenic peptides or fragments thereof to T cells to activate or enhance an immune response. APCs include dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may be isolated from any of a variety of biological fluids and organs including bone marrow, peripheral blood, tumor and peritumoral tissues, and may be autologous, allogeneic, syngeneic or xenogeneic cells. APCs typically utilize a receptor from the major histocompatibility (MHC) locus to present short polypeptides to T cells.

An adjuvant is a non-specific immune response enhancer. Suitable adjuvants include, for example, cholera toxin, monophosphoryl lipid A (MPL), Freund's Complete Adjuvant, Freund's Incomplete Adjuvant, Quil A, and Al(OH). Adjuvants can also be those substances that cause APC activation and enhanced presentation of T cells through secondary signaling molecules like Toll-like receptors, e.g., double-stranded RNA (dsRNA), dsRNA mimetic bacterial flagella, LPS, CpG DNA, and bacterial lipopeptide (Reviewed recently in [Abreu et al., J Immunol, 174(8), 4453-4460 (2005)]).

The terms "polypeptide," "peptide" and "protein" are used interchangeably herein to refer to a polymer of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine I, Lysine (K); 5) Isoleucine (I), Leucine (L), Methionine (M), Valine (V), 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The phrase "selectively (or specifically) hybridizes to" refers to the binding, duplexing, or hybridizing of complementary (or largely complementary) nucleotides in a complex mixture (e.g., total cellular or library DNA or RNA).

Polynucleotides may comprise a native sequence (i.e., an endogenous sequence that encodes an individual polypeptide or dsRNA or a portion thereof) or may comprise a variant of such a sequence. Polynucleotide variants may contain one or more substitutions, additions, deletions and/or insertions such that at least one biological activity of the encoded polypeptide (e.g., immunogenicity) is not diminished, relative to a polypeptide comprising native antigens. Polynucleotide variants may contain one or more substitutions, additions, deletions and/or insertions such that the adjuvant activity of an encoded dsRNA is not diminished, relative to a dsRNA that does not contain the substitutions, additions, deletions and/or insertions. Variants preferably exhibit at least about 50%, 55%, 60%, 65%, 70%, 75%, 80%, 85%, 90%, 91%, 92%, 93%, 94%, 95%, 96%, 97%, 98%, or 99% sequence identity to a polynucleotide sequence that encodes a native polypeptide or a portion thereof or a dsRNA.

The terms "identical" or percent "identity," in the context of two or more polynucleotide or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test polynucleotide sequence. Optionally, the identity exists over a region that is at least about 10 to about 100, about 20 to about 75, about 30 to about 50 amino acids or nucleotides in length.

A "control" sample or value refers to a sample that serves as a reference, usually a known reference, for comparison to a test sample. For example, a test sample can be taken from a test condition, e.g., in the presence of a test compound or treatment, and compared to samples from known conditions, e.g., in the absence of the test compound (negative control), or in the presence of a known compound (positive control). In the context of the present disclosure, an example of a negative control would be a biological sample from a known healthy (non-infected) individual, and an example of a positive control would be a biological sample from a known infected patient. A control can also represent an average value or a range gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a: given situation and be able to analyze data based on comparisons to control values. Controls are also valuable for determining the significance of data. For example, if values for a given parameter are widely variant in controls, variation in test samples will not be considered as significant.

The term "diagnosis" refers to a relative probability that a subject has a disorder such as an infection or cancer. Similarly, the term "prognosis" refers to a relative probability that a certain future outcome may occur in the subject. The terms are not intended to be absolute, as will be appreciated by any one of skill in the field of medical diagnostics.

The terms "therapy," "treatment," and "amelioration" refer to any reduction in the severity of symptoms. In the context of infection, treatment can refer to a reduction of infectious agent, reduced symptoms, etc. In the case of treating cancer, treatment can refer to, e.g., reducing tumor size, number of cancer cells, growth rate, metastatic activity, reducing cell death of non-cancer cells, etc. The terms "treat" and "prevent" are not intended to be absolute terms. Treatment and prevention can refer to any comparative reduction or apparent absence of infectious agent, delay in onset, amelioration of symptoms, improvement in patient survival, increase in survival time or rate, etc. Treatment and prevention can be complete (undetectable levels of infectious agent or neoplastic cells) or partial, such that fewer infectious agent or neoplastic cells are found in a patient than would have occurred without the presently described immunogenic biological agents. The effect of treatment can be compared to an individual or pool of individuals not receiving the treatment, or to the same patient prior to treatment or at a different time during treatment. In some aspects, the severity of infection or disease is reduced by at least 10%, as compared, e.g., to the individual before administration or to a control individual not undergoing treatment. In some aspects the severity of infection or disease is reduced by at least 25%, 50%, 75%, 80%, or 90%, or in some cases, no longer detectable using standard diagnostic techniques.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc.

II. IMMUNOGENIC BIOLOGICAL AGENTS

An immunogenic biological agent is any biological agent that causes an immune response in the host, e.g., human host. The immunogenic biological agent can thus be a polypeptide (e.g., glycoprotein, phosphoprotein, or other modified form), carbohydrate, lipid, polynucleotide (e.g., chromatin, methylated polynucleotide, or other modified form). In some embodiments, the immunogenic biological agent directly causes an immune response, e.g., is itself a target immunogen (antigen). In some embodiments, the immunogenic biological agent is a polynucleotide encoding the target immunogen. For example, when a polynucleotide encoding a target antigen is expressed in an antigen presenting cell (APC), an immune response is mounted against the expressed antigen. The immunogenic biological agent can be administered alone, in combination with a second, third, and/or fourth immunogenic biological agent (e.g., in the case of a multi-target preventative vaccine), and/or in combination with an adjuvant to increase the immune response.

A. Expression Vectors

Expression vectors for use as described herein can include virally-derived vectors, e.g., recombinant adeno-associated virus (AAV) vectors, retroviral vectors, adenoviral vectors, modified vaccinia Ankara (MVA) vectors, and lentiviral (e.g., HSV-1-derived) vectors (see, e.g., Brouard et al. (2009) *British J. Pharm.* 157:153). Virally-derived vectors for therapeutic use are typically rendered replication incompetent or attenuated. For example, in the case of an adenoviral vector, the adenoviral genome can be modified to remove the E1 and E3 genes. For production, the replication deficient vector can be administered to a cell that expresses the E1 gene such that recombinant adenovirus (rAd) is produced by the cell. This rAd can be harvested and used for a single round of infection to deliver the transgenic composition to another cell within a mammal in order to elicit immune responses to an encoded polypeptide antigen.

Examples of suitable viral vectors include adenovirus 5, including, for example, Ad5 with deletions of the E1/E3 regions and Ad5 with a deletion of the E4 region as described in U.S. Pat. No. 8,222,224 and Scallan et al. Clinical and Vaccine Immunology 2013; 20(1): 85-94. An exemplary Ad5 viral vector backbone is provided in SEQ ID NO: 7. Other suitable adenoviral vectors include strains 2, orally tested strains 4 and 7, enteric adenoviruses 40 and 41, and other strains (e.g. Ad34, Ad26, or Ad35) that are sufficient for delivering an antigen and eliciting an adaptive immune response to the transgene antigen [Lubeck et al., Proc Natl Aced Sci USA, 86(17), 6763-6767 (1989); Shen et at, J Virol, 75(9), 42974307 (2001); Bailey et al., Virology, 202(2), 695-706 (1994)]. The viral vector does not need to have been isolated from humans, but can come from a non-human such as chimpanzee adenovirus 3 (ChAd3) (see, e.g., Colloca et al. (2012) *Sci. Tranl. Med* 4:115; Stanley et al. (2014) *Nat. Med* doi:10.1038/nm.3702). In some embodiments, the adenoviral vector is a live, replication incompetent adenoviral vector (such as E1 and E3 deleted rAd5), live and attenuated adenoviral vector (such as the E1B55K deletion viruses), or a live adenoviral vector with wild-type replication.

Transcriptional and translational control sequences in expression vectors to be used as described herein can be provided by viral sources. For example, commonly used promoters and enhancers are derived, e.g., from beta actin, adenovirus, simian virus (SV40), and human cytomegalovirus (CMV). For example, vectors allowing expression of proteins under the direction of the CMV promoter, SV40 early promoter, SV40 later promoter, metallothionein promoter, murine mammary tumor virus promoter, Rous sarcoma virus promoter, transducer promoter, or other promoters shown effective for expression in mammalian cells are suitable. Additional viral and non-viral promoter, control and/or signal sequences may be used, provided such control sequences are compatible with the host cells to be transfected.

B. Immunogens

Immunogens for use as described herein can be derived from antigens, such as, for example, viral antigens, bacterial antigens, cancer antigens, fungal antigens, or parasite antigens (see, e.g., U.S. Pat. No. 8,222,224 for a list of antigens that can be used as described herein).

Particular examples of antigens that can be used as described herein are those derived from norovirus (e.g., VP1) and Respiratory syncytial virus (RSV) (e.g.). Other suitable antigens include those from the influenza virus (e.g., HA, NA, M1, NP), human immunodeficiency virus (HIV, e.g., gag, pol, env, etc.), human papilloma virus (HPV, e.g., capsid proteins such as L1), Venezuelan Equine Encephalomyelitis (VEE) virus, Epstein Barr virus, herpes simplex virus (HSV), human herpes virus, rhinoviruses, cocksackieviruses, enteroviruses, hepatitis A, B, C, E, and G (HAV, HBV, HCV, HEV, HGV e.g., surface antigen), mumps virus, rubella virus, measles virus, poliovirus, smallpox virus, rabies virus, and Varicella-zoster virus.

Suitable viral antigens also include viral nonstructural proteins, e.g., proteins encoded by viral nucleic acid that do not encode for structural polypeptides, in contrast to those that make capsid or the protein surrounding a virus. Nonstructural proteins include those proteins that promote viral nucleic acid replication, viral gene expression, or post-translational processing, such as, for example, Nonstructural proteins 1, 2, 3, and 4 (NS1, NS2, NS3, and NS4, respectively) from Venezuelan Equine encephalitis (VEE), Eastern Equine Encephalitis (EEE), or Semliki Forest.

Bacterial antigens can be derived from, for example, *Staphylococcus aureus, Staphylococcus epidermis, Helicobacter pylori, Streptococcus bovis, Streptococcus pyogenes, Streptococcus pneumoniae, Listeria monocytogenes, Mycobacterium tuberculosis, Mycobacterium leprae, Corynebacterium diphtheriae, Borrelia burgdorferi, Bacillus anthracis, Bacillus cereus, Clostridium botulinum, Clostridium difficile, Salmonella typhi, Vibrio chloerae, Haemophilus influenzae, Bordetella pertussis, Yersinia pestis, Neisseria gonorrhoeae, Treponema pallidum, Mycoplasm* sp., *Legionella pneumophila, Rickettsia typhi, Chlamydia trachomatis,* and *Shigella dysenteriae, Vibrio cholera* (e.g., Cholera toxin subunit B, cholera toxin-coregulated pilus (TCP)); *Helicobacter pylori* (e.g., VacA, CagA, NAP, Hsp, catalase, unease); *E. coli* (e.g., heat-labile enterotoxin, fimbrial antigens).

Parasite antigens can be derived from, for example, *Giardia lamblia, Leishmania* sp., *Trypanosoma* sp., *Trichomonas* sp., *Plasmodium* sp. (e.g., *P. falciparum* surface protein antigens such as pfs25, pfs28, pfs45, pfs84, pfs 48/45, pfs 230, Pvs25, and Pvs28); *Schistosoma* sp.; *Mycobacterium tuberculosis* (e.g., Ag85, MPT64, ESAT-6, CFP10, R8307, MTB-32 MTB-39, CSP, LSA-1, LSA-3, EXP1, SSP-2, SALSA, STARP, GLURP, MSP-1, MSP-2, MSP-3, MSP-4, MSP-5, MSP-8, MSP-9, AMA-1, Type 1 integral membrane protein, RESA, EBA-175, and DBA).

Fungal antigens can be derived from, for example, *Tinea pedis, Tinea corporus, Tinea cruris, Tinea unguium, Cladosporium carionii, Coccidioides immitis, Candida* sp., *Aspergillus fumigatus*, and *Pneumocystis carinii*.

Cancer antigens include, for example, antigens expressed or over-expressed in colon cancer, stomach cancer, pancreatic cancer, lung cancer, ovarian cancer, prostate cancer, breast cancer, skin cancer (e.g., melanoma), leukemia, or lymphoma Exemplary cancer antigens include, for example, HPV L1, HPV L2, HPV E1, HPV E2, placental alkaline phosphatase, AFP, BRCA1, Her2/neu, CA 15-3, CA 19-9, CA-125, CEA, Hcg, urokinase-type plasminogen activator (Upa), plasminogen activator inhibitor, CD53, CD30, CD25, C5, CD11a, CD33, CD20, ErbB2, CTLA-4. See Sliwkowski & Mellman (2013) *Science* 341:6151 for additional cancer targets.

C. Adjuvants

In some embodiments, the compositions further comprise at least one adjuvant. Suitable adjuvants include, for example, the lipids and non-lipid compounds, cholera toxin (CT), CT subunit B, CT derivative CTK63, *E. coli* heat labile enterotoxin (LT), LT derivative LTK63, Al(OH)$_3$, and polyionic organic acids as described WO2004/020592, Anderson and Crowle, Infect. Immun. 31(1):413-418 (1981), Roterman et al., J. Physiol. Pharmacol., 44(3):213-32 (1993), Arora and Crowle, J. Reticuloendothel. 24(3): 271-86 (1978), and Crowle and May, Infect. Immun. 38(3): 932-7 (1982)). Suitable polyionic organic acids include for example, 6,6'-[3,3'-demithyl[1,1'-biphenyl]-4,4'-diyl]bis (azo)bis[4-amino-5-hydrox-y-1,3-naphthalene-disulfonic acid] (Evans Blue) and 3,3'-[1,1' biphenyl]-4,4'-diylbis(azo) bis[4-amino-1-naphthalenesulfonic acid] (Congo Red). It will be appreciated by those of skill in the art that the polyionic organic acids may be used for any nucleic acid-based vaccination method in conjunction with any type of administration.

TLR-3 agonists (e.g., dsRNA, and mimetics thereof such as polyI:C, poly A:U, and polyI:polyC) can also be used. TLR-3 agonists include, for example, short hairpin RNA, virally derived RNA, short segments of RNA that can form double-strands or short hairpin RNA, and short interfering RNA (siRNA). In some embodiments, the TLR-3 agonist is virally derived dsRNA, e.g., dsRNA derived from a Sindbis virus or dsRNA viral intermediates (Alexopoulou et al. (2001) Nature 413:732). In some embodiments, the TLR-3 agonist is a short hairpin RNA. Short hairpin RNA sequences typically comprise two complementary sequences joined by a linker sequence. The particular linker sequence is not a critical aspect of the invention. Any appropriate linker sequence can be used so long as it does not interfere with the binding of the two complementary sequences to form a dsRNA. TLR-3 agonists can result in pro-inflammatory cytokine release (e.g. IL-6, IL-8, TNF-alpha, IFN-alpha, IFN-beta) when contacted with a responder cell (e.g., a dendritic cell, a peripheral blood mononuclear cell, or a macrophage) in vitro or in-vivo.

Other suitable adjuvants include topical immunomodulators such as, members of the imidazoquinoline family such as, for example, imiquimod and resiquimod (see, e.g., Hengge el al., Lancet Infect. Dis. 1(3):189-98(2001).

Additional suitable adjuvants are commercially available as, for example, additional alum-based adjuvants (e.g., Alhydrogel, Rehydragel, aluminum phosphate, Algammulin); oil based adjuvants (Freund's Incomplete Adjuvant and Complete Adjuvant (Difco Laboratories, Detroit, Mich.), Specol, RIBI, TiterMax, Montanide ISA50 or Seppic MONTANIDE ISA 720); nonionic block copolymer-based adjuvants, cytokines (e.g., GM-CSF or Flat3-ligand); Merck Adjuvant 65 (Merck and Company, Inc., Rahway, N.J.); AS-2 (SmithKline Beecham, Philadelphia, Pa.); salts of calcium, iron or zinc; an insoluble suspension of acylated tyrosine; acylated sugars; cationically or anionically derivatized polysaccharides; polyphosphazenes; biodegradable microspheres; monophosphoryl lipid A and Quil A. Cytokines, such as GM-CSF or interleukin-2, -7, or -12, are also suitable adjuvants. Hemocyanins (e.g., keyhole limpet hemocyanin) and hemoerythrins can also be used as adjuvants. Polysaccharide adjuvants such as, for example, chitin, chitosan, and deacetylated chitin are also suitable as adjuvants. Other suitable adjuvants include muramyl dipeptide (MDP, N acetylmuramyl L alanyl D isoglutamine) bacterial peptidoglycans and their derivatives (e.g., threonyl-MDP, and MTPPE). BCG and BCG cell wall skeleton (CWS) can be used as adjuvants, with or without trehalose dimycolate. Trehalose dimycolate can be used itself (see, e.g., U.S. Pat. No. 4,579,945). Detoxified endotoxins are also useful as adjuvants alone or in combination with other adjuvants (see. e.g., U.S. Pat. Nos. 4,866,034; 4,435,386; 4,505,899; 4,436, 727; 4,436,728; 4,505,900; and 4,520,019). The saponins QS21, QS17, QS7 are also useful as adjuvants (see, e.g., U.S. Pat. No. 5,057,540; EP 0362 279; WO 96/33739; and WO 96/11711). Other suitable adjuvants include Montanide ISA 720 (Seppic, France), SAF (Chiron, Calif., United States), ISCOMS (CSL), MF-59 (Chiron), the SBAS series of adjuvants (e.g., SBAS-2, SBAS-4 or SBAS-6 or variants thereof, available from SmithKline Beecham, Rixensart, Belgium), Detox (Corixa, Hamilton, Mont.), and RC-529 (Corixa, Hamilton, Mont.).

Superantigens are also contemplated for use as adjuvants in the present invention. Superantigens include *Staphylococcus* exoproteins, such as the alpha, beta, gamma, and delta enterotoxins from *S. aureus* and *S. epidermidis*, and the alpha, beta, gamma, and delta-*E. coli* exotoxins. Common *Staphylococcus* enterotoicins are known as staphylococcal enterotoxin A (SEA) and staphylococcal enterotoxin B (SEB), with enterotoxins through E (SEE) being described (Rott et al., 1992). *Streptococcus pyogenes* B (SEB), *Clostridium perfringens* enterotoxin (Bowness et al., 1992), cytoplasmic membrane-associated protein (CAP) from *S. pyogenes* (Sato et al., 1994) and toxic shock syndrome toxin 1 (TSST 1) from *S. aureus* (Schwab et al., 1993) can also be used.

For the pharmaceutical compositions provided herein, the adjuvant(s) can be designed to induce, e.g., an immune response predominantly of the Th1 or Th2 type. High levels of Th1-type cytokines (e.g., IFN-gamma, TNF-alpha, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following oral delivery of a composition comprising an immunogenic polypeptide as provided herein, an immune response that includes Th1- and Th2-type responses will typically be elicited.

III. TARGETED DELIVERY SYSTEMS

The presently described compositions and methods for ileal delivery can rely on appropriate coatings, matrices, and devices such as those described below.

A. Enteric Coatings, Matrices, and Devices

Enteric coatings are used to shield substances from the low pH environment of the stomach and delay release of the enclosed substance until it reaches a desired target later in the digestive tract. Enteric coatings are known, and commercially available. Examples include pH-sensitive polymers, bio-degradable polymers, hydrogels, time-release systems, and osmotic delivery systems (see, e.g., Chourasia & Jain (2003) *J. Pharm. Pharmaceutical Sci.* 6:33).

The pH of the gastrointestinal tract (GIT) progresses from very acidic in the stomach (pH ~2), to more neutral in the ileum (pH ~5.8-7.0). pH sensitive coatings can be used that dissolve in the ileum or just before the ileum. Examples include Eudragit® L and S polymers (threshold pH's ranging from 5.5-7.0); polyvinyl acetate phthalate (pH 5.0), hydroxypropyl methylcellulose phthalate 50 and 55 (pH 5.2 and 5.4, respectively), and cellulose acetate phthalate (pH 5.0). Thakral et al. (2013) *Expert Opin. Drug Deliv.* 10:131 review Euragit® formulations for ileal delivery, in particular, combinations of L and S that ensure delivery at pH≤7.0. Crotts et al. (2001) *Eur. J Pharm. Biol.* 51:71 describe Eudragit® formulations with appropriate disintegration properties. Vijay et al. (2010) *J. Mater. Sci. Mater. Med* 21:2583 review acrylic acid (AA)-methyl methacrylate (MMA) based copolymers for ileal delivery at pH 6.8.

For ileal delivery, the polymer coating typically dissolves at about pH 6.8 and allows complete release within about 40 min (See, e.g., Huyghebaert et at (2005) *Int. J. Pharm.* 298:26). To accomplish this, a therapeutic substance can be covered in layers of different coatings, e.g., so that the outermost layer protects the substance through low pH conditions and is dissolved when the tablet leaves the stomach, and at least one inner layer that dissolves as the tablet passes into increasing pH. Examples of layered coatings for delivery to the distal ileum are described, e.g., in WO2013148258.

Biodegradable polymers (e.g., pectin, azo polymers) typically rely on the enzymatic activity of microflora living in the GIT. The ileum harbors larger numbers of bacteria than earlier stages, including lactobacilli and enterobacteria.

Osmotic-controlled Release Oral delivery Systems (OROS®; Alza) is an example of an osmotic system that degrades over time in aqueous conditions. Such materials can be manipulated with other coatings, or in varying thicknesses, to deliver specifically to the ileum (see, e.g., Conley et al. (2006) *Curr. Med. Res. Opin.* 22:1879).

Combination polymers for delivery to the ileum are reported in WO2000062820. Examples include Eudragit® L100-55 (25 mg/capsule) with triethyl citrate (2.4 mg/capsule), and Povidone K-25 (20 mg/tablet) followed by Eudragit® FS30D (30 mg/tablet). pH sensitive polymers can be applied to effect delivery to the ileum, as described above and, e.g., methacrylic acid copolymers (e.g., poly(methacrylic acid-co-methyl methacrylate) 1:1), cellulose acetate phthalate, hydroxypropyl methylcellulose phthalate, hydroxypropyl methylcellulose acetate succinate, polyvinyl acetate phthalate, cellulose acetate trimellitate, carboxymethyl ethyl-cellulose, shellac or other suitable polymer(s). The coating layer can also be composed of film-forming polymers being sensitive to other luminal components than pH, such as bacterial degradation or a component that has such a sensitivity when it is mixed with another film-forming polymer. Examples of such components providing delayed release to the ileum are polymers comprising azo bond(s), polysaccharides such as pectin and its salts, galactomannans, amylose and chondroitin, disulphide polymer's and glycosides.

Components with varying pH, water, and enzymatic sensitivities can be used in combination to target a therapeutic composition to the ileum. The thickness of the coating can also be used to control release. The components can also be used to form a matrix, in which the therapeutic composition is embedded. See generally, *Frontiers in Drug Design & Discovery* (Bentham Science Pub. 2009) vol. 0.4.

B. Frequency or Radio-Controlled Capsules

As an alternative to dissolving coatings and matrices, site-specific delivery can be via capsules that release upon an externally generated signal, Early models released for a high-frequency (HF) signal, as disclosed in Digenis et at (1998) *Pharm. Sci. Tech. Today* 1:160. The original HF capsule concept has since been updated and the result marketed as InteliSite®. The updated capsule is a radio-frequency activated, non-disintegrating delivery system. Radiolabeling of the capsule permits the determination of the capsule location within a specific region of the GI tract via gamma scintigraphy. When the capsule reaches the desired location in the GI tract, external activation opens a series of windows to the capsule drug reservoir.

In some embodiments, the immunogenic biological agent can be enclosed in a radio-controlled capsule, so that the capsule is tracked and signaled once it reaches the ileum. In some embodiments, the capsule is signaled at a given time after administration that corresponds to when the capsule is expected to arrive in the ileum, with or without detecting.

C. Formulations

Pharmaceutical compositions can be used for prophylactic and therapeutic purposes as described herein. As explained above, pharmaceutical compositions can be prepared to protect against stomach degradation such that the administered immunogenic biological agent reach the desired location. Methods for microencapsulation of DNA and drugs for oral delivery are described, e.g., in US2004043952.

An immunogenic pharmaceutical composition can contain pharmaceutically acceptable salts of the immunogenic biological agent (e.g., immunogenic polypeptide, or polynucleotide encoding an immunogenic polypeptide). Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts). Some particular examples of salts include phosphate buffered saline and saline (e.g., for ingestion, nasal delivery, or injection).

A delayed release coating or an additional coating of the formulation can contain other film-forming polymers being non-sensitive to turning conditions for technical reasons or chronographic control of the drug release. Materials to be used for such purpose includes, but are not limited to; sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures.

Additives such as dispersants, colorants, pigments, additional polymers, e.g., poly(ethylacrylat, methylmethacrylat), anti-tacking and anti-foaming agents can be included into a coating layer. Other compounds may be added to increase film thickness and to decrease diffusion of acidic gastric juices into the core material. The coating layers can also contain pharmaceutically acceptable plasticizers to obtain desired mechanical properties. Such plasticizers are for instance, but not restricted to, triacetin, citric acid esters, phthalic acid esters, dibutyl sebacate, cetyl alcohol, polyethylene glycols, glycerol monoesters, polysorbates or other plasticizers and mixtures thereof. The amount of plasticizer can be optimised for each formula, and in relation to the selected polymer(s), selected plasticizer(s) and the applied amount of said polymer(s).

Other suitable pharmaceutical ingredients known in the art can be employed in the pharmaceutical compositions of this invention. Suitable carriers include, for example, water, saline, alcohol, a fat, a wax, a buffer, a solid carrier, such as mannitol, lactose, starch, magnesium stearate, sodium saccharine, talcum, cellulose, glucose, sucrose, and magnesium carbonate, or biodegradable microspheres (e.g., polylactate polyglycolate). Suitable biodegradable microspheres are disclosed, for example, in U.S. Pat. Nos. 4,897,268; 5,075,109; 5,928,647; 5,811,128; 5,820,883. The immunogenic polypeptide and/or carrier expression vector can be encapsulated within the biodegradable microsphere or associated with the surface of the microsphere.

Such compositions may also comprise non-immunogenic buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), suspending agents, thickening agents and/or preservatives. Alternatively, compositions of the present invention may be formulated as a lyophilate. Compounds may also be encapsulated within liposomes using well known technology.

IV. IMMUNE RESPONSES AND VACCINES

The pharmaceutical compositions for ileum delivery as described herein are designed to elicit an immune response from an individual that is specific for an immunogenic biological agent included in the pharmaceutical composition. The pharmaceutical composition can be used prophylactically or therapeutically as a vaccine to avoid or reduce a viral infection, bacterial infection, parasitic infection, fungal infection, or cancer. The pharmaceutical compositions can be used to treat at any stage, e.g., at the pre-cancer, cancer, or metastatic stages, or to prevent disease or infection.

For example, the compositions described herein may be used to prevent or treat infection, such as influenza, hepatitis, or HIV, or for prevention or treatment of cancer. Within such methods, pharmaceutical compositions are typically administered to an individual that may or may not be afflicted with the disease, disorder, or infection. In some embodiments, a disease, disorder, or infection is diagnosed prior to administration, e.g., using criteria generally accepted in the art. For example, viral infection may be diagnosed by the measurement of viral titer in a sample from the patient, bacterial infection may be diagnosed by detecting the bacteria in a sample from the patient, and cancer may be diagnosed by detecting the presence of a malignant tumor. Pharmaceutical compositions can be administered either prior to or following surgical removal of primary tumors and/or treatment such as administration of radiotherapy or conventional chemotherapeutic drugs.

Immunotherapy is typically active immunotherapy, in which treatment relies on the in vivo stimulation of the endogenous host immune system to react against, e.g., tumors or bacterially or virally infected cells, with the administration of immune response-modifying agents (e.g., immunogenic biological agents).

Frequency of administration of the prophylactic or therapeutic compositions described herein, as well as dosage, will vary from individual to individual, and can be readily established using standard techniques. Typically, between 1 and 52 doses can be administered over a 52 week period. In some embodiments, 3 doses are administered, at intervals of 1 month, or 2-3 doses are administered every 2-3 months. In some embodiments, a combination of more than one antigen can be administered simultaneously or sequentially, e.g., an annual influenza vaccine that contains individual components directed at each subtype of influenza or multiple clades within a subtype. In some embodiments, the intervals are more like once a year, e.g., an annual flu vaccine based on the particular current strain. Booster vaccinations can be given periodically, thereafter. Alternate protocols may be appropriate for individual patients and particular diseases and disorders.

A suitable dose is an amount of an immunogenic biological agent that, when administered as described above, is capable of promoting, e.g., an anti-tumor, an anti-viral, or an antibacterial, immune response, and is at least 15-50% above the basal (untreated) level, or at least 5-50% (e.g., 5%, 10%, 20%, 30%, 50%, 1.5-fold, 2-fold, or higher) above the level from non-ileum targeted treatment. Such response can be monitored by measuring the anti tumor antibodies in a patient or by vaccine-dependent generation of cytolytic T cells capable of killing, e.g., the patient's tumor cells, the patient's virally infected cells, or the patient's bacterially infected cells in vitro. Such vaccines can also generate an immune response that leads to an improved clinical outcome (e.g., complete or partial or longer disease-free survival, reduced viral titers) in vaccinated patients as compared to non-vaccinated patients, or patients receiving non-ileum targeted treatment.

In general, an appropriate dosage and treatment regimen provides the active compound(s) in an amount sufficient to provide therapeutic and/or prophylactic benefit. Such a response can be monitored by establishing an improved clinical outcome (e.g., reduced or negative viral titer, more frequent remissions, complete or partial, or longer disease-free survival) in treated patients as compared to patients treated with non-ileum targeted treatment, or non-treated patients. Such immune responses can generally be evaluated using standard proliferation, cytotoxicity or cytokine assays described above, which can be performed using samples obtained from a patient before and after treatment.

For example, detection of immunocomplexes formed between an immunogenic polypeptide and antibodies in body fluid that are specific for the immunogenic polypeptide can be used to monitor the effectiveness of therapy, e.g., for a disease or disorder in which the immunogenic polypeptide is associated. Samples of body fluid taken from an individual prior to and subsequent to initiation of therapy (e.g., ileum-targeted therapy) may be analyzed for the immunocomplexes using known methods. Briefly, the number of immunocomplexes detected in both samples is compared. A significant change hi the number of immunocomplexes in the second sample (post-targeted therapy) relative to the first sample (pre-targeted therapy) reflects successful therapy.

V. EXAMPLES

Pharmaceutical methods for delivering small molecules to the intestine are known, but the ability to deliver a large biological to the intestine for proper immune recognition is poorly understood. Mice are not able to swallow pills, so it is difficult to perform studies with tablets in animal models. Further, the location of the best place to deliver the vaccine vector in order to elicit a response to transgene antigen has not been characterized in humans. In sheep, the jejunum was shown to be the most effective target for eliciting an immune response to an adenovirally-encoded transgene antigen (Mutwari et al. (1999) *Immunology* 97:455). Here we show the result of several human or non-human primate studies with improved human oral dosage forms for delivery of biological agents.

Example 1

In order to determine which region of the small intestine is most active for inducing an immune response to antigen, tests were performed in humans. Radio-controlled capsules were given to healthy normal volunteers, with the vaccine either released early in the small intestine (jejunum) or later in the small intestine (ileum). The use of the radio-controlled capsules for delivery of small molecule drugs has been described, but not for vaccine delivery (Digenis et al. (1991) *Crit. Rev. Ther. Drug Carrier Syst.* 7:309).

The vaccine was composed of recombinant adenovirus expressing the influenza antigen HA from A/CA/04/2009 (rAd-HA-dsRNA) (see, e.g., US2012/0244185). A total of $10^{11}$ infectious units (IU) were given to each subject on day 0. The numbers of circulating pre-plasma B cells in peripheral blood were measured by Antibody Secreting Cell (ASC) assay on days 0 and 7 after the administration of the vaccine. Results only measure the numbers of ASCs that recognize the antigen HA.

Results show that ASCs could be measured 7 days after immunization in each of the treated groups (FIG. 1). Average responses were higher in the ileum dosed group than the jejunum dosed group. Background ASCs on day 0 were negligible. For the ileum, an average of 340+/−111 (standard error) IgG and 74+/−18 IgA ASCs were observed on day 7. For the jejunum, the average and standard error responses were 118+/−30 IgG and 28+/−8 IgA ASCs. The ileum group was significantly different than placebo (P=0.03 on day 7 for IgA ASC, and trended higher for IgG ASC p=0.07). Contrary to the results in sheep, the results in humans indicate that ileum delivery is more potent at eliciting an IgG or an IgA antibody response than jejunum delivery.

Figure 2:
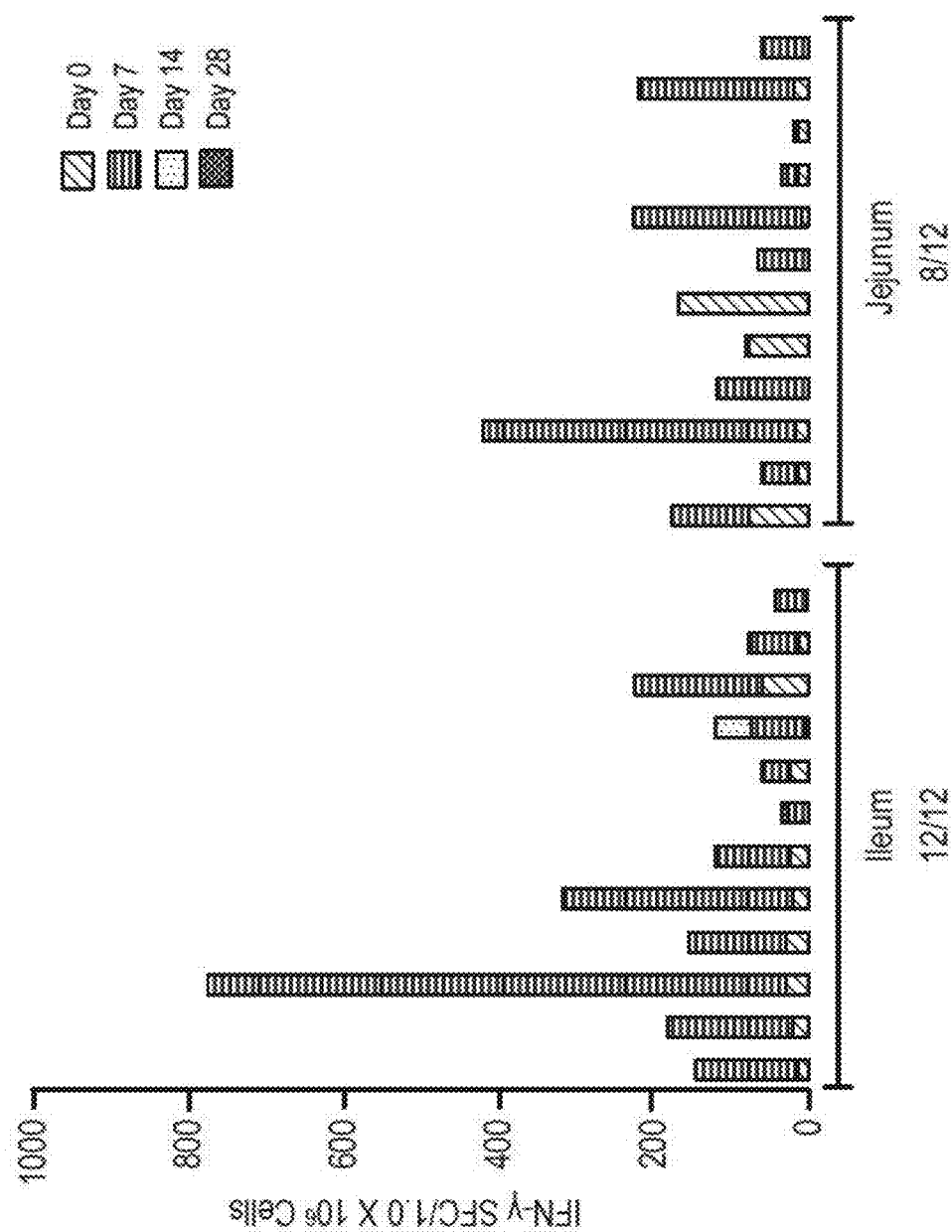
FIG. 2. T cell response to rAd-HA-dsRNA was determined by detecting IFN-γlevels 7 days post-administration. All of the individuals in the ileum-delivery group showed higher levels of IFN-γ, compared to 75% of the jejunum-delivery group. The average IFN-γ level was also significantly higher in the ileum-delivery group.

T cell responses were also determined by detecting interferon-γ release (IFN-γ) using the ELISPOT® assay. FIG. 2 shows that 12/12 of the ileum-dosed group had increased levels of IFN-γ, compared to 8/12 of the jejunum-dosed group 7 days post-administration. In addition, IFN-γ levels were significantly higher in the ileum-dosed group than in the jejunum-dosed group.

Figure 3:
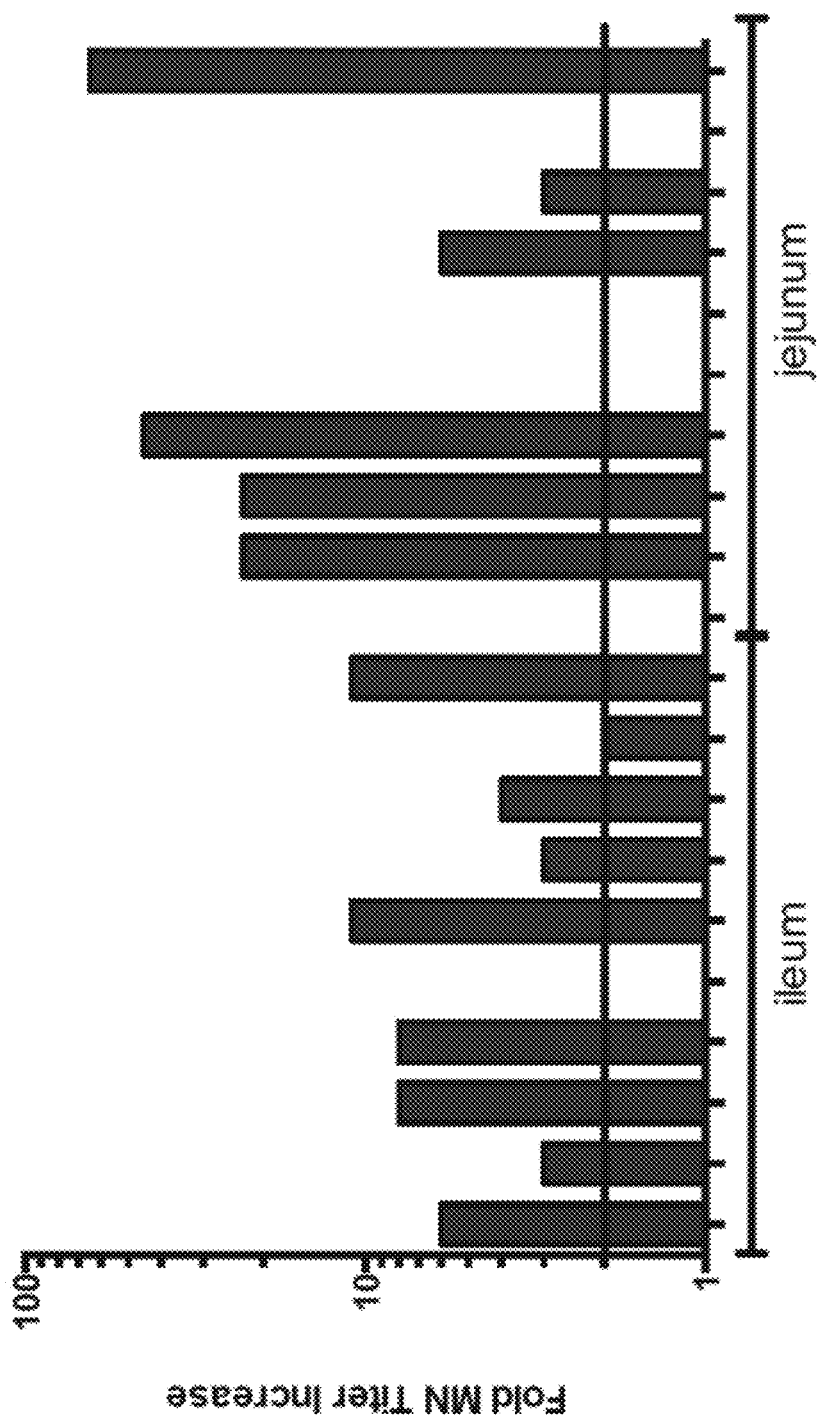
FIG. 3. Microneutralizing antibody (MN) responses to influenza A/CA/07/2009 were measured at day 0 and day 28 after immunization. The fold increase in MN titers was plotted for individual subjects that had an initial MN titer less than or equal to 40. Results showed that ileum delivery resulted in a high proportion of subjects (9 of 10) with increased MN titers following immunization compared to jejunum delivery (6 of 10).

Microneutralizing (MN) antibody titers to influenza A/CA/07/2009 were measured. Increased MN antibody levels are indicative of a neutralizing antibody response. After excluding subjects that had an initial neutralizing antibody response greater than 40 (Faix et al. (2012) *PloS One* 7:e34581), the fold increases in MN titers were plotted for individual subjects. The number of subjects with a positive increase was 9 out of 10 for the ileum delivered vaccine versus 6 out of 10 for jejunum delivered vaccine (FIG. 3). The geometric mean titers (GMT) were similar between the two groups, with ileum GMT rising from 22 to 92 versus the jejunum GMT rising from 18 to 90. The results indicate that ileum release is more reliable at inducing neutralizing antibody responses to influenza, possibly leading to a greater percentage of subjects protected against influenza.

Example 2

Tablets were hand made using microcrystalline cellulose (PH-101, FMC) and starch (Starch 1500, Colorcon) incorporating 10% barium sulfate as a radiopaque material containing fumed silica as a flow aid and magnesium stearate as a tablet lubricant. The tablets of 7.14 mm diameter and 150 mg weight were coated with Eudragit® L-100 in a pan coater using 10% coating solids weight gain as a guide to whether the enteric coating was added; coating solids contained 4 parts Eudragit® polymer to one part triethyl citrate and 1 part talc. As an initial test of enteric coating performance, four cynomolgus macaques were given tablets using an oral gastric tube. The oral gastric tube is solid and rigid, but hollow down the middle for instilling liquids. It has a flexible silicone tube on the leading end of the rigid tube that can hold a small tablet in place. The tube and pill apparatus were threaded down the esophagus of restrained monkeys until the leading end passed through the cardiac sphincter and into the stomach. A flush of orange juice was used to dislodge the pill into the stomach. X-rays were taken at set time points, and examined for location and dissolution of the tablet. Table 1 summarizes the results.

TABLE 1

L-100 coating performance

| | Time and Pill Location | | | |
|---|---|---|---|---|
| Animal | 1 hr | 2 hr | 3 hr | 4 hr |
| 1 | stomach | stomach | stomach | intestine |
| 2 | stomach | intestine | intestine | dissolved |
| 3 | intestine | intestine | dissolved | dissolved |
| 4 | stomach | stomach | intestine | dissolved |

Figures 4A, 4B:
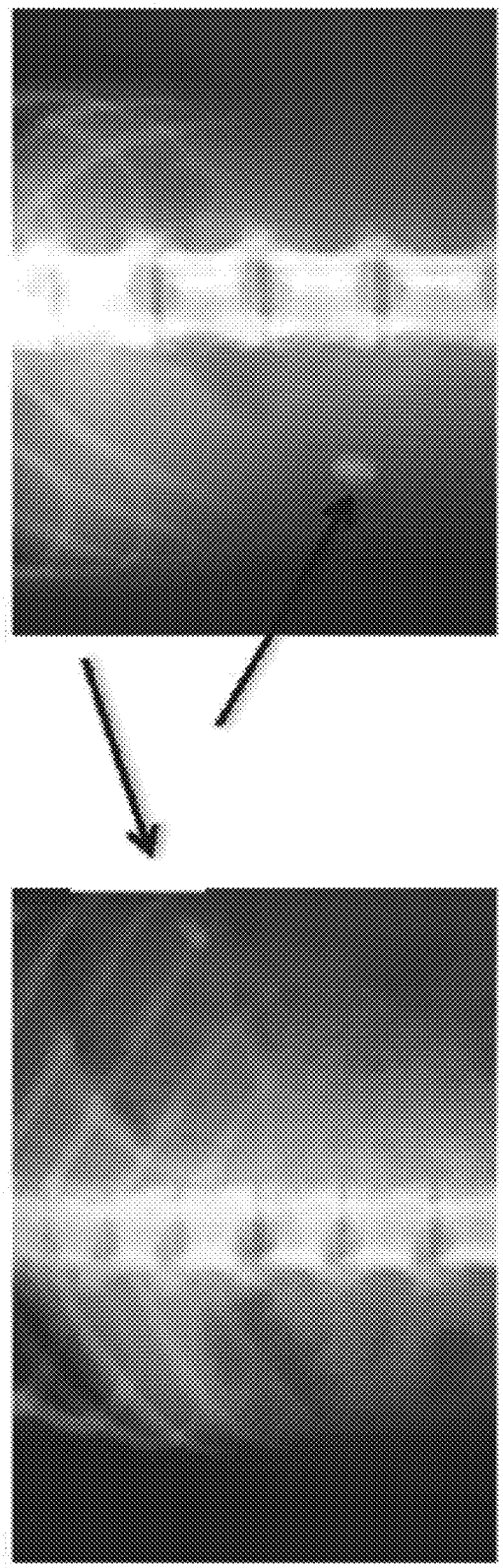
FIG. 4A-4B. Tablets were made using microcrystalline cellulose and starch, with 10% barium sulfate as a radiopaque material. These tablets were enteric coated with Eudragit L100® and given to female cynomolgus macaques by oral gastric tube. X-rays were taken over time post administration.

FIG. 4 shows that the tablets were completely intact in the low pH environment of the stomach; there was no evidence of premature dissolution of the tablets. While large for a monkey, the tablets were able to pass through the stomach intact into the intestine. In the intestine, they dissolved at a reasonable rate and were completely dissolved in 3 out of 4 monkeys. In the 4th monkey, the pill left the stomach sometime after 3 hours and the pill had not dissolved at the time of the last x-ray. Overall, the tablets performed in an acceptable manner and the Eudragit® L-100 coating was selected for future human studies.

Example 3

A phase 1, sequentially enrolled clinical study, with a randomized and placebo-controlled cohort to evaluate safety, and immunogenicity of a recombinant Ad serotype 5 (rAd5) based oral vaccine against H1 seasonal influenza was completed. The rAd5 vector (rAd-HA-dsRNA with HA from A/CA/04/2009) was described in Example 1. The study had an active phase of approximately 3 months, and was conducted in accordance with applicable Good Clinical Practice guidelines, the United States Code of Federal Regulations, and the International Conference on Harmonization guidelines. Informed consent was obtained from all subjects after discussion of the risks. IRB approval was given before dosing of subjects.

Good manufacturing practice (GMP)-grade rAd-HA-dsRNA was produced in Wave® bags (GE Healthcare, Waukesha, Wis.) at Lonza Biologicals (Houston, Tex.). Purification was performed by ion exchange chromatography, followed by buffer exchange. Purified vector was mixed with excipients, lyophilized, and then tableted at Lonza using microcrystalline cellulose and starch as tableting bulk: Tablets were enteric coated with Eudragit® L 100 (Evonik Industries, Darmstadt, Germany) using a Vector HiCoater® LDCS-5 coater (Vector Freund, Cedar Rapids, Iowa). The final product was released in one lot; and titered by standard IU assay. Placebo was prepared as similarly sized and shaped tablets containing 150 mg of microcrystalline cellulose, without enteric coating. The study compared $10^9$ IU, $10^{10}$ IU, and placebo treated subjects for the ability to elicit an immune response to transgene. Subjects were given tablets on days 0 and 28.

Figure 5:
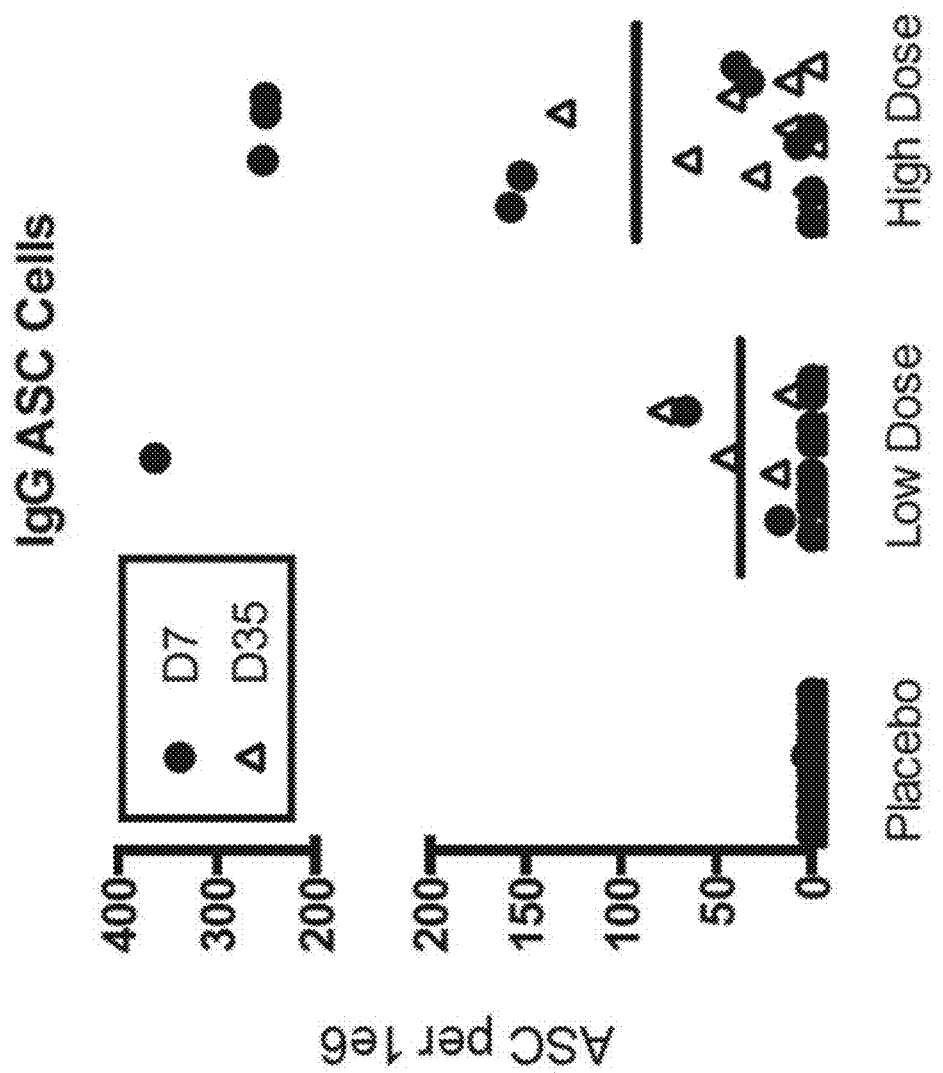
FIG. 5. The numbers of ASCs are reported on days 7 and 35, 7 days after each immunization. Background ASCs at days 0 and 28 were miniscule, and not plotted. Average responses for day 7 are shown for each treated group with a horizontal line.

The numbers of circulating pre-plasma B cells in peripheral blood were measured by ASC assays on days 0 and 7 after the initial dose, and at days 28 and 35 after the second dose (the second dose was delivered at day 28). Results show that ASC counts could be measured 7 days after each immunization in the treated groups, but not the placebo group (FIG. 5). Average responses were higher on day 7, and higher in the high dose group than the low dose group. Background ASCs on days 0 and 28 were negligible, and negligible for the placebo group at all time points. For the high dose group, an average of 105+/−33 and 27+/−12 ASCs were found for days 7 and 35 respectively. For the low dose group, average ASCs were 41+/−32 and 14+/−8 for days 7 and 35 respectively. The placebo group, had an average of 0.3+/−0.3 and 0, for days 7 and 35 respectively. The high dose group was significantly higher than placebo (P/01 and 0.05 for days 7 and 35 respectively.)

Figure 6:
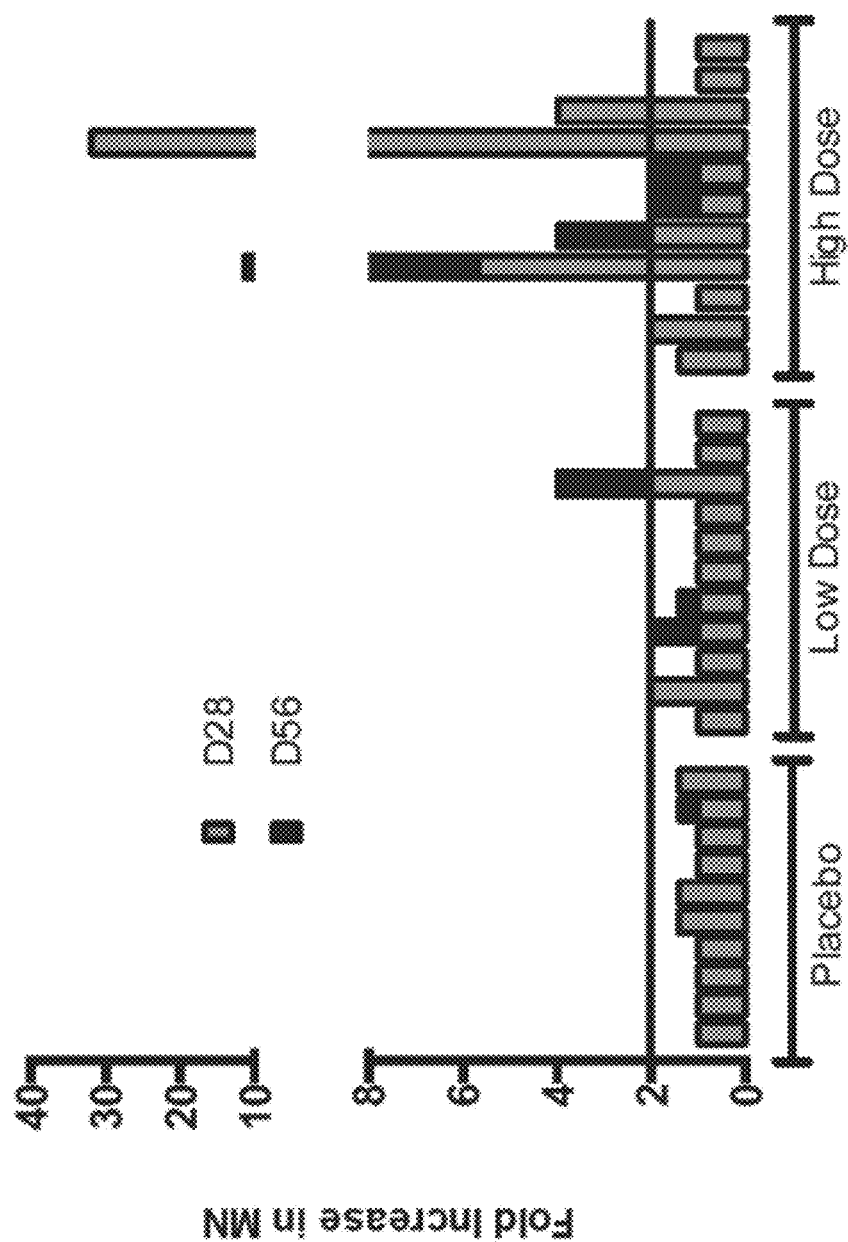
FIG. 6. Fold increase in MN titers for individual subjects. The dark shaded columns indicate where the titers rose between days 28 and 56, whereas the light shaded columns shows the response after the initial immunization. A line was drawn at two fold increases in MN to show which subjects had a detectable neutralizing antibody response. No subject in the placebo group responded, whereas 3 subjects in the low dose and 7 subjects in the high dose group had a 2 fold or greater neutralizing antibody response to influenza after immunization. Placebo N=10, Low Dose and High Dose N=11.

Neutralizing antibody responses to influenza were measured by MN assay. Results show a dose dependent increase in the MN titers in the treated groups versus the placebo control (FIG. 6). The frequency of MN responders with at least a 2-fold increase in the high dose group was significantly different than the placebo group (P=0.003 by Fisher's exact test), whereas the low dose trended higher, but was not significantly higher than placebo (P=0.2). After removing subjects that had MN titers greater than 40, the geometric mean titers (GMT) were calculated in the remaining subjects (Table 2). Day 56 Geometric Fold Titer Response (GMFR) was also calculated (Table 2). These results show that neutralizing antibody titers to influenza are being generated by oral immunization, with a greater than 3 fold increase in the GMT after immunization in the high dose group. These results show that L 100 coated tablets can be used for vaccine delivery to the intestine.

TABLE 2

GMT changes in MN titers for subjects with MN ≤40

| Group | N | GMT D 0 | GMT D 28 | GMT D 56 | GMFR |
|---|---|---|---|---|---|
| Placebo | 8 | 14.1 | 14.1 | 14.1 | 1 |
| Low Dose | 10 | 12.3 | 14.1 | 16.2 | 1.3 |
| High Dose | 7 | 15.6 | 36.2 | 53.8 | 3.4 |

Example 4

We tested parameters for enteric coatings in vitro to determine dissolution times with varying pH and coating percentage. The data provide guidelines for ileal delivery following gastric exposure at low pH (as in the stomach) and subsequent transit through an increasing pH gradient (as is found in the duodenum and jejunum) prior to reaching the ileum.

Tablet disintegration was tested with 150 mg tablets, prepared as described above, and coated with 8, 10, or 12% total solids weight gain, utilizing Eudragit® L100, Eudragit® L100-55, or 1:1 (w/w) mixture of L100 and L100-55 polymers, applied as an organic solvent suspension. In duplicate, tablets prepared with each coating polymer, and at each level of coating application, were pre-exposed to USP simulated gastric fluid (SGF, pH 1.6, no pepsin) for 120 minutes in a VanKel Bio-Dis III reciprocating cylinder dissolution test apparatus at 37° C. at a reciprocation rate of 10 dips per minute (DPM). The tablets were then transferred to USP simulated intestinal fluid (SIF, pH 6.8, no pancreatin). Tablets were observed for disintegration and the time to complete disintegration of both tablets was recorded to the nearest 5 minutes. The data indicate that disintegration time is influenced by both polymer composition and thickness and provide guidance with regard to proper selection of coating composition to influence the behavior of the coatings after tablets exit the stomach.

| Coating | Time to disintegrate at indicated coating level (minutes) | | |
|---|---|---|---|
| Polymer | 8% | 10% | 12% |
| L100 | 20 | 30 | 45 |
| L100/L100-55 | 15 | 20 | 30 |
| L100-55 | 10 | 20 | 25 |

The effect of pH on disintegration time was tested with 150 mg tablets, coated to 10% total solids weight gain with either Eudragit® L100 or Eudragit® L100-55. A series of buffers were prepared by adjusting the pH of USP SIF (no pancreatin) to values encompassing the USP specification of 6.8. Tablets were pre-exposed to USP SGF (ho pepsin) for 120 minutes 37° C. and 10 DPM, then transferred to the pH-modified USP SIF solutions: The tablets were observed for disintegration and the time to complete disintegration was recorded to the nearest 5 minutes. The data indicate that the rate of disintegration is influenced by the environmental pH and differs between the two polymers. Again, the results can be used for proper selection of a coating composition to accomplish drug retention through the stomach and upper small intestine.

| | Time to disintegrate for polymer at pH (minutes) | |
|---|---|---|
| pH of SIF | Eudragit L100 | Eudragit L100-55 |
| 5.4 | 250 | 145 |
| 6 | 110 | 60 |
| 6.4 | 55 | 45 |
| 7 | 30 | 20 |

Example 5

We carried out a Phase 1, sequentially enrolled study, with a randomized and placebo-controlled cohort to evaluate safety, and immunogenicity of a recombinant Ad serotype 5 (rAd5) based oral vaccine against H1 seasonal influenza. Tablets containing the vaccine were coated as described herein to dissolve in the ileum. The data show that an oral tablet vaccine would be competitive with existing vaccines in terms of eliciting neutralizing antibody responses to influenza.

Figure 7A:
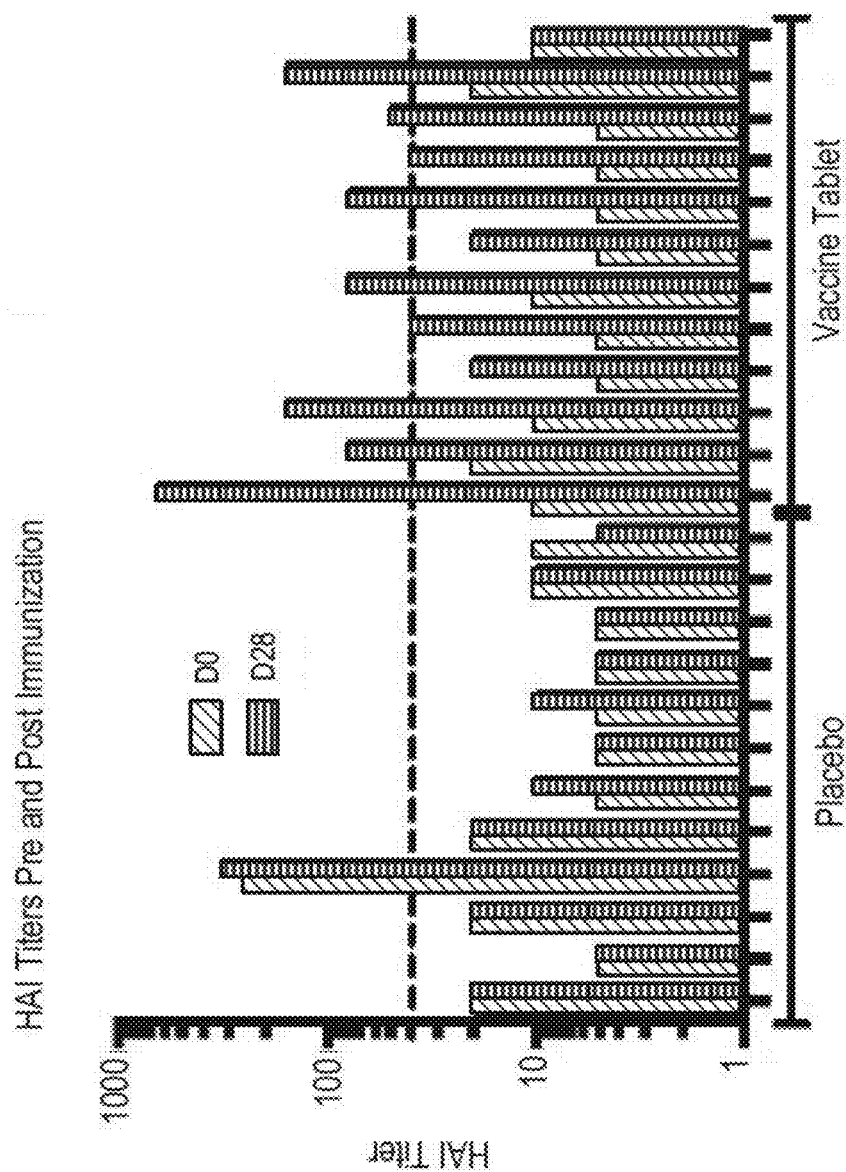
FIG. 7A-7D. Antibody responses following a single oral immunization.

Hemagglutination Inhibition (HAI) responses were measured on days 0 and 28 (FIG. 7A). No placebo treated subject seroconverted, but one placebo subject slipped through screening and had a high day 0 value. None of the vaccine subjects had a starting HAI titer >20. After immunization, nine subjects in the vaccine group reached seroprotective levels (HAI 240) (FIG. 7A). The Geometric Mean Titer (GMT) for the group was 61.1 (95% CI: 30-124), a 7.7-fold geometric mean fold rise (GMFR) over the initial GMT of 7.9 (95% CI: 6-11). Of the eleven 4-fold risers (92%), nine seroconverted (SC) with the other 2 subjects showing a 4-fold increase in HAI titer from 5 to 20. The vaccine group had a statistically significant increase in the number of 4-fold responders versus placebo (11 versus 0, with P<0.0000 by Fisher's Exact Test). The placebo subjects had a GMT of 11.9 (95% CI: 6-25) on day 28 versus a GMT of 11.0 on day 0 (95% CI: 5-23).

Durability of the antibody response was measured by examining HAI responses 180 days after immunization. In the vaccine-immunized group, 75% (9 of 12) of the subjects were seroprotected on day 28 and 75% (9 of 12) were still seroprotected on day 180. The HAI GMT were plotted (FIG. 7B), and the decrease in the GMT was found to be 28% between 28 and 180 days post immunization.

Figure 7B:
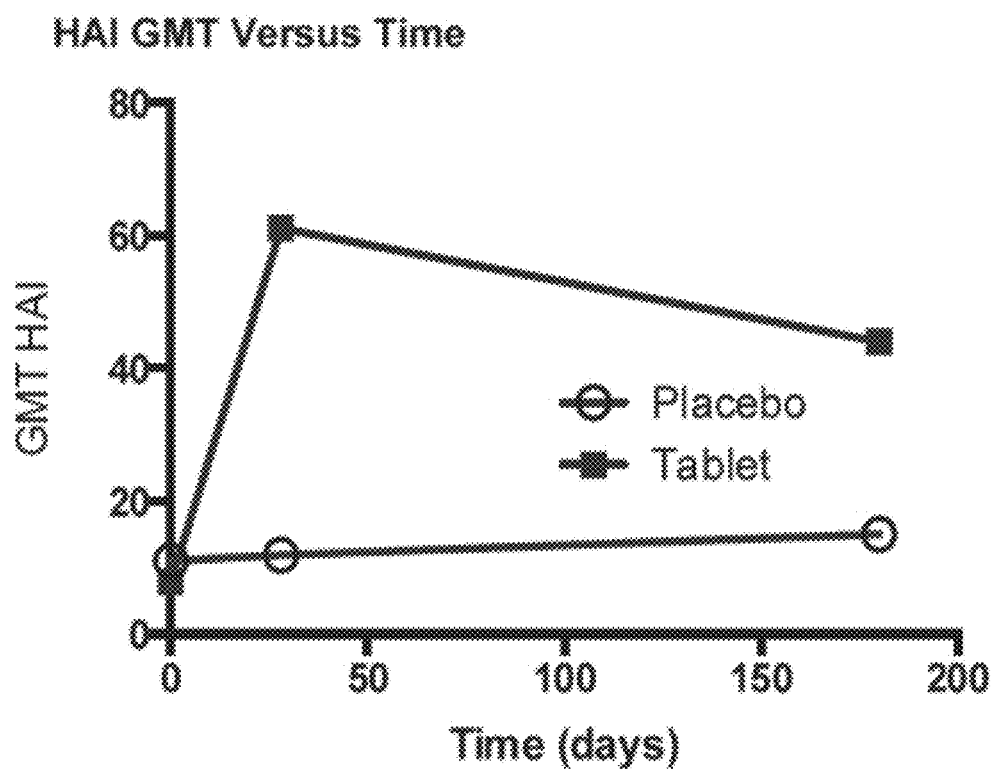
Figure 7C:
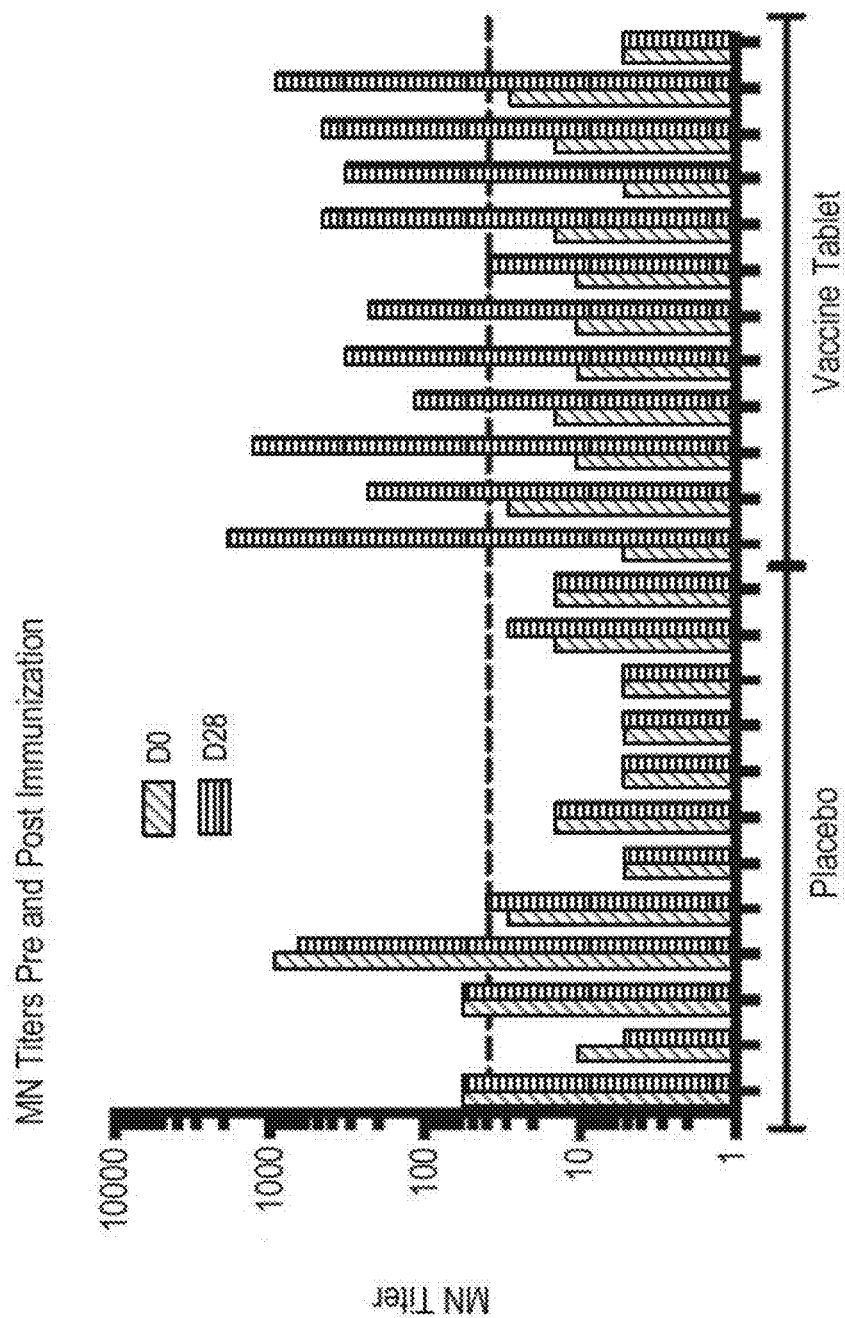

Neutralizing antibody responses to influenza were measured by MN assay. Significant increases in the MN titers in the treated group versus the placebo control were observed (FIG. 7C). The frequency of 4-fold MN responders in the vaccine treated group was significantly different than the placebo group, with 11 subjects responding in the vaccine treated group versus 0 in the placebo group (P<0.0000 by Fisher's exact test).

After removing subjects that had baseline MN titers (and HAI titers) greater than 40, the geometric mean titers (GMT) were calculated in the remaining subjects on days 0 and 28 as shown in the following table. The GMT for the vaccine group rose to 247 (95 CI: 89 685) versus no rise in the placebo for a day 28 GMT of 9.6 (95 CI: 5-18). These calculations had no impact on the vaccine group, as none of the subjects had high initial MN or HAI titers. These results show that neutralizing antibody titers to influenza are generated by oral immunization, with a greater than 20-fold increase in the GMT after immunization in the vaccine-treated group.

TABLE 3

GMT changes in HAI and MN titers for subjects with MN ≤40.

| ASSAY | GROUP | N | GMT D 0 | GMT D 28 | GMFR | SC |
|---|---|---|---|---|---|---|
| HAI | Placebo | 11 | 8.3 | 8.8 | 1.1 | 0% |
|  | Vaccine | 12 | 7.9 | 61.1 | 7.7 | 75% |
| MN | Placebo | 9 | 9.3 | 9.6 | 1.0 | N/A |
|  | Vaccine | 12 | 8.6 | 247 | 29 | N/A |

Figure 7D:
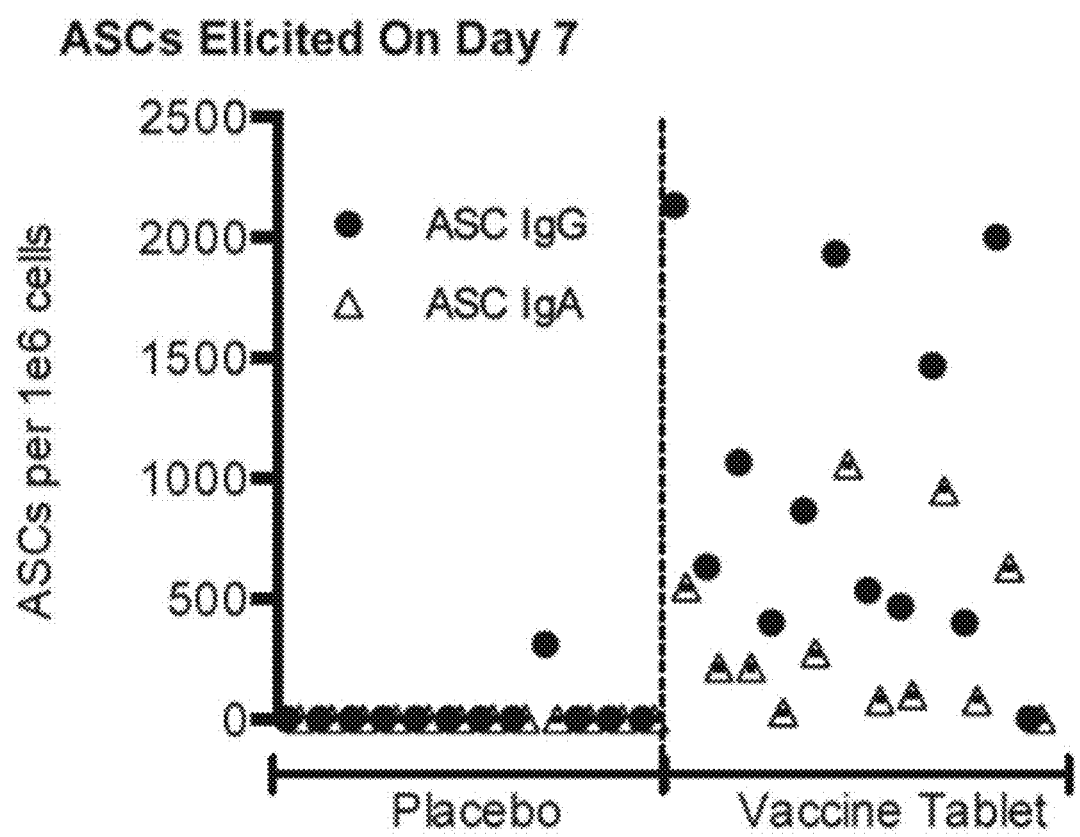

In order to measure total antibody responses to HA, the numbers of circulating pre-plasma B cells in peripheral blood were measured by ASC assay on days 0 and 7 after immunization. Results show that ASCs could be reliably measured on day 7 in the vaccine-treated group (FIG. 7D). Background ASCs were generally negligible on day 0. For the vaccine treated group, an average of 992 (+/−std err 209, 95% CI: 532-1452) IgG ASCs and 337 IgA ASCs (+/−std err 104, 95% CI: 117-580) each per $1 \times 10^6$ PBMC were found for day 7, with only one subject out of 12 having no detectable ASC response. The placebo group had no IgA spots on day 7, but one subject had a high background smear and a measurable IgG ASC response with smaller spots than normally observed. The treated group was significantly different than placebo in terms of the ability to elicit an IgG or an IgA ASC response at day 7 (P=0.0007 and P=0.008 respectively by T Test).

Subjects were retrospectively measured for their anti-vector titers pre- and post-immunization. Following oral immunization, a few vaccine-treated subjects had an increase in neutralizing antibody responses to Ad5, which led to a 2.6-fold increase in the GM neutralizing antibody titers, compared to 1.0-fold GM fold rise in the placebo treated subjects. In the vaccine group, HAI and MN responses trended similarly for individual subjects. Eight subjects were Ad5 negative before immunization, and four were Ad5 positive before immunization. One subject that was Ad5 positive did not HAI seroconvert, however, one subject that was Ad5 positive had the highest increase in HAI titers (64 fold) of any of the subjects in the study. This same subject had a gain in MN titers of 362 fold without any increase in the Ad5 neutralizing antibody titers pre and post immunization. There was no observed correlation between starting Ad5 titers versus fold MN response (or HAI response) for the subjects immunized with the tablet vaccine.

Moreover, the presently disclosed tablet vaccine is stable at room temperature for greater than 270 days and can tolerate short-term excursions at higher temperatures, which makes this approach technically feasible.

Example 5 Discussion

The US military conducted an independent study to measure the effects of their seasonal vaccine campaigns on neutralizing antibody responses in military personnel, and reported a MN Titer GMFR of 5.6 after trivalent inactivated vaccine (TIV) injection and a GMFR of 2.2 following live-attenuated influenza vaccine (LAIV) intranasal administration, after accounting for subjects that had MN titers above 40 to start (Faix et al. (2012) *PloS one* 7:e34581). In another study, the SC rate to H1N1 was found to be 45% for one injection of 45 ug of HA protein (without adjuvant) (Gordon et al. (2012) *Vaccine* 30:5407), while in another, the H1N1 vaccine was highly immunogenic with a 78% SC rate observed after 1 dose of a split vaccine (Greenberg et al. (2009) 361:2405).

In contrast to the variable results observed with injected vaccines, in the present study, MN GMFR was calculated at 29 for the 12 vaccine treated subjects with 92% of subjects showing a greater than 4-fold rise in MN titers. In the present tablet study, the HAI SC rate among vaccine treated subjects was 75% with over 92% of subjects having a 4-fold rise in HAI titers (FIG. 7A). MN titers were higher than the HAI titers. It is possible that the MN assay is more sensitive or that the oral rAd based vaccine elicits stronger neutralizing responses outside the head region than protein injected vaccines.

HAI responses are elicited with injected commercial vaccines, but HAI titers are known to wane. For example, non-HIV infected volunteers had a 67% drop in GMT HAI titers between 1 and 6 months post immunization (Crum-Cianflone et al. (2011) *Vaccine* 29:3183). Similarly, the percentage of seroprotected subjects dropped from 75% to 56% for HIV negative subjects that enrolled with seronegative HAI titers (≤1:10). Studies with pandemic influenza vaccines have also shown decreases in durability. In the AS03 avian influenza vaccine study, the GMT reached 563 after 2 vaccine doses, but at 6 months post immunization, the GMT had dropped to 18, a 96% decrease (Leroux-Roels et al. (2010) *Vaccine* 28:849). In the present tablet vaccine study, the percentage of seroprotected subjects remained constant at 75% at 1 and 6 months post immunization, and the HAI GMT titer drop was less dramatic showing only a 28% decrease (FIG. 7B). One possibility is that the durability is better for vector-based vaccines because of enhanced T cell responses.

Example 5 Materials and Methods

Clinical protocol and enrollment. Subjects were pre-screened for Hemagglutination Inhibition (HAI) titers within 45 days of enrollment. In order to be eligible for study participation subjects had to have an initial HAI titer of ≤1:20, be between 18-49 years of age, and be in good health. The active phase of the trial was through day 28, with the follow-up phase for monitoring safety to continue for 1 year.

24 subjects were enrolled. All subjects that enrolled completed safety and immunogenicity assessments through the active phase, and through day 180 of the monitoring phase.

Randomization and Masking. The study was designed to evaluate the vaccine (VXA-A1.1) in 12 subjects at a single dose of $1\times10^{11}$ infectious units (IU) with 12 subjects given a placebo control. There were 3 sequentially enrolled sentinel vaccine-treated subjects, with each subject dosed no more frequently than one every 24 h After a week of monitoring for vaccine-related toxicities, the remaining subjects in the treated cohort (9) were randomized along with 12 placebo controls. Randomization was performed by computer generated assignment, and study drug was distributed with concealed identity to the blinded staff by the unblinded pharmacist. All investigative site staff as well as persons directly involved with immunological assays or the assessment of clinical safety remained blind to treatment assignments. All subjects were blinded in the study.

Vaccine. The rAd vector (non-replicating Ad5) carries DNA which encodes the HA (A/CA/04/2009) transgene whose expression is driven by a CMV promoter and a molecular dsRNA hairpin driven by a separate promoter. GMP drug substance was produced in Wave bags (GE Healthcare, Waukesha, Wis.) at Lonza Biologicals (Houston, Tex.). Purification was performed by ion exchange chromatography, followed by buffer exchange. Purified vector was mixed with excipients, lyophilized, and then tableted at Lonza using microcrystalline cellulose and starch as tableting bulk. Tablets were enteric coated with Eudragit L100® (Evonik Industries, Darmstadt, Germany) using a Vector Hi-Coater system (Vector Freund, Cedar Rapids, Iowa). The final product was released in one lot, and titered by standard IU assay at Lonza. Placebo was prepared as similarly sized and shaped tablets containing 150 mg of microcrystalline cellulose, without enteric coating.

Endpoints. The primary endpoint for this study is safety and the secondary endpoint is immunogenicity through the active phase, primarily by HAI titers and HAI seroconversions. Additional immunological endpoints include MN titers and ASCs. There were 5 adverse events in the placebo group and 4 in the vaccine group, all of which wore grade 1 in severity. There were no serious adverse events reported in the study.

PBMC isolation and cryopreservation. Blood was collected in $K_3$ EDTA Vacutainer® tubes (BD, Franklin Lakes, N.J.) and PBMCs were isolated the same day using Lymphoprep™ tubes (Axis-Shield, Norway). PBMCs were frozen and thawed using serum free reagents according to the manufacturer's instructions (Cellular Technology Ltd [CTL], Shaker Heights, Ohio).

Antibody Secreting cells (ASCs). Enzyme linked immunosorbent (ELISpot) kits for IgG and IgA secreting B cells were performed according to manufacturer's instructions (Mabtech, Mariemont, Ohio). Cells were cultured (between $1.5\times10^4$ to $5\times10^5$ cells per well) in triplicate wells, in CTL-Test medium to optimize spots. HA protein (Protein Sciences Corp, Meriden, Conn.) was biotinylated and quantitated using a biotinylation kit (Pierce, Rockford, Ill.).

Antibody assays. HAI and Microneutralizing (MN) Titers were performed and were measured against MDCK derived A/CA/07/2009 and egg derived A/CA/07/2009 respectively. HAI and MN titers less than 10 were marked as 5 as suggested by regulatory advice.

Statistical analysis. Unpaired Students "t" tests were performed to test for significant differences between groups. A two-tailed Fisher's Exact test was used to determine if the observed frequencies were different for some analyses, as stated in the text. For both tests, p values of ≤0.05 were considered significant 95 percent confidence intervals (95 CI) were provided for measured values.

Example 6

Nonclinical Studies of a Norovirus Vaccine.
Introduction

The norovirus VP1 vaccines (VXA-G2.4-NS and VXA-G1.1-NN) of the invention has the same replication-defective viral vector backbone and adjuvant RNA sequence as described in U.S. Pat. No. 8,222,224 and Scallan et al. Clinical and Vaccine Immunology 2013; 20(1): 85-94. The sequence of the vector backbone is provided in SEQ ID NO: 7.

VXA-G2.4-NS is an E1/E3-deleted replication-incompetent serotype 5 adenovirus vector designed for use as a vaccine for the prevention of norovirus disease (NVD). The recombinant adenovirus (rAd) vector codes for a 1.6 kb gene from the viral protein 1 (VP1) of norovirus (G2.4 Sydney strain) and an adjuvant dsRNA sequence that enhances the immunogenicity of the expressed antigen in the gut mucosa via its TLR3 agonistic activity. The VP1 gene has been codon-optimized for expression in mammalian cells and is expressed using a human cytomegalovirus intermediate early region (hCMVIE) enhancer/promoter and a bovine growth hormone polyadenylation (pA) signal. This expression cassette also includes the first introit of human β-globin to enhance transgene expression. A second hCMVIE promoter is used to express the adjuvant RNA sequence. The adjuvant sequence is derived from a luciferase sequence and has been reported to stimulate the induction of type I interferon in vitro (2). The adjuvant is expressed as a short hairpin RNA, comprising a 21-nucleotide sequence (GAAACGATATGGGCTGAATAC) SEQ ID NO: 11 as a tandem sequence in forward and reverse orientations separated by six nucleotides that comprise the loop of the RNA The 21-nucleotide forward and reverse RNA sequences anneal to form the stem of the loop. This adjuvant cassette utilizes a synthetic poly A (SPA).

As described below, preclinical studies in mice and ferrets show that vaccination with VXA-G2.4-NS (and the related VXA-G1.1-NN) elicited substantial and reliable antibody responses in both systemic serum IgG and intestinal (fecal) IgA response in test animals. A unique immune response elicited by oral vaccination is the induction of antibodies derived from local sources of B cells. After oral vaccination or enteric infection, B cells residing in the lamina propria (underneath the gut epithelial cells) predominantly produce dimeric antibodies of the IgA isotype. IgA antibodies pass across the gut epithelial cells into the lumen through facilitated transport, leaving a secretory component attached to dimeric IgA. The resulting molecule is known as secretory IgA or SIgA. SIgA serve as an additional external barrier to block enteric infection. SIgA are eventually flushed out of the system, and can be detected in fecal samples.

Nonclinical Pharmacology
Introduction

Figure 8:
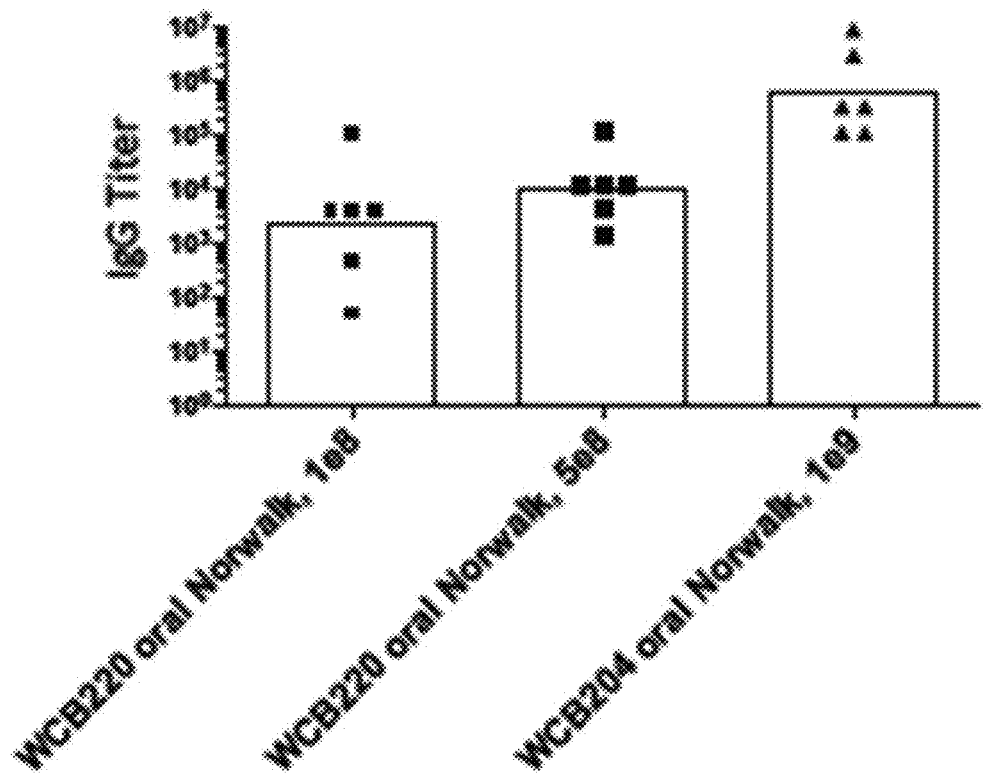
FIG. 8. Serum ELISA IgG Titers Versus Dose of VXA-G1.1-NN in mice. Mice were immunized with VXA-G1.1 NN of 1×108, 5×108 and 1×109. VXA-G1.1-NN was delivered orally by gavage on days 0 and 28. The serum IgG responses against Norwalk VP1 were measure by ELISA at week 8. N=6. Each icon represents an individual mouse. The top of the bar for each study indicates the GMT. As the dose was increased from 1×108 to 5×108 to 1×109, the serum VP1 IgG titer showed a dose-dependent increase from 2×103 to 1×104 to 5×105.
Figure 9:
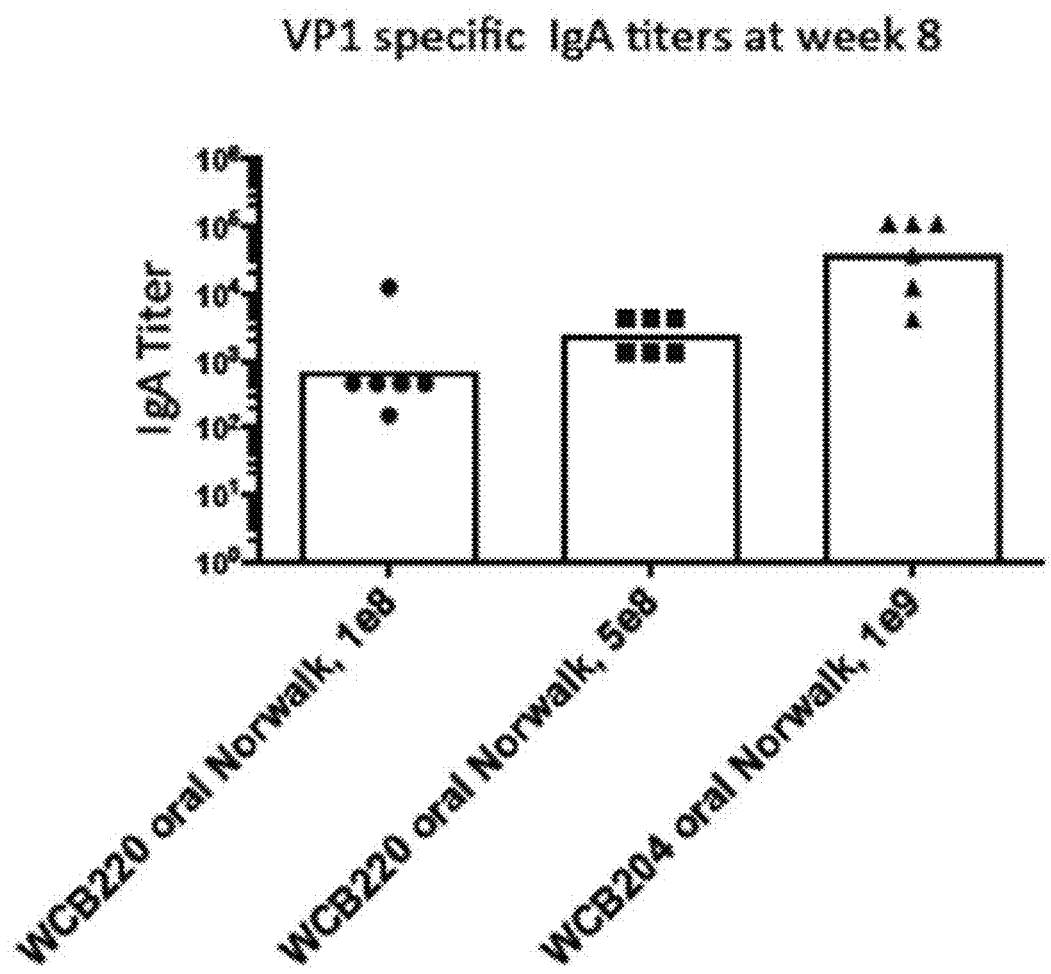
FIG. 9. Fecal SIgA ELISA Titers Versus Dose of VXA-G1.1-NN in mice. Mice were immunized with VXA-G1.1-NN of 1×108, 5×108 and 1×109. VXA-G1.1-NN was delivered orally by gavage on days 0 and 28. The fecal SIgA responses against Norwalk VP1 were measure by ELISA at week 8. Each study has a total of 6 mice. Each icon represents an individual mouse. The top of the bar for each study indicates the GMT. As the dose was increased from 1×108 to 5×108 to 1×109, the fecal VP1 sIgA titer showed a dose-dependent increase from 1×103 to 2×103 to 3×104.
Figure 10:
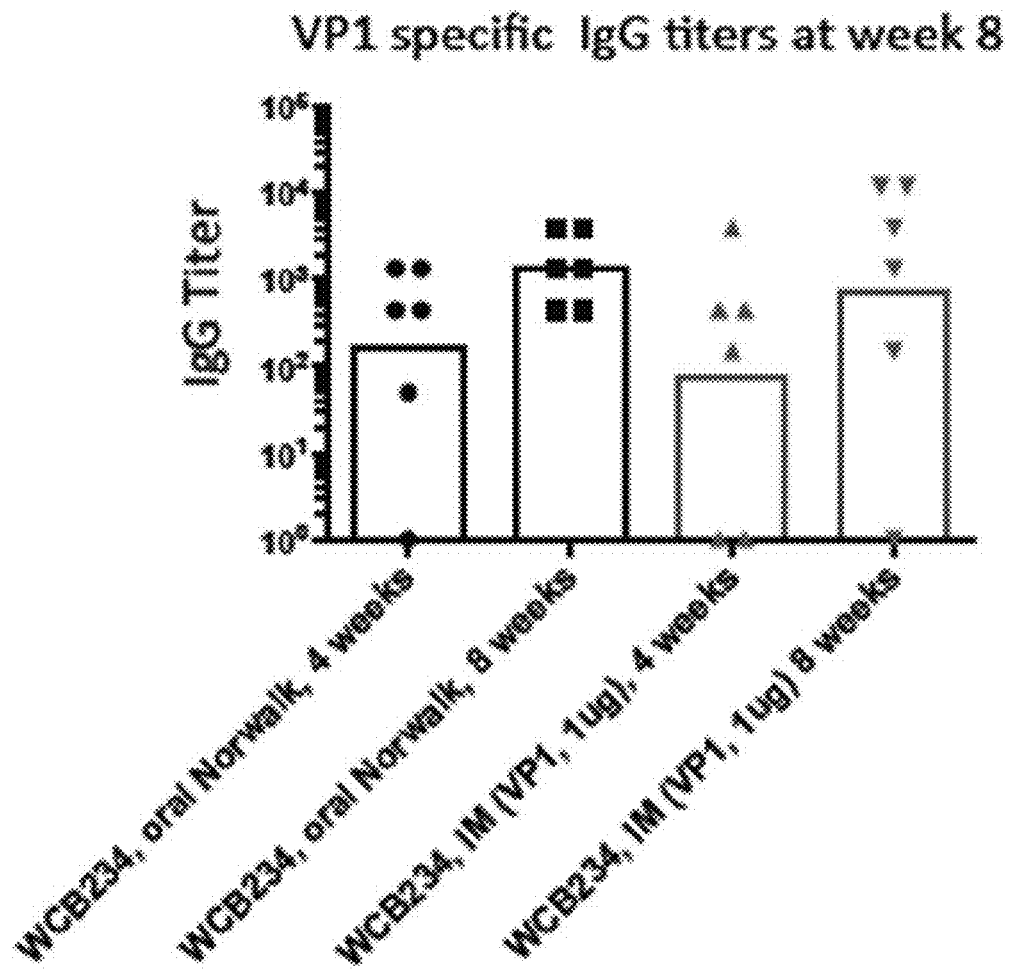
FIG. 10. Serum ELISA IgG Titers of VXA-G1.1 NN Versus VP1 protein in mice. Mice were immunized with VXA-G1.1 NN of 1×108 orally or Norwalk virus VP1 protein (1 ug) intramuscularly on days 0 and 28. The serum IgG responses against Norwalk VP1 were measured by ELISA at weeks 4 and 8. Each study has a total of 6 mice. Each icon represents an individual mouse. The top of the bar for each study indicates the geomean titer. Oral vaccine generated slightly higher serum IgG titer values than the i.m. protein vaccine.
Figure 11:
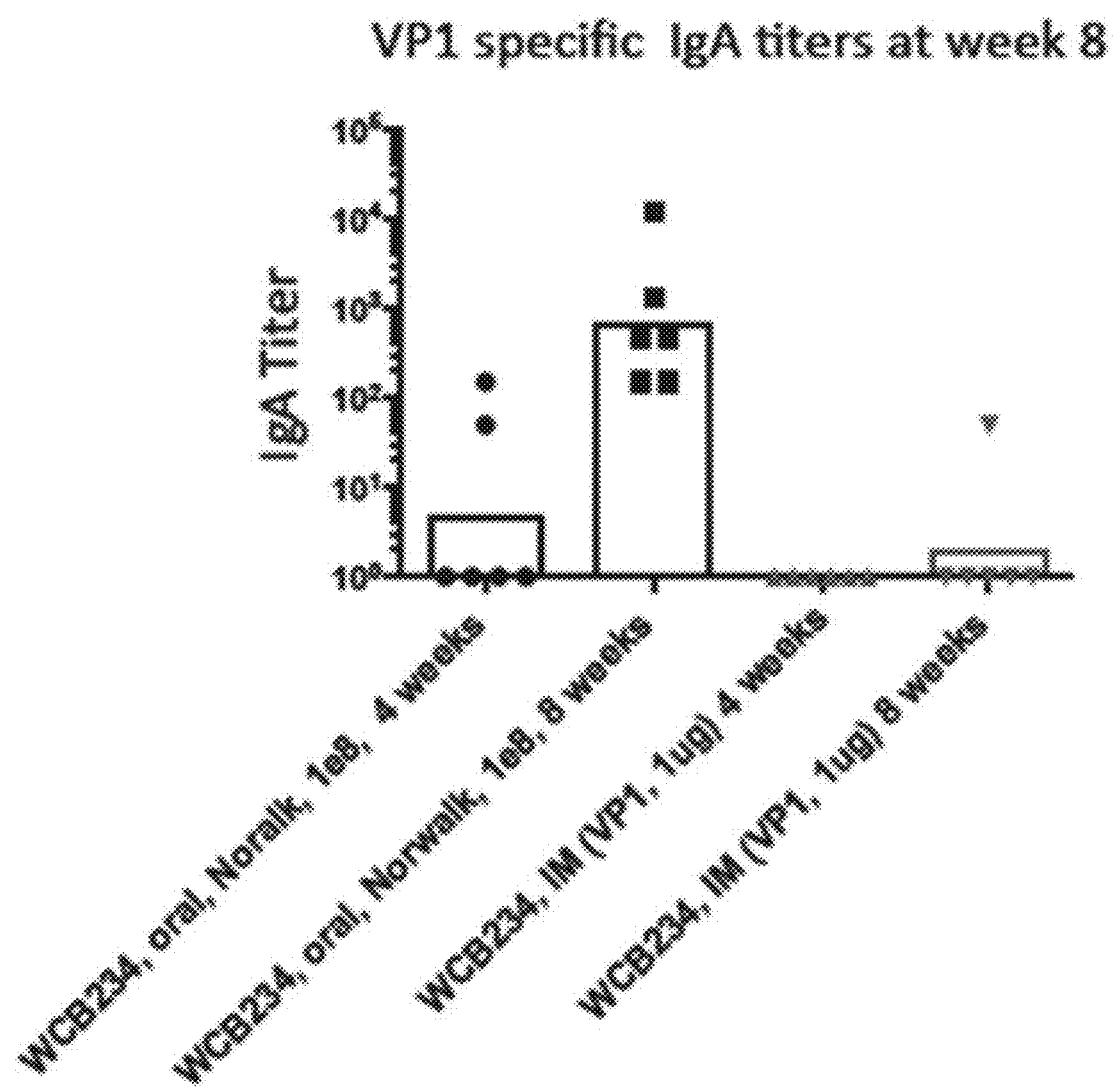
FIG. 11. Fecal SIgA ELISA Titers Versus Dose of VXA-G1.1-NN in mice. Mice were immunized with VXA-G1.1-NN of 1×108 orally or Norwalk virus VP1 protein (1 ug) intramuscularly on days 0 and 28. The fecal IgA responses against Norwalk VP1 were measure by ELISA at weeks 4 and 8. Each study has a total of 6 mice. Each icon represents an individual mouse. The top of the bar for each study indicates the geomean titer. The oral vaccine generated a dramatically higher fecal IgA immune response than the i.m. protein vaccine.
Figure 12:
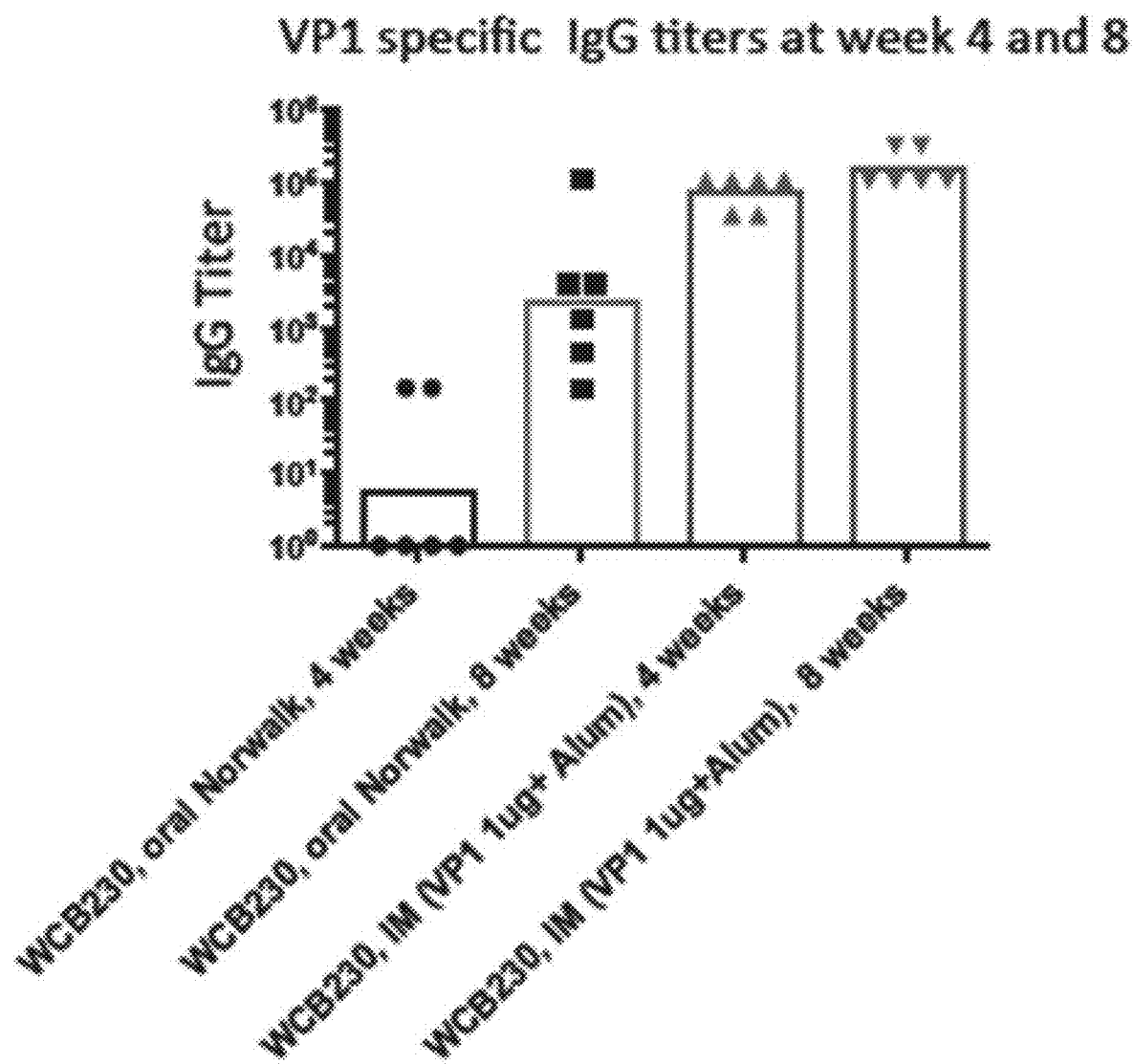
FIG. 12. Oral immunization of VXA-G1.1-NN compared to VP1 protein immunization for Serum ELISA Titers. Mice were immunized with VXA-G1.1-NN of 1×108 orally or Norwalk virus VP1 protein (1 ug) in the presence of adjuvant, aluminium hydroxide intramuscularly on days 0 and 28. The serum IgG responses against Norwalk VP1 were measure by ELISA at weeks 4 and 8. Each study has a total of 6 mice. Each icon represents an individual mouse. The top of the bar for each study indicates the geomean titer. Intramuscular injection with the VP1 protein together with alum generated much higher serum titer.
Figure 13:
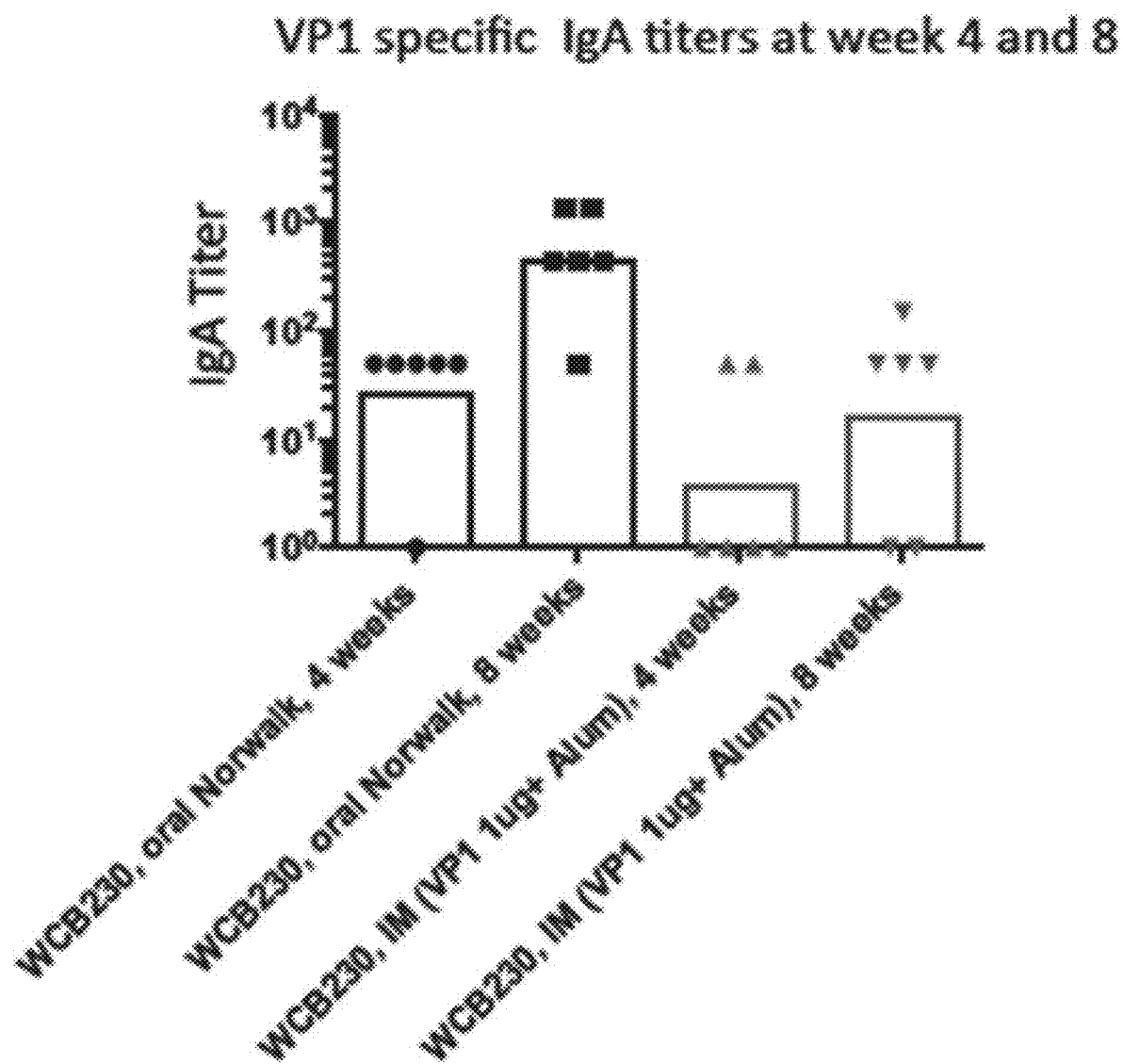
FIG. 13. Oral immunization of VXA-G1.1-NN compared to VP1 protein immunization for Fecal SIgA ELISA Titers Mice were immunized with VXA-G1.1-NN of 1×108 orally or Norwalk virus VP1 protein (1 ug) in the presence of adjuvant, aluminium hydroxide intramuscularly on days 0 and 28. The fecal IgA responses against Norwalk VP1 were measure by ELISA at weeks 4 and 8. Each study has a total of 6 mice. Each icon represents an individual mouse. The top of the bar for each study indicates the geomean titer. Even in the presence of adjuvant, aluminium hydroxide, the oral vaccine generated a higher fecal SIgA immune response than the i.m. protein vaccine.
Figure 14B:
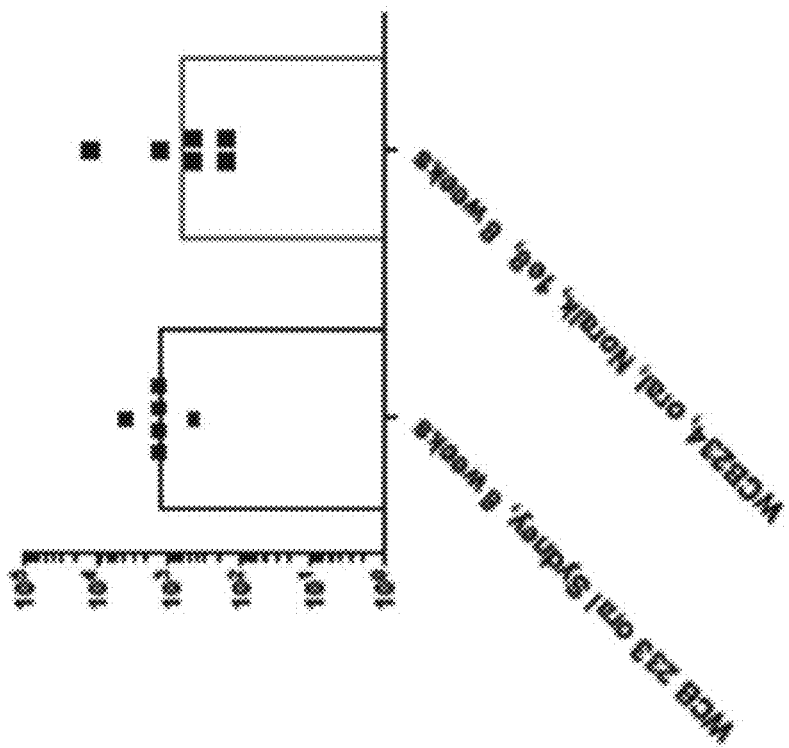
FIG. 14A-14B. Serum and Fecal IgA Titers following Oral Immunization of VXA-G2.4-NS in mice. Mice were immunized with VXA-G2.4-NS of 1×108 orally on days 0 and 28. For comparison, oral delivered groups from study #3 were presented again. The serum IgG responses against Sydney VP1 were measure by ELISA at weeks 4 and 8—FIG. 14A. The fecal SIgA response against the Sydney VP1 was measured by ELISA at week 8 FIG. 14B. At 4 weeks, the Sydney strain vaccine generated better IgG titer values than the Norwalk vaccine. In addition, even at 4 weeks the titer values from the Sydney strain were slightly higher than the Norwalk values at 8 weeks (A). The Sydney vaccine generated slightly higher fecal VP1. IgA titer values than the Norwalk vaccine.
Figure 14A:
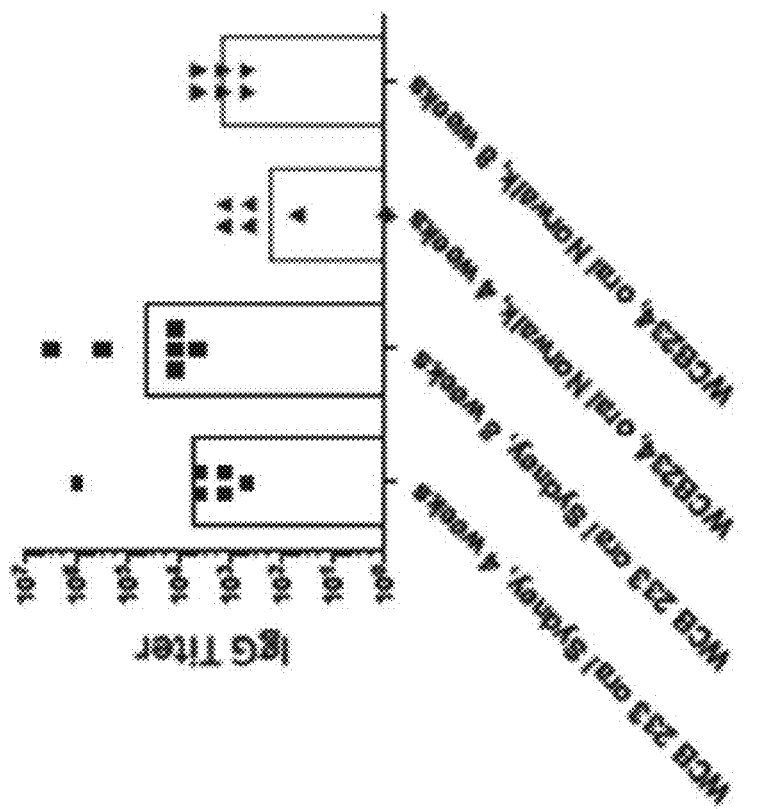
Figure 15B:
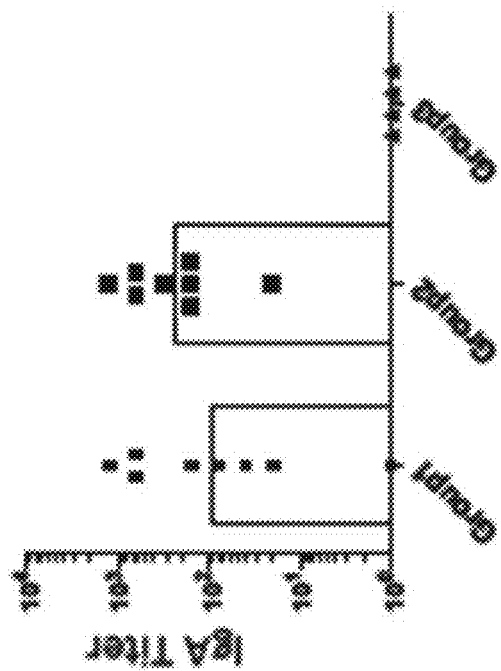
FIG. 15A-15B. Serum and Fecal IgA Titers following Oral Immunization of VXA-G2.4-NS in ferrets. Ferrets were endoscopically administered VXA-G2.4-NS on days 0 and 2 (group1) or days 0 and 28 (group2). Ferrets in group3 were intramuscularly administered the recombinant VP1 protein from the Sydney strain norovirus on days 0 and 28. Whereas group1 generated higher IgG titer values than group2, group2 generated higher SIgA titer values than group1. Group3 failed to generate fecal SIgA response although serum IgG responses were generated.
Figure 15A:
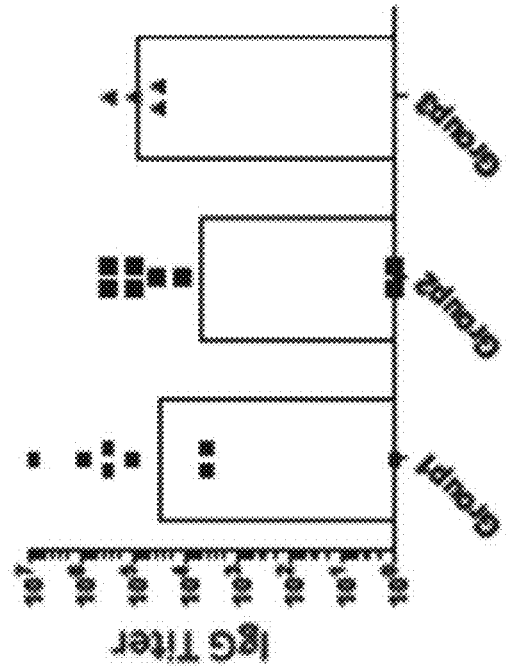
Figure 16:
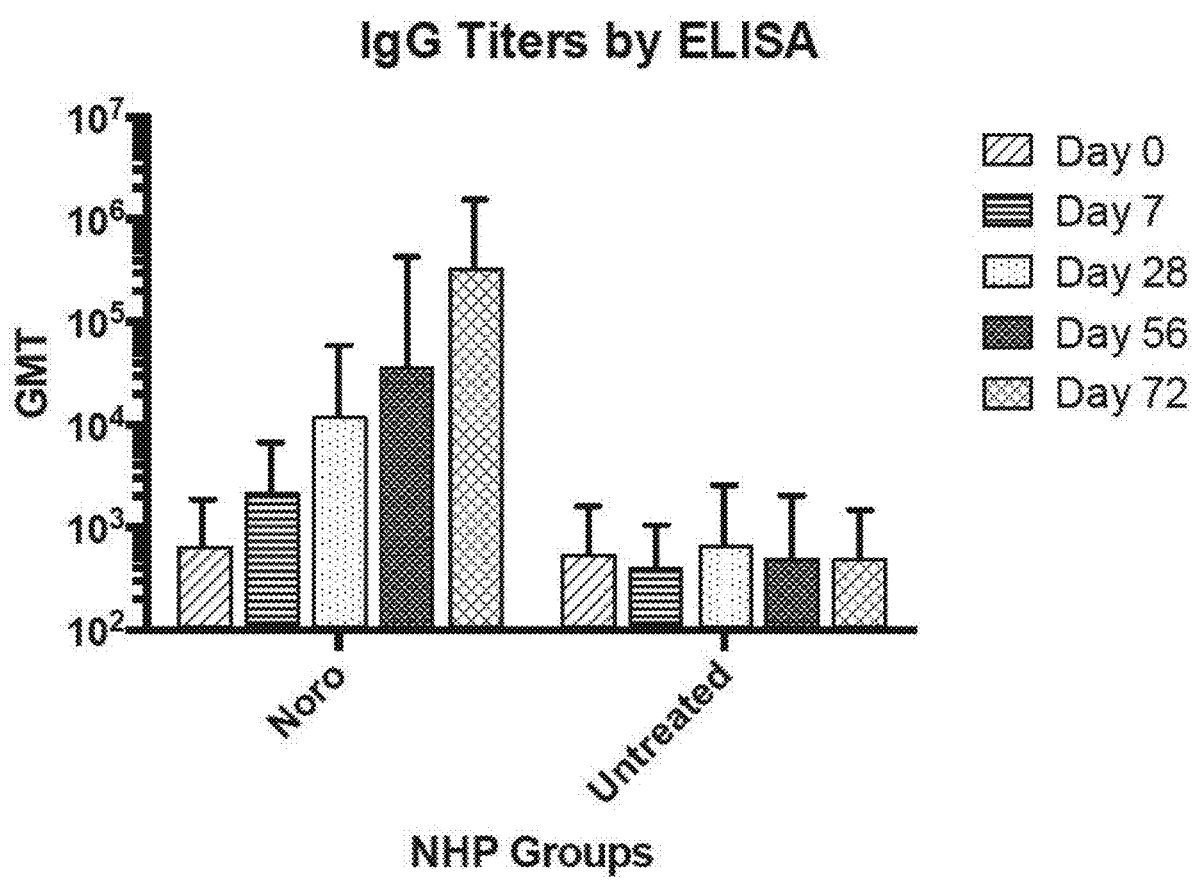
FIG. 16. Serum IgG following Oral Immunization of VXA-G2.4-NS in Non human primates (NHP, Cynomolgous macaque). NHPs were endoscopically administered VXA-G2.4-NS on days 0 and 56 (the "Nord" group). Serum IgG titers were measured by ELISA at day 0, 7, 28, 56, and 72.

The primary objective of the immunogenicity studies was to demonstrate that oral adenoviral constructs that express VP1 from two different norovirus species could elicit intestinal specific SIgA as well as serum IgG immune responses against norovirus antigen (VP1) following oral immunization of norovirus vaccine.

The secondary objective of the immunogenicity studies was to compare two routes of immunization (oral with VXA-G2.4-NS vs. i.m. with VP1 protein). The VP1 protein was compared since VP1 VLP based injectable vaccine is one of the few norovirus vaccines under development. Generally, SIgA are induced by mucosal immunization but a much lesser degree by parenteral immunization. Therefore, we investigated intestinal SIgA response induced by oral VXA-02.4-NS delivery compared to injectable recombinant VP1 protein based vaccines.

TABLE 4

| Nonclinical Pharmacology Studies | | | | | |
|---|---|---|---|---|---|
| Study Title (Study No.) | Animal Model (Species, Gender, No.) | Therapy (Treatment) | VXA-G2.4-NS (Immunization schedule) | Endpoints (Sample collection time points) | Endpoints (Assays) |
| IMMUNOGENICITY STUDY | | | | | |
| Immunogenicity study of Ad-dsRNA-CMV-VP1 (Norwalk) vaccine | | | | | |
| Study No. | | | | | |
| (1) | Balb/c mice. 6 F per group | Group 1: oral VXA-G1.1-NN ($1 \times 10^8$ IU[a]) Group 2: oral VXA-G1.1-NN ($5 \times 10^8$ IU[a]) | Immunization on days 0 and 28 | 8 weeks | VP1 ELISA (serum IgG and fecal IgA) |
| (2) | Balb/c mice. 6 F per group | VXA-G1.1-NN: oral ($1 \times 10^9$ IU[a]) | Immunization on days 0 and 28 | 8 weeks | VP1 ELISA (serum IgG and fecal IgA) |
| (3) | Balb/c mice. 6 F per group | Group 1: oral VXA-G1.1-NN ($1 \times 10^8$ IU[a]) Group 2: i.m. VP1 protein from Norwalk virus (1 ug) | Immunization on days 0 and 28 | 4 and 8 weeks | VP1 ELISA (serum IgG and fecal IgA) |
| (4) | Balb/c mice. 6 F per group | Group 1: oral VXA-G1.1-NN ($1 \times 10^8$ IU[a]) Group 2: i.m. VP1 protein from Norwalk virus (1 ug) + Alum | Immunization on days 0 and 28 | 4 and 8 weeks | VP1 ELISA (serum IgG and fecal IgA) |
| Immunogenicity study of VXA-G2.4-NS (Sydney) vaccine | | | | | |
| (5) | Balb/c mice. 6 F per group | VXA-G2.4-NS: oral ($1 \times 10^8$ IU[a]) | Immunization on days 0 and 28 | 4 and 8 weeks 8 weeks | VP1 ELISA Serum IgG Fecal IgA |
| Immunogenicity study of VXA-G2.4-NS (Sydney) vaccine | | | | | |
| Study | Ferrets 4 M/4 F per group 1 and 2 | Group 1: oral VXA-G2.4-NS ($1 \times 10^9$ IU[a]) | Immunization on days 0 and 28 | 8 weeks | VP1 ELISA (serum IgG and fecal IgA) |
| | | Group 2: oral VXA-G2.4-NS ($1 \times 10^9$ IU[a]) | Immunization on day 0 and 2 | 8 weeks | VP1 ELISA (serum IgG and fecal IgA) |
| | 2 M/2 F per group 3 | Group 3: i.m. VP1 protein from Sydney strain NoV (5 ug) | Immunization on days 0 and 28 | 8 weeks | VP1 ELISA (serum IgG and fecal IgA) |

[a]IU = infectious units

Immunogenicity Studies

The primary objective of the initial mice immunogenicity studies was to determine if the vector backbone expressing a norovirus VP1 from Norwalk virus or the Sydney strain could induce an antibody response to VP1 from Norwalk virus or the Sydney strain as measured by ELISA.

rAd expressing the Norwalk VP2 strain and the dsRNA adjuvant (VXA-G1.1-NN) was delivered orally by gavage on days 0 and 28. A dose titration was conducted (study #1 and study #2). Norwalk virus VP1 specific IgG and sIgA responses were measured from serum and fecal samples, respectively at 8 weeks. As expected, as the dose was increased from $1\times10^8$ to $5\times10^8$ to $1\times10^9$, the serum VP1 IgG titer showed a dose-dependent increase geometric mean titer (GMT) increase from $2\times10^3$ to $1\times10^4$ to $5\times10^3$ (FIG. 8). A similar but slightly more gradual dose dependent increase from $1\times10^3$ to $2\times10^3$ to $3\times10^4$ in fecal VP1 IgA response was also observed (FIG. 9). The mice studies showed that VXA-G1.1 NN vaccine is immunogenic and generated dose dependent serum and fecal VP1 antibody responses.

In the next study (study #3), immune responses via two mutes of administration with oral delivery by gavage with VXA-G1.1-NN (group 1) and intramuscular injection with Norwalk VP1 protein (group 2) were compared (FIGS. 2.2.3 and 2.2.4). Norwalk virus VP1 specific IgG and SIgA responses were measured from serum and fecal samples, respectively at 4 and 8 weeks. The oral vaccine of the invention generated slightly higher serum IgG titer values than the intramuscular protein vaccine (FIG. 10). In the fecal study, oral vaccine generated a dramatically higher intestinal SIgA immune response than the intramuscular protein vaccine (FIG. 11).

A similar study (study #4) was conducted with the Norwalk virus VP1 protein vaccine with a vaccine adjuvant, aluminium hydroxide (FIGS. 12 and 13). Intramuscular injection with the VP1 protein together with alum generated much higher serum titer (FIG. 12). However, the oral vaccine was clearly superior at generating SIgA, as indicated by the higher fecal VP1 specific IgA titer value (FIG. 13). With the presence of alum which is a strong adjuvant, a few animals produced fecal VP1 IgA after intramuscular immunization Whereas fecal VP1 IgA from samples without alum was almost non detectable. The data suggest that the oral vaccine of the invention has an immunological advantage over injectable vaccine to produce intestinal SIgA immune response.

The currently circulating norovirus variant, the Sydney strain vaccine (VXA G2.4-NS), was tested (study #5 FIG. 2.2.7). At 4 weeks, the Sydney strain vaccine generated far better titer values than the Norwalk virus vaccine. In addition, even at 4 weeks the titer value from the Sydney strain vaccine was slightly higher than the Norwalk value at 8 weeks (FIG. 14A). The Sydney strain vaccine generated slightly higher fecal VP1 SIgA titer values than the Norwalk vaccine did (FIG. 14B). The Sydney strain vaccine appears to be more immunogenic. Accordingly, we chose the Sydney strain for the following ferret study:

The objective of the ferret study (study #6) was to (1) determine whether the oral vaccine of the invention could induce an intestinal SIgA as well as systemic serum IgG response compared to recombinant Sydney VP1 protein and (2) compare SIgA and IgG response with two different immunization schedules. Twenty ferrets were randomized into 3 groups (4 males and 4 females in each of groups 1 and 2 and 2 males and 2 females in Group 3). On day 0 and 2, animals in group 1 were endoscopically administered VXA-G2.4-NS. On days 0 and 28 animals in group 2 were endoscopically administered VXA-G2.4-NS and animals in Group3 were intramuscularly administered the Sydney norovirus recombinant VP1 protein. Animals in group 1 produced higher IgG titer value than group 2 (3×104 vs 5×103): Whereas animals in group 2 generated higher SIgA titer values than group 1 (247 vs 92). Similarly to the mice study (FIG. 4), intramuscular VP1 protein vaccine failed to generate intestinal SIgA response although serum VP1 IgG response was well generated (8×104) (FIG. 15). Overall, the oral vaccine of the invention generates comparable levels of serum IgG and superior levels of fecal IgA to VP1 injectable protein vaccine.

Summary of Pharmacology Studies

The studies summarized within this section demonstrated that oral administration of VXA-G2.4-NS could elicit substantial antibody responses to norovirus VP1 by ELISA in mice and ferrets. Local immunity could play a very important role preventing infection and disease, and SIgA would likely be the most effective gut immune response to combat a gut pathogen such as norovirus. These studies demonstrate that VXA-G2.4-NS oral delivery generated intestinal SIgA response and superior levels of SIgA to VP1 injectable protein vaccine.

The duration of norovirus infection is relatively short. Norovirus has around 2 days of incubation time, followed by illness with vomiting and diarrhea, which lasts 2 to 4 days. T and B cell responses start to occur around 4 days after infection. Interestingly, the clearance of norovirus occurs just after development of the early stage of T and B cells' activation. However, the oral vaccine of the invention could manipulate the immune response to benefit the individual. Before norovirus infection, the oral vaccine will induce gut homing B cells to secrete VP1 specific SIgA antibody. IgA enriched gut homing B cells in PBMC were detected in previous studies. SIgA will pass across the intestinal epithelial cells to the alimentary tract (gut lumen). After norovirus infection, SIgA will act as a blocking (neutralizing) antibody against norovirus infection. In conclusion, a gut pathogen is an excellent match for the oral platform because the oral delivery method activates immune cells with the desired gut homing property and intestinal SIgA is the most effective gut immune response to combat a gut pathogen.

Example 7

Phase 1 VXA-G24-NS Study Synopsis

This study is a phase 1, randomized, double-blind, placebo-controlled, dose-ranging trial to determine the safety and immunogenicity of an adenoviral-vector based norovirus vaccine (vxa g2.4-ns) expressing gii.4 vp1 and dsma adjuvant administered orally to healthy volunteers. The study will be conducted in 1-2 U.S. sites on healthy adult volunteers age 18 to 49 years. Subject participation in the study will last ~1 year following successful screening and enrollment. After vaccination subjects will be followed for one month for efficacy (immunogenicity) and for 12 months for safety.

Investigational Product

VXA-G2.4-NS is an E1/E3-deleted replication-defective Adenovirus serotype 5 vaccine vector for prevention of noroviral gastroenteritis caused by Norovirus GII.4. The vaccine vector encodes for a full-length VP1 (major capsid protein) gene from Norovirus GII.4 Sydney and is described in detail in Example 6.

The GII.4 VP1 gene is expressed using a human Cytomegalovirus (CMV) intermediate early region (hCMVie) enhancer/promoter. In addition to the transgene cassette, a second hCMVie promoter is used to express a double-stranded RNA (dsRNA) sequence that acts as a TLR3-based adjuvant.

Control Product

A placebo tablet dosage formulation indistinguishable in appearance and number from the vaccine tablets Regimen and Dosing Single administration of VXA-G2.4-NS at a low dose of 1×1010 IU, a high dose of 1×1011 IU or placebo. The number of tablets per dose will be calculated based on the release assay results for the drug product. Two sentinel groups will enroll three subjects each in an open-label manner (Cohorts 1 and 3) to receive VXA-G2.4-NS prior to enrolling either of the randomized, controlled cohorts (Cohorts 2 and 4). Within the double-blinded groups (Cohorts 2 and 4), placebo subjects will receive the same number of tablets as vaccine subjects. Subjects will be enrolled and dosed in the low dose group prior to initiation of dosing in the high dose group.

Cohort 1: $1 \times 10^{10}$ IU±0.5 logs (n=3)
Cohort 2: $1 \times 10^{10}$ IU±0.5 logs (n=20) or placebo (n=10)
Cohort 3: $1 \times 10^{11}$ IU±0.5 logs (n=3)
Cohort 4: $1 \times 10^{11}$ IU±0.5 logs (n=20) or placebo (n=10)

Subjects in Cohorts 2 and 4 will be randomized in a 2:1 ratio to VXA-G2.4-NS at $1 \times 10^{10}$ IU (low dose) or $1 \times 10^{11}$ IU (high dose), respectively, or placebo.

Objectives

The primary objective is to determine the safety of a VXA-G2.4-NS norovirus vaccine candidate. The secondary objective is to determine the immunogenicity of a VXA-G2.4-NS norovirus vaccine candidate at two dose levels Study Design This is a Phase 1, randomized, placebo-controlled, double-blind (after initial open-label lead-in), dose-ranging study to assess the safety, reactogenicity and immunogenicity of an adenoviral-vector based oral Norovirus GII.4 vaccine and dsRNA adjuvant. All subjects will receive a single vaccine administration.

The study will be enrolled in four cohorts:
Cohort 1: VXA-G2.4-NS at $1 \times 10^{10}$ IU (low dose) sentinel
Cohort 2: VXA-G2.4-NS at $1 \times 10^{10}$ IU (low dose) or placebo
Cohort 3: VXA-G2.4-NS at $1 \times 10^{11}$ IU (high dose) sentinel
Cohort 4: VXA-G2.4-NS at $1 \times 10^{11}$ IU (high dose) or placebo Cohort 1 (low dose sentinel group) will enroll 3 subjects to receive a single dose of VXA-G2.4-NS at $1 \times 10^{10}$ IU on Day 0. The 3 subjects will be enrolled sequentially (one per day), in an open-label manner. Upon completion of the Day 7 Visit in all 3 subjects, if no dose-limited toxicities are observed in these sentinel subjects (see Halting Rules below), enrollment will begin in Cohort 2.

Cohort 2 (low dose randomized group) will randomize 30 subjects in a 2:1 ratio to receive either VXA-G2.4-NS at $1 \times 10^{10}$ IU (low dose) (n=20) or placebo (n=10) in a double-blinded manner.

The study will enroll continuously during this phase unless the criteria for pre established stopping rules are met (see below). Should this happen, enrollment of subsequent subjects will not be initiated until the study Safety Monitoring Committee (SMC) has completed review of safety data and offered the recommendation to proceed. The safety assessment will be performed with the treatment assignments coded in Cohort 2. If the SMC needs treatment information to assess an AE/SAE, the code will be revealed for that subject.

Upon completion of the Day 7 Visit in all 30 subjects, if no dose-limited toxicities are observed in these subjects (see Halting Rules below), enrollment will begin in Cohort 3. Cohort 3 (high dose sentinel group) will enroll 3 subjects to receive a single dose of VXA-G2.4-NS at $1 \times 10^{11}$ IU on Day 0. The 3 subjects will be enrolled sequentially (one per day), in an open-label manner. Upon completion of the Day 7 Visit in all 3 subjects, if no dose-limited toxicities are observed in these sentinel subjects (see Halting Rules below), enrollment will in Cohort 4.

Cohort 4 (high dose randomized group) will randomize 30 subjects in a 2:1 ratio to receive either a single dose of VXA-G2.4-NS at $1 \times 10^{11}$ IU (high dose) (n=20) or placebo (n=10) in a double-blinded manner.

The study will enroll continuously during this phase unless the criteria for pre-established stopping rules are met (see Halting Rules below). Should this happen, enrollment of subsequent subjects will not be initiated until the SMC has completed review of safety data and offered the recommendation to proceed. The safety assessment will be performed with the treatment assignments coded in Cohort 4. If the SMC needs treatment information to assess an AE/SAE, the code will be revealed for that subject.

All subjects receiving study drug (vaccine or placebo) will have safety and immunogenicity assessments completed for one month following vaccination. Immunogenicity evaluations will be obtained at baseline prior to vaccination, and at Days 7 and 28 following vaccination. Subjects will also be evaluated for persistent immunogenicity at Day 180 and be followed for safety for 12 months following vaccination.

Sample Size

The planned enrollment in this study is 66 subjects as follows:
Cohort 1: VXA-G2.4-NS ($1 \times 10^{10}$ IU±0.5 logs): n=3, sentinel
Cohort 2: VXA-G2.4-NS ($1 \times 10^{10}$ IU±0.5 logs): n=20, or placebo: n=10; total 30 subjects, 2:1 ratio
Cohort 3: VXA-G2.4-NS ($1 \times 10^{11}$ IU±0.5 logs): n=3, sentinel
Cohort 4: VXA-G2.4-NS ($1 \times 10^{11}$ IU±0.5 logs): n=20, or placebo: n=10; total 30 subjects, 2:1 ratio Additional subjects may be enrolled to replace dropouts.

Study Population

Male or female healthy volunteers, 18 to 49 years of age.

Inclusion/Exclusion Criteria

Inclusion criteria include:
1. Male or female volunteers aged 18-49 years, inclusive
2. Able to give written informed consent
3. Healthy (no clinically significant health concerns), as determined by medical history, physical examination, 12-lead ECG, and vital signs at screening
4. Safety laboratory values within the following range criteria at baseline:
    a. Normal range for alkaline phosphatase (ALP), alanine aminotransferase (ALT), aspartate aminotransferase (AST), bilirubin, phosphorous (hypophosphatemia), neutrophils, occult blood, white blood cells (WBC), and urine protein;
    b. Normal or grade 1 abnormality with no clinical significance (NCS) for albumin, amylase, blood urea nitrogen (BUN), calcium, creatine phosphokinase (CPK), creatinine, glucose, magnesium, potassium, sodium, total protein, eosinophils (increase), hemoglobin, lymphocytes (decrease), and platelets;
    c. Negative or positive with NCS for blood urine
5. Body mass index between 17 and 35 at screening
6. comprehension of the study requirements with ability and willingness to complete all assessments and comply with scheduled visits and contacts
7. Female participants must have a negative pregnancy test at baseline and fulfill one of the following criteria:
    a. At least one year post-menopausal;
    b. Surgically sterile;
    c. Willing to use oral, implantable, transdermal or injectable contraceptives for 30 days prior to and until 60 days after vaccination;
        i. A reliable form of contraception must be approved by the Investigator (e.g., double barrier method, Depo- Provera, intrauterine device, Norplant, oral contraceptives, contraceptive patches, abstinence)

Exclusion Criteria Include:
1. Receipt of any norovirus vaccine within two years prior to study vaccination
2. Administration of any investigational vaccine, drug or device within 8 weeks preceding vaccination, or planned use of the above stated during the study through the 12-month safety follow-up
3. Administration of any licensed vaccine within 30 days prior to vaccination
4. Presence of significant uncontrolled medical or psychiatric illness (acute or chronic) including institution of new medical/surgical treatment or significant dose alteration for uncontrolled symptoms or drug toxicity within 3 months of screening and reconfirmed at baseline
5. My one of the following ECG findings within 30 days prior to vaccination:
a. QTc (Bazett) interval duration >450 msec (male) or >470 msec (female),
b. QRS interval greater than 120 msec,
c. PR interval greater than 220 msec,
d. Clinically significant ST-T wave changes or pathologic Q waves
6. Positive serology for HIV-1 or HIV-2, or HBsAg or HCV antibodies
7. Cancer, or treatment for cancer treatment, within past 3 years (excluding basal cell carcinoma or squamous cell carcinoma).
8. Presence of immunosuppression or medical condition possibly associated with impaired immune responsiveness, including diabetes mellitus
9. Administration of any medications or treatments that may adversely affect the immune system such as allergy injections, immune globulin, interferon, immunomodulators, cytotoxic drugs or other drugs known to be associated with significant major organ toxicity, or systemic corticosteroids (oral or injectable) during 3 months prior to vaccination. Inhaled and topical corticosteroids allowed
10. Presence of household members who have received the Ad4 or Ad7 vaccines within 2 months prior to vaccination
11. Presence of household members who are neonates, pregnant women, or hematopoietic stem cell transplant or solid organ transplant recipients
12. History of drug, alcohol or chemical abuse within 1 year prior to vaccination
13. Receipt of blood or blood products 6 months prior to vaccination or planned administration during the follow-up study period
14. Donation of blood or blood products within 4 weeks prior to vaccination or planned donation during the study period
15. Acute disease within 72 hours prior to vaccination defined as the presence of a moderate or severe illness with or without fever (as determined by the Investigator through medical history and physical examination)
16. Presence of a fever ≥38° C. measured orally at baseline
17. Stool sample with occult blood at screening
18. Positive urine drug screen for drugs of abuse at screening
19. Consistent/habitual smoking within 2 months prior to vaccination
20. History of serious reactions to vaccination such as anaphylaxis, respiratory problems, hives or abdominal pain
21. Diagnosed bleeding disorder or significant bruising or bleeding difficulties that could make blood draws problematic
22. History of irritable bowel disease or other inflammatory digestive or gastrointestinal condition that could affect the distribution/safety evaluation of an orally administered vaccine targeting the mucosa of the small intestine.

Such conditions may include but are not limited to:
26. Any condition that, in the opinion of the Investigator, might interfere with ability to assess the primary study objectives STUDY SCHEDULE The following study visits/calls will be conducted during the study:
Screening Period (within 30 days prior to vaccination)
Day −2 (Baseline safety laboratory sample collection)
Day 0 Visit (Baseline; day of vaccination)
Day 2 Visit
Day 7 Visit
Day 28 Visit
Day 180 Visit
Day 365 End of Study Contact
Subjects will be followed via phone call daily on Days 1, 3 to 6, and 14. They will also be contacted monthly between the Day 28 and Day 180 Visits and also following the Day 180 Visit through Day 365 (end of study). See Table 1 for detailed schedule of study procedures.

Safety and Immunogenicity Assessments
Safety:
Safety and tolerability will be evaluated by: local (oral, esophageal and gastrointestinal) and systemic reactogenicity (solicited symptoms), and clinical and laboratory assessments. Physical exams, routine urinalysis, complete blood counts and serum chemistries will be collected pre-dose at Screening and Baseline (safety labs at Day −2) and at Study Days 2, 7 and 28. Vital signs will be recorded pre-dose at Screening and Baseline and at Study Days 2, 7, 28 and 180.

Safety will be evaluated using standard blood chemistry, hematology and urinalysis, and analyses performed per statistical methods below. Any subject who experiences acute symptoms of conjunctivitis, upper respiratory infection, loose stools and/or diarrhea within 14 days following initial vaccination, will be asked to return for a medical evaluation and evaluation for adenoviral 5 infection. In these subjects, adenoviral cultures of throat and rectal swabs will be collected.

Immunogenicity:
Immunogenicity will be evaluated using cellular and humoral immune function assays from blood samples obtained at baseline (pre-dose) and at Study Days 7 and/or 28 depending on the assay. In addition, a final evaluation for persistent immunogenicity will be performed at Day 180. The following assessments will be performed Serum IgG VP1; Histo-blood group antigen-blocking antibodies (BT50); IgG ASC VP1; IgA ASC VP1; Flow cytometric B cell immunophenotyping; Pre-plasma B cell culture for IgG VP1 and IgA VP1; Fecal IgA VP1; HAI; and Anti-Ad5.

Halting Rules
The study will be halted (no new enrollments and no further investigational product administered pending a full SMC safety review) if any of the below occur: For Cohorts 1 and 3 (3 subject open-label sentinel lead in groups):
1. One or more subject experiences a vaccine-related SAE of any grade;
2. One or more subject experiences a Grade 3 or higher clinical AE or laboratory abnormality;
3. Two or more subjects experience any vaccine-related Grade 2 clinical AE or laboratory abnormality.

For Cohorts 2 and 4 (randomized, placebo-controlled groups):
1. One or more subject experiences a vaccine-related SAE of any grade;
2. Two or more subjects experience Grade 3 clinical or laboratory AEs,
3. One or more subject experiences a Grade 4 clinical AE, or a Grade 4 laboratory abnormality;
4. Three or more subjects present with symptoms of adenovirus infection and detectable replication competent adenovirus 5 vaccine virus. If three or more subjects present with symptoms of adenovirus infection, enrollment will be halted pending results for detection of adenovirus 5 vaccine virus.

Endpoint Parameters

Safety analyses include: 1) Standard descriptive demography; 2) Proportion of subjects in each treatment group will be tabulated for each local and systemic solicited reactogenicity event and any unsolicited AEs. AE severity will be classified using standardized criteria adapted from the September 2007 FDA Guidance entitled "Toxicity Grading Scale for Healthy Adult and Adolescent Volunteers Enrolled in Preventive Vaccine Clinical Trials"; 3) Subjects with AEs (including clinical laboratory abnormalities) will be summarized by (1) MedDRA body organ system and preferred term; (2) severity; (3) relatedness; and, separately, (4) seriousness; 4) Proportion of subjects in each treatment group with AE reports within each body organ system will be compared in the same manner. Significant heterogeneity will be probed at the preferred term level Immunogenicity analyses include: 1) Serum IgG VP1 and Histo-blood group antigen-blocking antibodies (BT50); 2) Additional exploratory analyses will include IgG ASC VP1; IgA ASC VP1; Flow cytometric B cell immunophenotyping; Pre-plasma B cell culture for IgG VP1 and IgA VP1; Fecal IgA VP1; HAI; Anti-Ad5.

Statistical Methods
Sample Size and Power:

This is the first in human clinical trial with VXA-G2.4-NS that will be conducted by the sponsor. There is currently no clinical information about the study drug. Hence the sample size was determined based on experience of a typical Phase 1 vaccine study. The numbers of volunteers per group in Cohorts 2 and 4 are predicted to yield meaningful immunogenicity results. A sample size of 20 in vaccine group and 10 in placebo group (i.e. 2:1 randomization ratio) will provide approximately 86% power to detect a group difference, assuming the proportion of response (observed in serum IgG VP1) in vaccine group is 50% and in placebo is 0, using two-group Fisher's exact two-sided test at significance level of 0.05.

Data Analysis:
Safety:

Safety will be summarized by treatment group. Local and systemic reactogenicity, AEs, clinical laboratory results, and vital signs will be summarized descriptively by study visit Number and percentage of subjects who experience acute symptoms of conjunctivitis, upper respiratory infection, loose stools and/or diarrhea within 14 days following initial vaccination will be compared by treatment group using Fisher's exact test.

Immunogenicity:

Immunogenicity results evaluated by cellular and humoral immune function assays from blood samples collected at preselected study visits will be summarized descriptively. Analysis of covariance (ANCOVA) will be used in the analysis of the antibody titers, with post baseline log-titer as dependent variable, treatment as a factor, and baseline log-titer as a covariate. Least square (LS) means and 95% CI of the LS means will be obtained from the model. The post baseline Geometric (LS) Mean Titer (GMT) for the VXA-G2.4-NS group and Geometric (LS) Mean Fold Rise (GMFR) over the initial GMT at baseline will be reported.

Example 8

RSV Background

Respiratory syncytial virus (RSV) Lithe most important cause of lower respiratory tract infection (LRI) in infants and young children and is a major cause of LRTI is the elderly and immune-compromised patients where it can have devastating effects, causing significant morbidity and mortality. It is estimated to infect 5-10% of nursing home residents per year, with rates of pneumonia or death of 10-20% and 2-5% respectively (Falsey et al. 2000). There is no approved vaccine though there is an approved prophylactic monoclonal antibody, Palivizumab, for disease prevention in high-risk infants.

Given the lack of a vaccine Vaxart is addressing this large unmet medical need by initiating a preclinical program to evaluate a RSV vaccine delivered using it's oral adenovirus vectored platform. This platform has previously being used to deliver influenza vaccines to patients where it's efficacy and inducing significant immunity has been demonstrated. An important strategy in this preclinical path is demonstrating disease protection in a cotton rat RSV challenge model. To this end we have started such an evaluation and will have a complete data set shortly. We present preliminary data in this report, which demonstrates that significant immunity is generated even after a single vaccination. Based on this immune response we expect the vaccine to be protective.

RSVP Vaccine Evaluation in Cotton Rats

Figure 17:
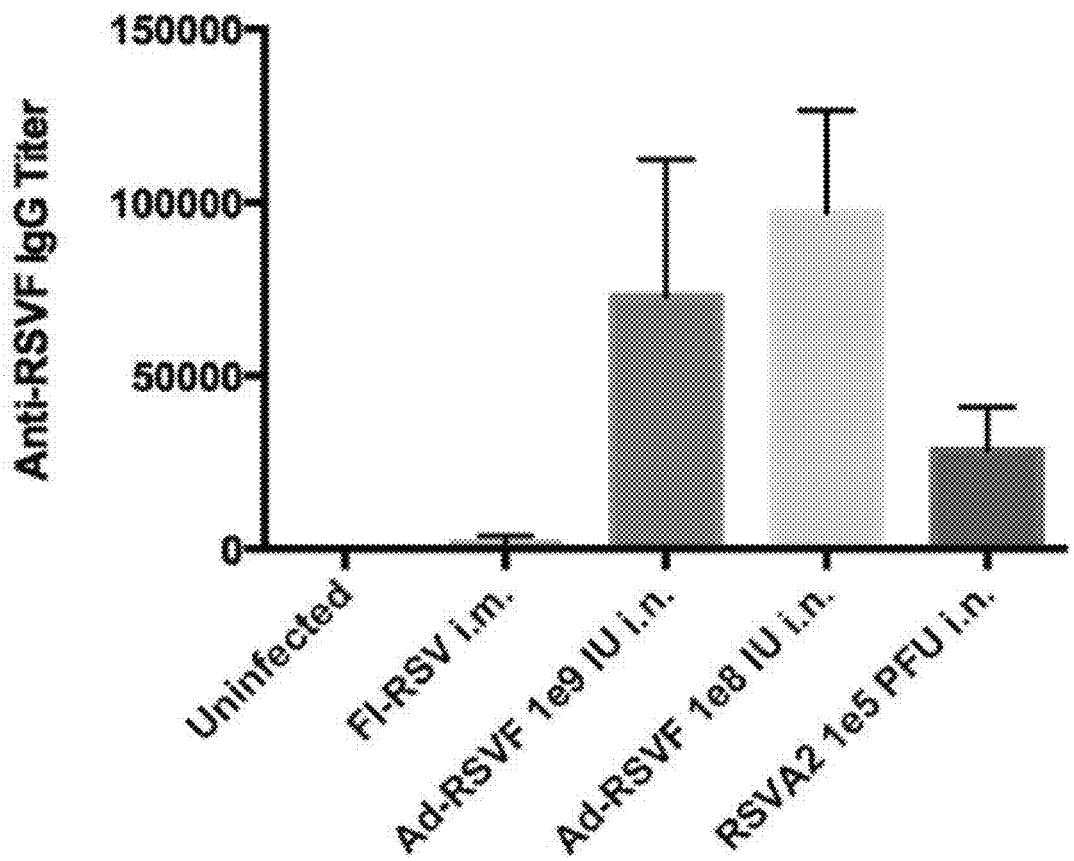
FIG. 17. Anti-RSVF antibody titers in cotton rats at 4 weeks post vaccination with Ad-RSVF vaccine vectors or control formalin inactivated RSV (FIRSV) or live wild-type RSVA2. Titers were determined using an anti-RSVF IgG ELISA.

A vaccine vector (Ad-RSVF) expressing the fusion protein (F) of RSV and a dsRNA adjuvant was generated as described above. The Ad vaccine vector was produced in 293 cells, purified and a titer determined. The vector was then evaluated first in mice where significant immune response was elicited to the fusion protein (data not shown) and then in the relevant RSV animal model, cotton rats. As an oral delivery method has not been optimized in Cotton rats the intra nasal route was chosen as an alternate mucosal route of delivery. Two doses were administered, a low (1e8 IU) and high dose (1e9 IU). Uninfected animals were used as a negative control and wild-type RSV virus (RSVA2) was used as a positive control. Formalin inactivated RSV (FIRSV) was used as a control for undesired negative effects associated with an RSV-vaccine developed in the 1960's. After a single vaccination Ad-RSVF at both low and high doses induced higher titers compared to wild-type RSV infection (FIG. 17) while the FIRSV induced a very weak immune response (200-300× lower). This data indicates that our vaccine is superior at inducing immunity than WTRSV virus and more effective than the earlier FIRSVF vaccine.

Figure 18:
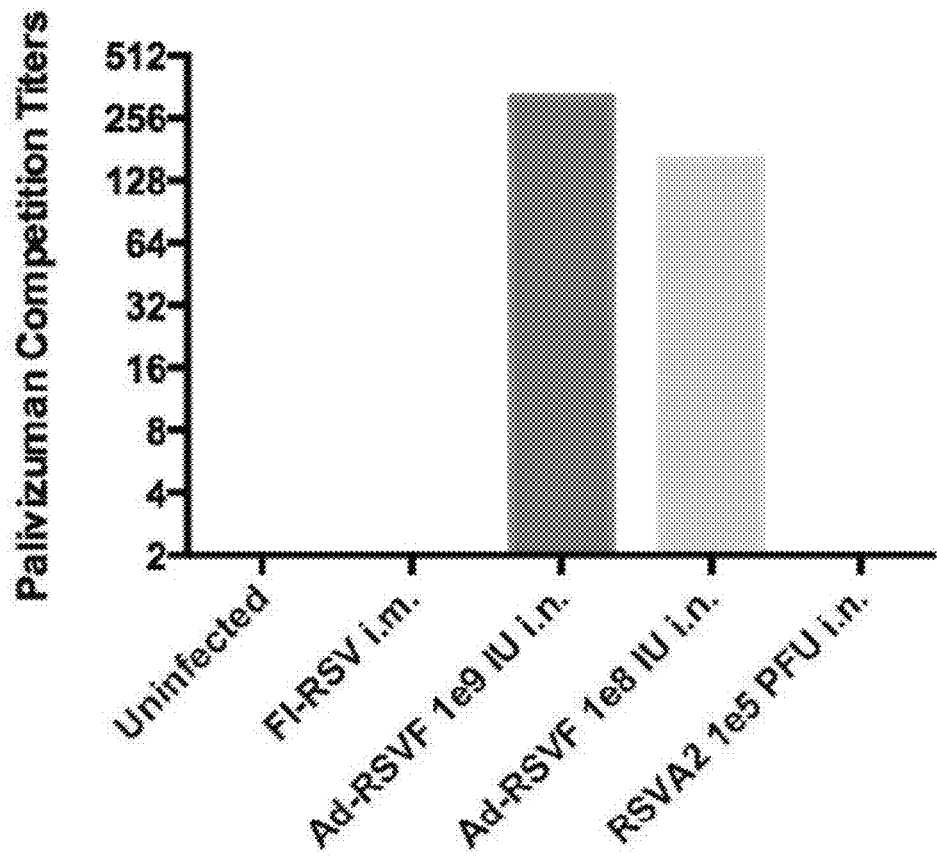
FIG. 18. Palivizumab Competition using sera from cotton rats vaccinated with Ad-RSVF vaccine. ELISA plates were coated with an RSVA2 lysate at 1 ug/mL. Biotinylated Palivizumab (10 ng/mL) was mixed with serial 2-fold dilutions of control and test sera. Naïve sera was used to determine 100% Palivizumab binding. Unlabelled Palivizumab was used as positive control. HRP-Strepavidin with TMB substrate was used to detect biotinylated Palivizumab. Inhibition was scored relative to 100% biotinyaled Paliziumab binding. The maximum dilution that gave 50% or greater neutralization activity was assigned as the competition titer.

In addition to total anti-Fusion protein antibodies (FIG. 17) we also looked at antibodies generated by our vaccine that could compete with the approved Palivizumab antibody. In a competition assay using pooled sera from each of the treatment groups only the Ad-RSVF vaccine generated detectable antibody titers (FIG. 18). These data indicate that the vaccine is producing RSV protective antibodies.

VXA-RSV-f Nonclinical Studies 8.1 Introduction

VXA-RSV-f is an E1/E3-deleted replication-incompetent serotype 5 adenovirus vector designed for use as a vaccine for the prevention of RSV and administered by the oral route. The recombinant adenovirus (rAd) vector codes for 1) the fusion (F) gene from the RSV A2 strain (Genbank #HQ317243.1) and 2) an adjuvant dsRNA sequence that enhances the immunogenicity of the expressed F antigen in the gut mucosa via its TLR3 agonistic activity. The vaccine backbone is identical to that in Vaxart's ND1.1, VXA-A1.1 and VXA-BYW.10 vaccines for pandemic and seasonal influenza A and B, respectively, currently in clinical development; the only change being that VXA-RSV-f has a different surface protein (F protein) being expressed. The RSV F protein gene has been colon-optimized for expression in mammalian cells and is expressed using a human cytomegalovirus intermediate early region (hCMVIE) enhancer/promoter and a bovine growth hormone polyadenylation (pA) signal. This expression cassette also includes the first intron of human β-globin to enhance transgene expression. A second hCMVIE promoter is used to express the adjuvant RNA sequence. The adjuvant sequence is derived from a luciferase sequence and has been reported to stimulate the induction of type I interferon in vitro (1). The adjuvant is expressed as a short hairpin RNA, comprising a 21-nucleotide sequence (GAAACGATATGGGCT-GAATAC) SEQ ID NO: 11 as a tandem sequence in forward and reverse orientations separated by six nucleotides that comprise the loop of the RNA. The 21-nucleotide forward and reverse RNA sequences anneal to form the stem of the loop. This adjuvant cassette utilizes a synthetic poly A (SPA).

Vaxart has conducted preclinical studies to determine the immunogenic potential of VXA-RSV-f in mice and cotton rats. These studies showed that vaccination with VXA-RSV-f elicited substantial systemic serum IgG responses in test animals.

As described above, Vaxart's RSV vaccine (VXA-RSV-f) will use the same replication-defective viral vector backbone and adjuvant RNA sequence as the company's pandemic and seasonal influenza virus programs. The A/Indonesia/05/2005 (H5N1) pandemic influenza vaccine, ND1.1, is presently being studied under BB-INDs 14660 and 15122, and the A/California/04/2009 (H1N1) seasonal influenza vaccine, VXA-A1.1, is presently being studied under BB-INDs 15198 and 15285. The B/Wisconsin/1/2010 (Yamagata) vaccine is presently being studied under BB-END 16611. Because the only difference between the vaccines is the antigen gene [the F protein in VXA-RSV-f versus HA in VXA-A1.1, ND1.1 and VXA-BYW.10], the preclinical studies from ND1.1 and VXA-A1.1 are relevant to and support the clinical development of the VXA-RSV-f vaccine for prevention of RSV disease.

8.2 Nonclinical Pharmacology
8.2.1 Introduction

The primary objective of the immunogenicity studies of the RSV vaccine candidate VXA-RSV-f was to demonstrate that vector construct could elicit antibody responses in mice and cotton rats, and that the adaptive immune responses generated did not lead to enhanced RSV disease such as that known to occur with the formalin inactivated RSV vaccine. Further, studios were performed in animals to demonstrate the value of the adjuvant for inducing antigen specific immune enhancement.

TABLE 5

Nonclinical Pharmacology Studies

| Study Title (Study No.) | Animal Model (Species, Gender, No.) | Therapy (Treatment) | VXA-RSV-f (Immunization schedule) | Endpoints (Sample collection time points) | Endpoints (Assays) |
|---|---|---|---|---|---|
| | | Immunogenicity Study of Ad-CMV-RSVf-dsRNA Vaccine | | | |
| Study No. WCB254 | Balb/c mice. 6 F per group | Group 1: VXA-RSV-f i.n. (1 × 10$^8$ IU$^a$) Group 2: VXA-RSV-f i.m. (1 × 10$^8$ IU) Group 3: VXA-RSV-f oral (1 × 10$^8$ IU) | Days 0 and 21 | 7 weeks | RSV-F ELISA |
| Study No. XV-95$^c$ Cotton rat challenge study | Cotton rats 6 F per group, or 3 F per group for uninfected control group | Group 1: VXA-RSV-f i.n. (1 × 10$^9$ IU) Group 2: VXA-RSV-f in. (1 × 10$^8$ IU) Group 3: VXA-RSV-f i.m. (1 × 10$^9$ IU) Group 4: rAd-Adj (1 × 10$^9$ IU) Group 5: untreated/unifected Group 6: FI-RSV Group 7: Buffer alone Group 8: RSV/A2 le5 PFU | Days 0 and 28 Challenge day 56 | 8 weeks; Day 5 post challenge | RSV-F ELISA (serum IgG), anti-palivizurnab competition assay, PFtNT antibodies. RSV replication post challenge |
| Study No. XV-112$^c$ Cotton rat immunogenicity (and challenge) | Cotton rats 8 F per group, or 6 F for buffer control group | Group 1: Buffer alone Group 2$^b$: oral VXA-RSV-f (1 × 10$^{10}$ IU) Group 3: oral VXA-RSV-f (1 × 10$^9$ IU) Group 4: Oral VXA-RSV-f (1 × 10$^8$ IU) | Days 0 and 28 Challenge day 56 | 8 weeks; Day 5 post challenge | RSV-F ELISA (serum IgG), anti-palivizumab competition assay, PRNT antibodies. RSV replication post challenge |

$^a$IU = infectious units
$^b$oral delivery was conducted by gavage by Sigmovir (Rockville, MD)

8.2.2 Immunogenicity and Challenge Studies

The primary objective of the initial mouse immunogenicity study (Study No. WCB254) was to determine if the Vaxart vector backbone expressing the RSV F protein could induce an antibody response to RSV as measured by ELISA. Following completion of the mouse study, two cotton rat studies were performed. The objectives of the cotton rat studies were to demonstrate that VXA-RSV-f could elicit potent antibodies to RSV, and that the vaccine could elicit protective immune responses against RSV. Further, the cotton rat studies were used to determine that VXA-RSV-f induced adaptive immune responses did not enhance RSV disease, such as those recorded for the old formalin inactivated RSV vaccine (FI-RSV).

Immunogenicity Studies in Mice

Figure 22:
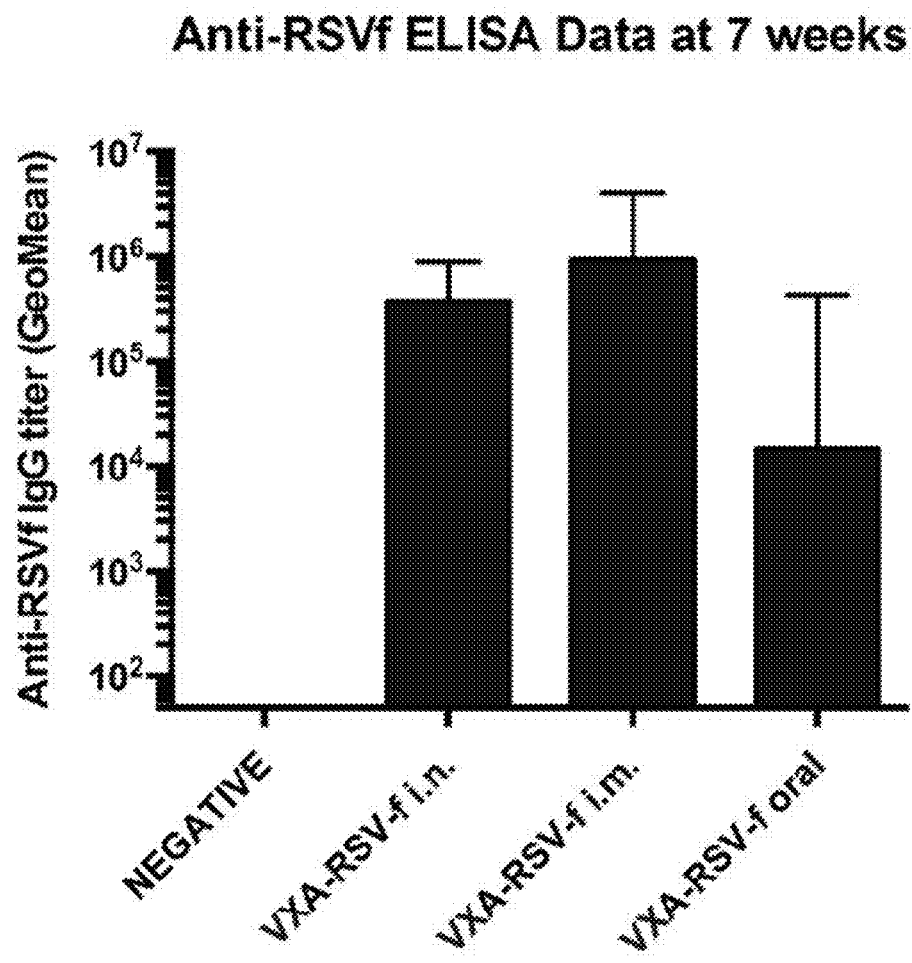
FIG. 22 shows, mice elicit robust antibody titers against RSV when given VXA-RSV-f. Study No. WCB254: Balb/c mice were immunized with VXA-RSV-f at 0 and 3 weeks using three different routes of delivery. ELISA IgG antibody titers were measured at week 7. All routes of delivery generated significant immune responses against RSV; however, i.n. and i.m. were more effective at producing higher titers than oral (p 0.04, or 0.02 by Mann-Whitney). N=6 per group. As negative controls, mouse sera from aminals given is norovirus vaccine were used.

Mice (6 females/group) were immunized with VXA-RSV-f using three different routes of delivery in order to determine whether the construct was immunogenic. Animals were immunized with $1\times10^8$ IU on weeks 0 and 3 using three different routes of delivery (intranasal, intramuscular, and oral). Antibody titers to RSV were measured on week 7. Results' show that both the i.n. and i.m. routes of delivery were potent at eliciting antibody responses, and that oral administration was able to elicit some immunity but was not as potent in mice as the other two routes of delivery. See FIG. 22.

Immunogenicity and Challenge Studies in Cotton Rats

The objectives of the first cotton rat study (Study No. XV-95) were to determine the ability of VXA-RSV-f to induce antibody responses and to protect against RSV disease and viral replication. The cotton rat is considered an important model for preclinical development of RSV vaccines because of the susceptibility of the animal to RSV infection, and the reproducibility of the lung inflammation/cytokine skewing phenotype when given formalin inactivated RSV vaccine (FI-RSV) followed by RSV challenge (2). Female cotton rats (N=6 per group) were immunized with VXA-RSV-f by intranasal (i.n.) and intramuscular (i.m.) delivery on weeks 0 and 4 at $1\times10^9$ IU. A lower dose i.n. delivery group at $1\times10^8$ IU of VXA-RSV-f (VXA-RSV-f low) was also used. The VXA-RSV-f vaccine treated animals were compared for ELISA IgG titers on week 8 with a no infection/ho vaccine control group (No infection), an adenovirus storage buffer alone (buffer) group and a FI-RSV vaccine group at 1:100 dilution of a stock (Lot #100) made by Pfizer from the RSV-A2 strain (3). To show that post challenge results were antigen specific, a rAd that expresses the adjuvant without the antigen at $1\times10^9$ IU (Ad-Adj) was given i.n. and used as a control. As a positive control for immunogenicity and adaptive immune mediated protection, a single dose of wild-type RSV strain A2 (RSV2) at $1\times10^5$ PFU was given on week 0. Refer to Table 5 for summary of study treatment groups, time points and endpoints.

Figure 23A:
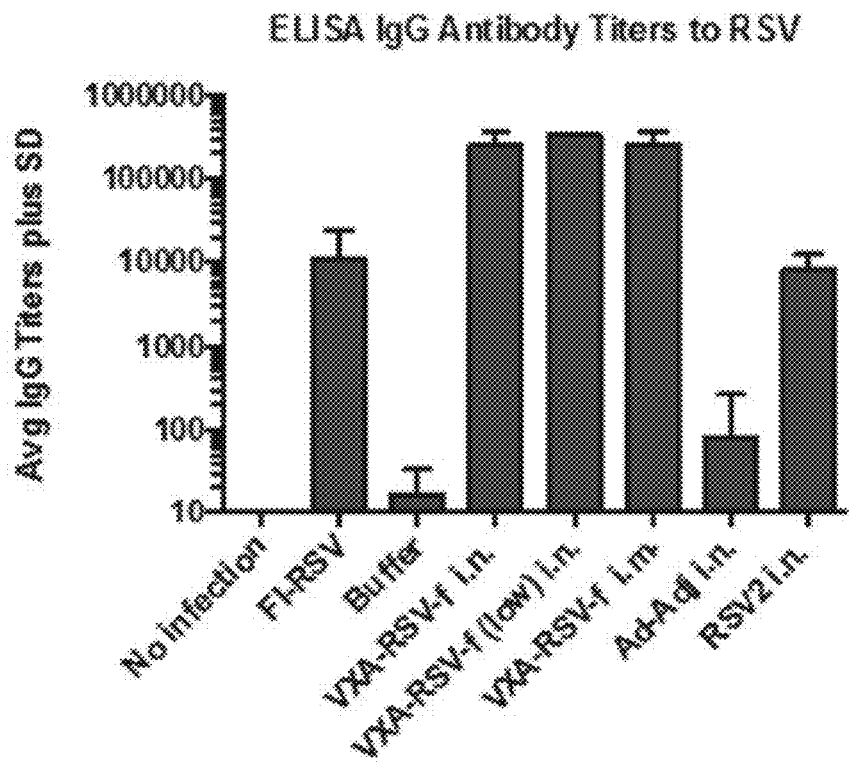
FIGS. 23A-23C shows immunization of cotton rats with VXA-RSV-f vaccine induces antibody responses to RSV. (Experiment XV-95).
Figure 23B:
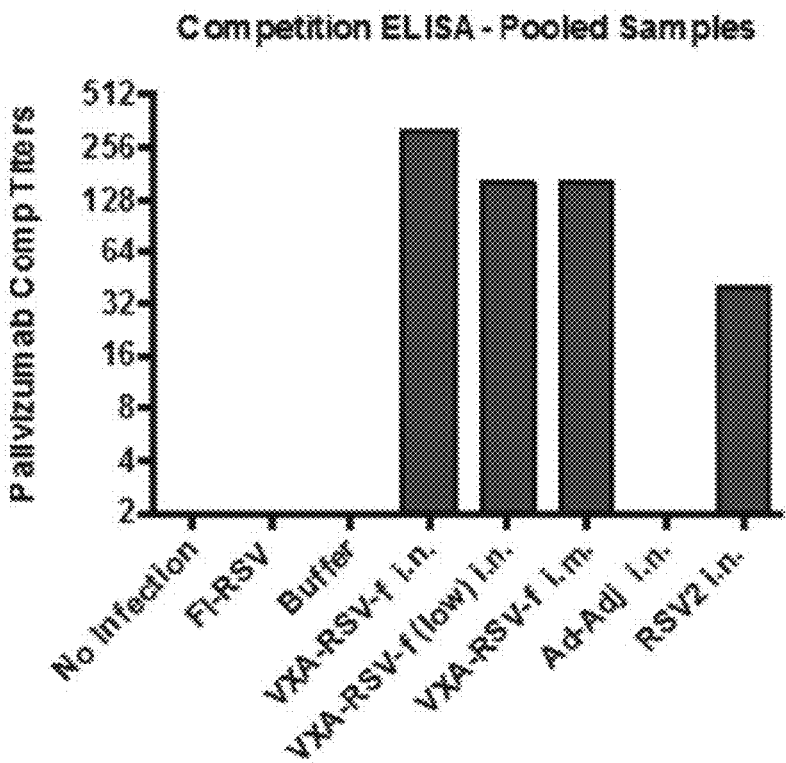
Figure 23C:
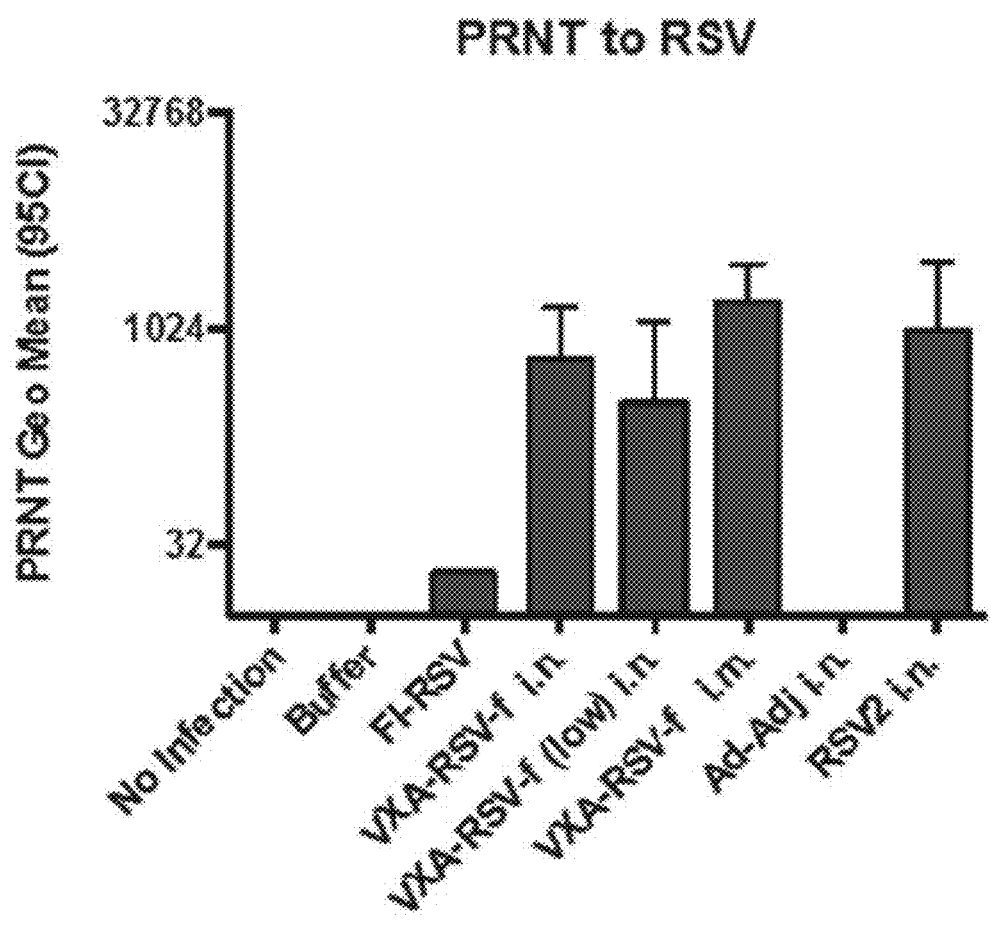

All VXA-RSV-f immunized animals induced significant IgG antibody titers to RSV, with group average antibody titers exceeding $1\times10^5$ (FIG. 23A) at week 8. The FI-RSV and the RSV2 immunized animals also induced significant IgG antibody titers, with average titers reaching $1\times10^4$ on week 8 (FIG. 23A). The VXA-RSV-f vaccine treated animals were also able to induce antibodies that competed for the palivizumab binding site on the F protein of the RSV virus, as measured by the competitive binding ELISA, whereas the FI-RSV vaccine did not induce antibodies that were able to recognize the palivizumab binding site (FIG. 23B). There was some ability of the wild-type RSV2 group (positive control) to induce antibodies that compete for the palivizumab binding site. Neutralizing antibodies to RSV were measured by PRNT assay. A similar trend to the palivizumab analysis was seen, with all VXA-RSV-f groups able to induce significant neutralizing antibodies to RSV, whereas the FI-RSV vaccine was not able to induce substantial neutralizing titers (FIG. 23C). RSV2 control vaccine was able to elicit similar neutralizing titers as the VXA-RSV-f groups statistically speaking, with the VXA-RSV-f (i.m.) having the highest geometric mean titer (p=0.47 by Mann-Whitney).

The objectives of the second cotton rat study (Study No. XV-112) were to determine if cotton rats could be immunized orally with the VXA-RSV-f vaccine and induce significant immune responses. Challenge was optional, subsequent to effective oral immunization. Oral immunization can be difficult in animals, and prior documented experience for rAd oral dosing in cotton rats' was not available. For this reason, a dose titration of the VXA-RSV-f vaccine was performed with doses at $1\times10^8$, $1\times10^9$, and $1\times10^{10}$ IU given by of oral gavage to stomach-neutralized cotton rats to approximate human oral tablet delivery. Animals were immunized on weeks 0 and 4 and the antibody titers were measured on weeks 4 and 8. A buffer only group was used as a control, to show the background effects of no immunization.

Figure 24A:
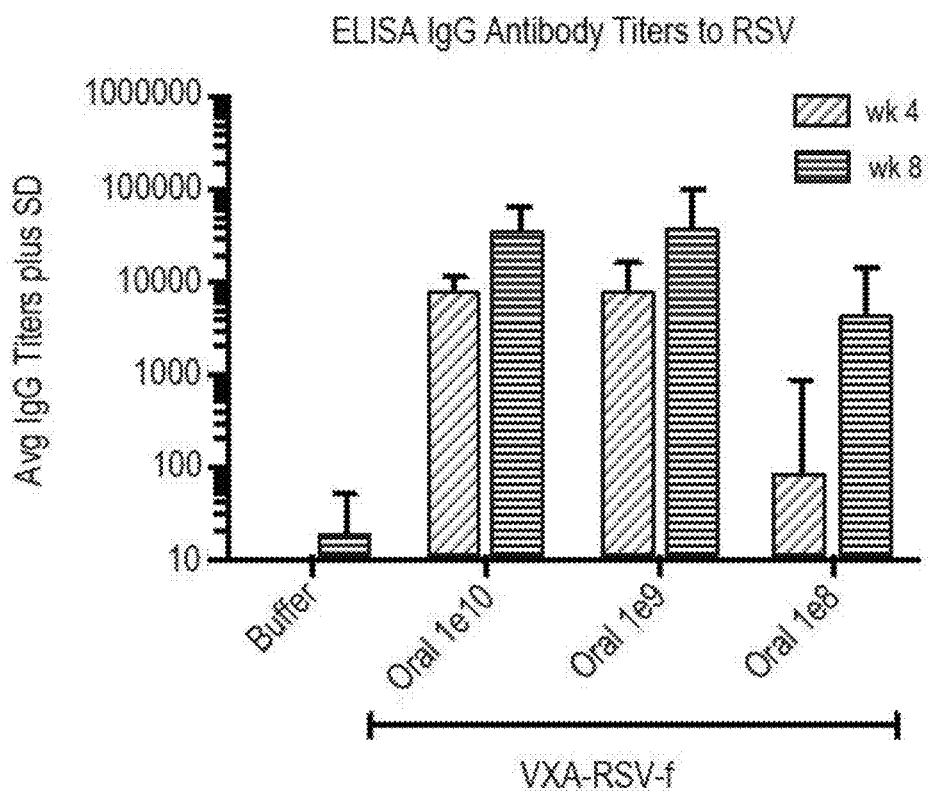
FIGS. 24A-24C show oral immunization induces potent antibodies to RSV in cotton rats. (Experiment XV-112).
Figure 24B:
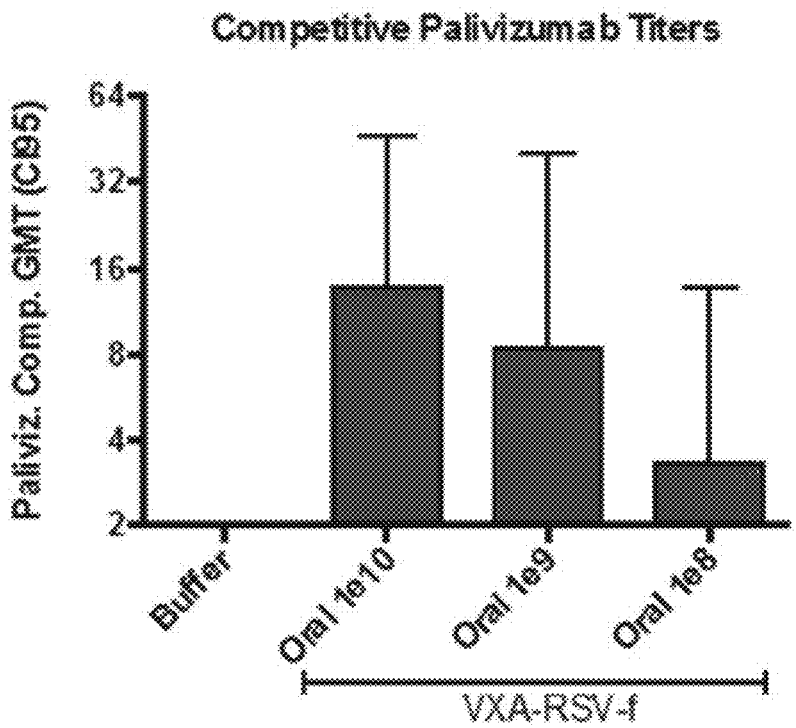
Figure 24C:
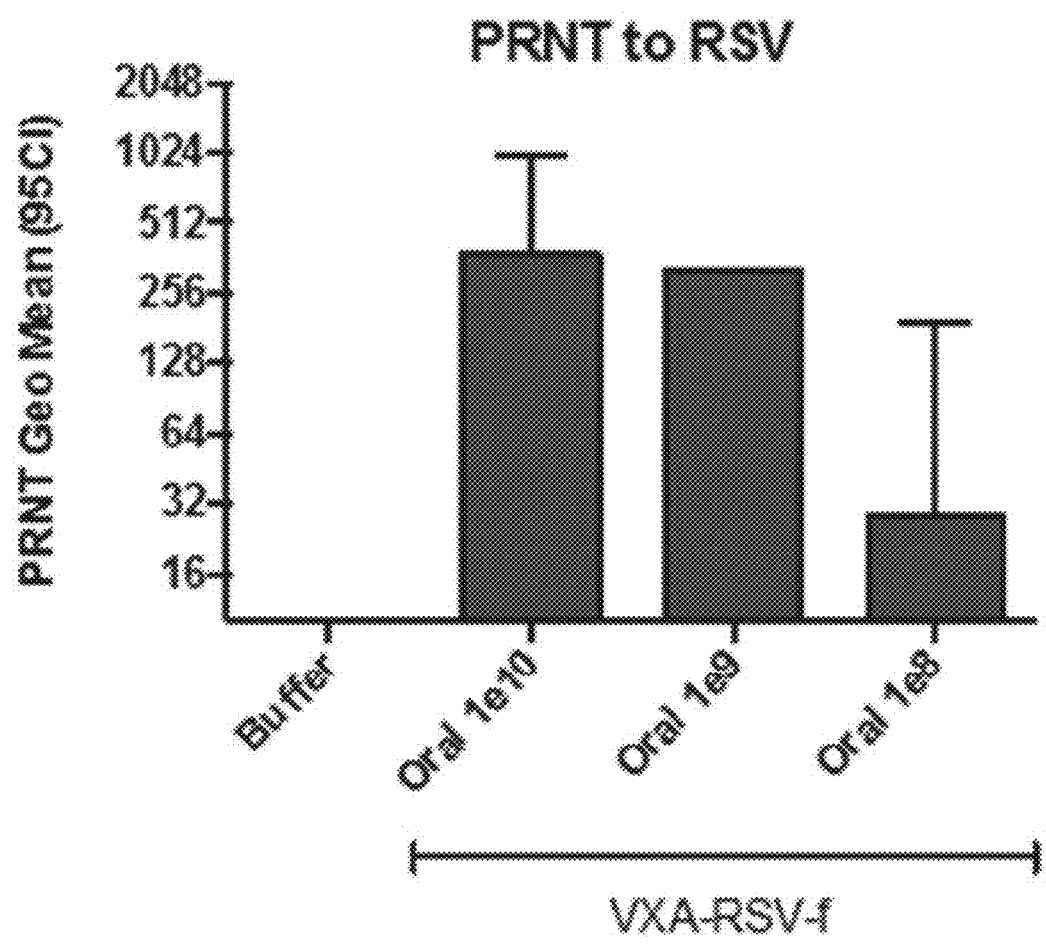

The results show that both $1\times10^9$ and $1\times10^{10}$ doses could induce significant antibody titers to RSV-F on week 4, with significant boosting at week 8 (FIG. 24A). The $1\times10^8$ IU vaccine group trended lower in terms of total IgG antibody responses to RSV. Measurement of the ability of oral VXA-RSV-f to induce antibodies that could compete for the palivizumab binding site showed a dose dependent effect with higher doses showing higher average competitive titers than the lower $1\times10^8$ IU dose (FIG. 24B). Induction of neutralizing antibodies to RSV increased with higher vaccine doses, with the $1\times10^9$ and $1\times10^{10}$ IU VXA-RSV-f vaccine doses eliciting the higher neutralizing titers (FIG. 24C).

Figure 25A:
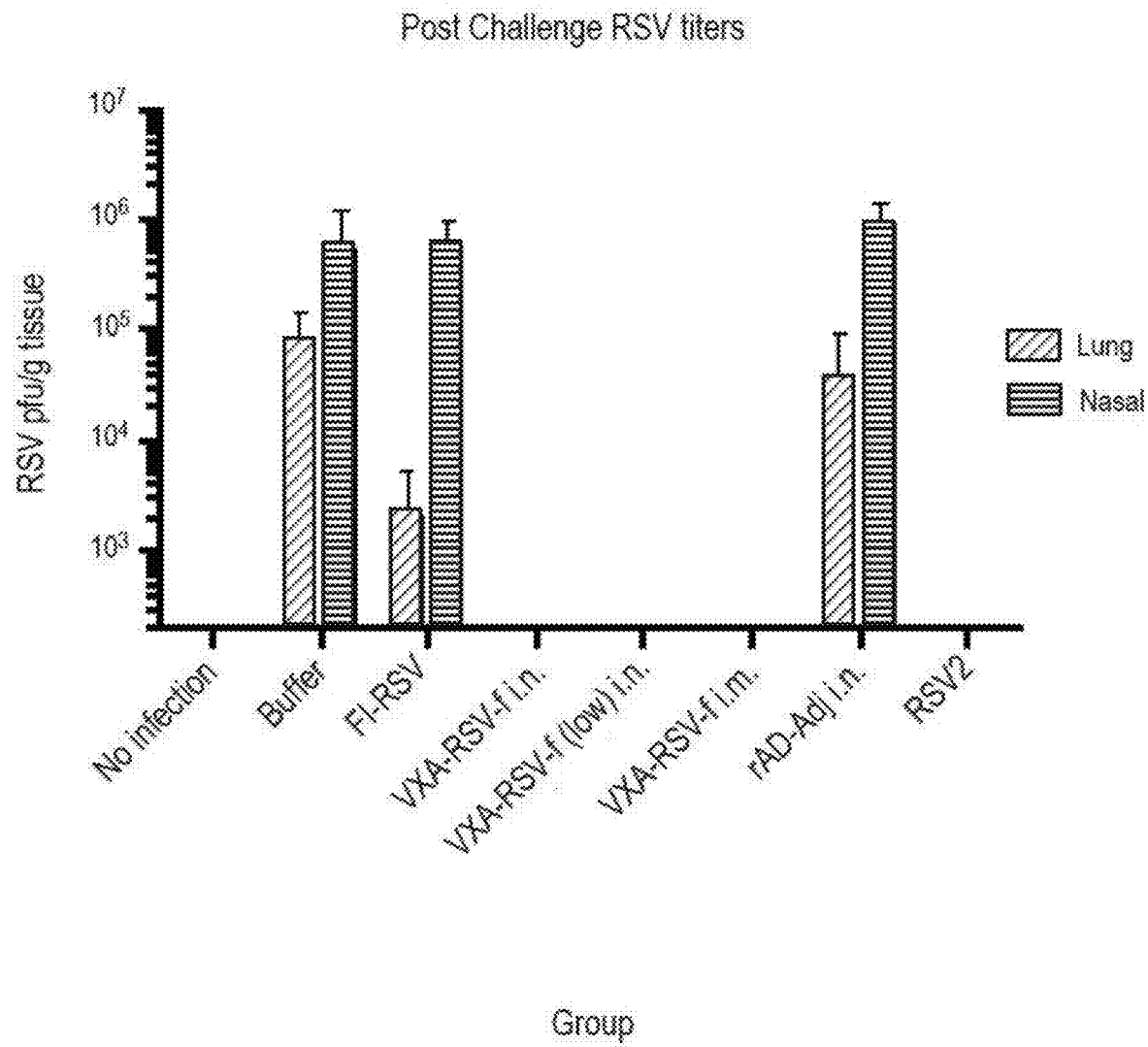
FIGS. 25A-25C shows VXA-RSV-f protects against RSV replication and adaptive immune enhancements of RSV disease. (Experiment XV-95)

Following immunization in the first cotton rat experiment (XV-95, FIG. 23), cotton rats were given wild-type RSV strain A2 at $1\times10^5$ PFU at day 56. Lungs and nasal passages were harvested 5 days later and analyzed for the ability of the vaccines to protect against RSV replication and disease in cotton rat tissue. Immunization with the VXA-RSV-f vaccine provided complete protection against RSV replication in both lungs and the nose, whereas the formalin inactivated vaccine (FI-RSV) and adjuvant alone (Ad-Adj) groups provided no protection against RSV replication in the nose and only limited protection in the lungs with the FI-RSV vaccine (FIG. 25A). Maximal replication (as seen in the buffer control group) had an average of 4.9 $\log_{10}$ PFU RSV/g of lung tissue, and vaccine induced immunity was able to reduce the post challenge RSV titers below the detectable level, a greater than 3 $\log_{10}$ decrease.

Figure 25B:
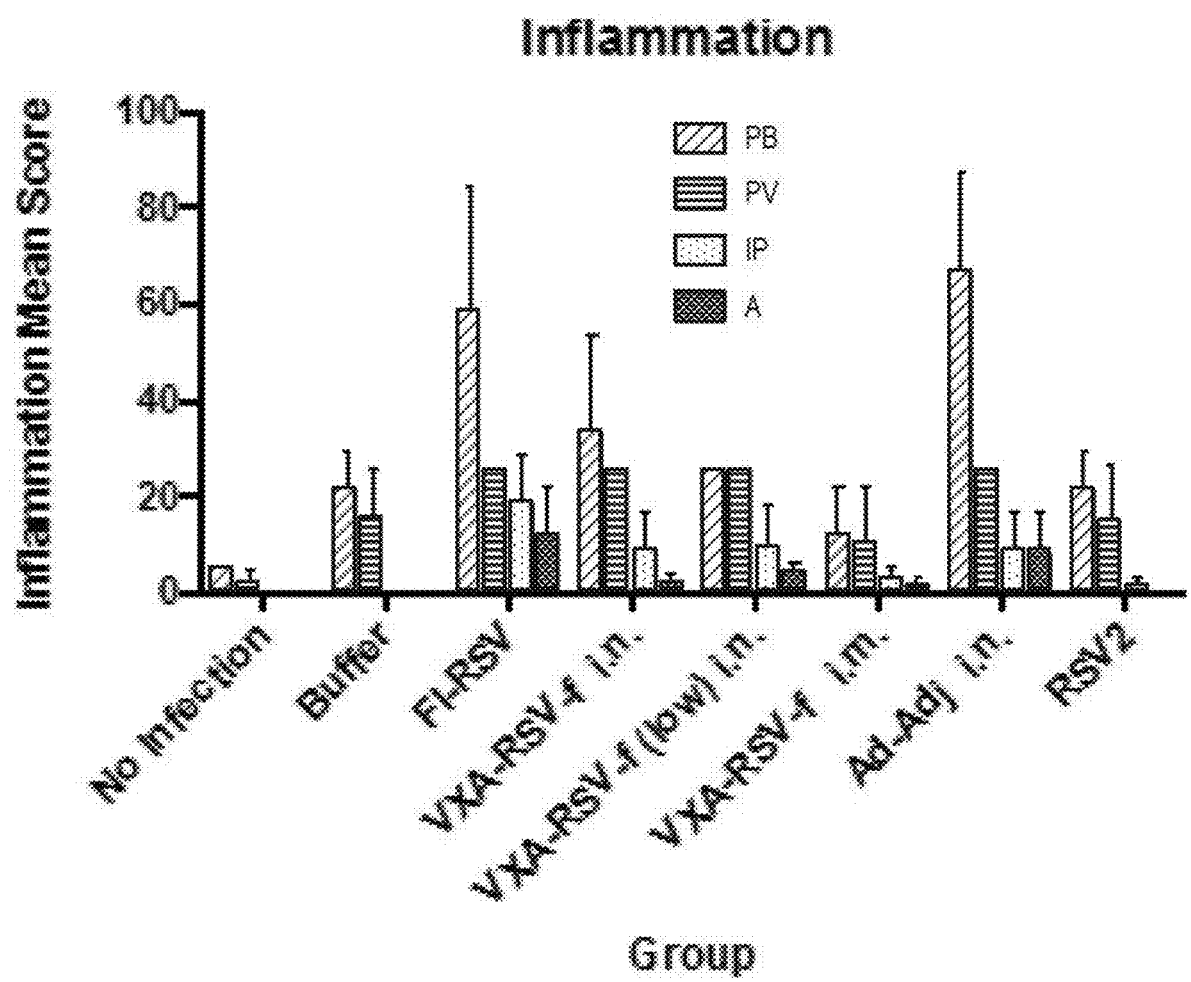
Figure 25C:
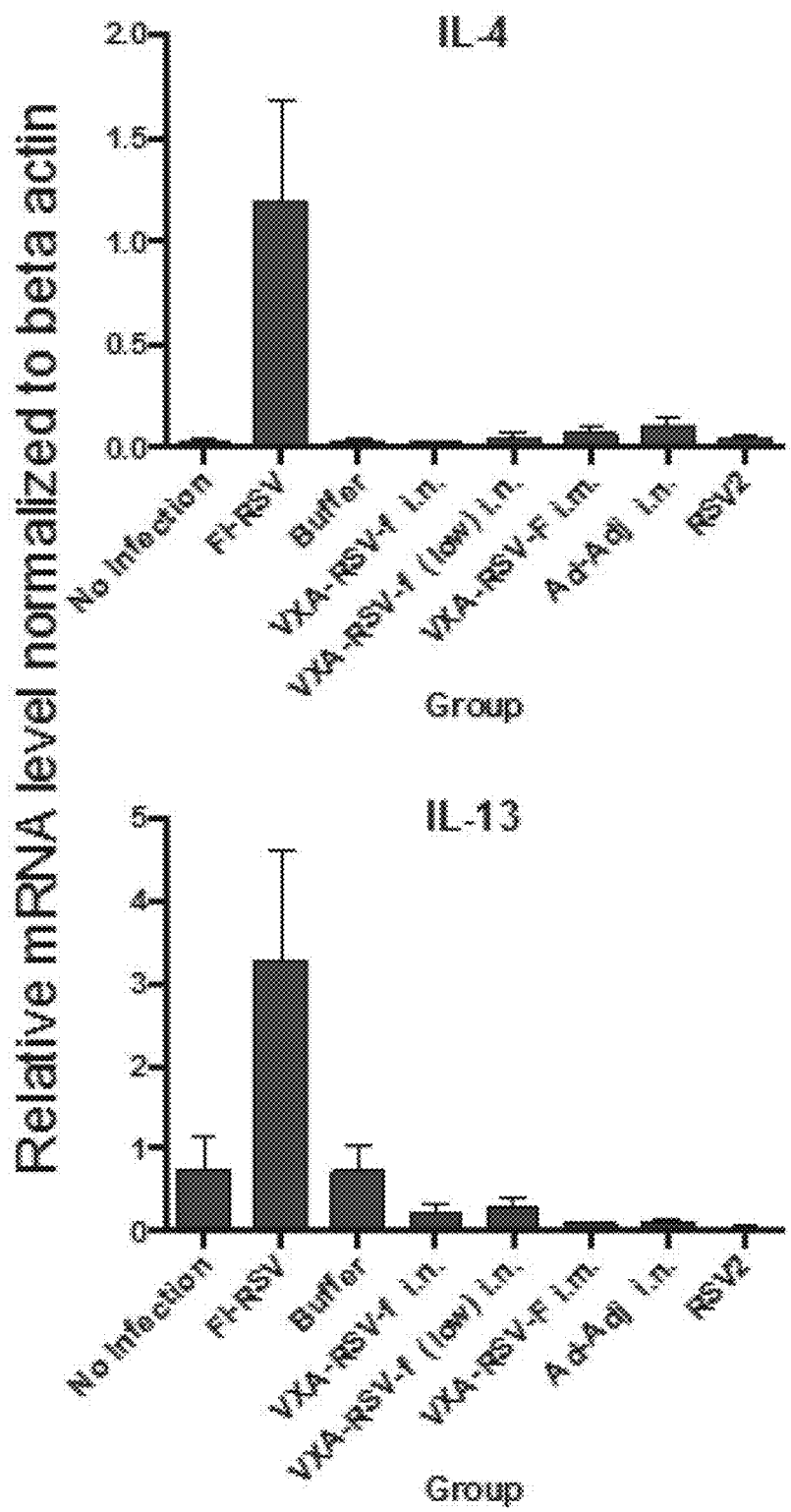

Lung inflammation was measured by immunohistology and qRT-PCR analysis on day 5 post RSV infection. Four different regions were assessed by immunohistology to determine if the vaccine led to adaptive immune enhancement of disease. The VXA-RSV-f vaccine did not induce significantly increased lung pathology scores for peribronchiolitis (PB), perivasculitis (PV), interstitial pneumonia (IP), and alveolitis (A) as compared to the FI-RSV vaccine, the "positive" control for lung inflammation (FIG. 25B), and did not lead to increases in the relative abundance of IL-4 or IL-13 (FIG. 25C). Groups given i.n. administration trended higher for PB and PV, including the Buffer, RSV2, and adjuvant control groups, but not necessarily for IP and A (FIG. 25B). The adjuvant group (without expression of RSV F protein) induced t high level of PB post RSV challenge, but induced only low levels of IP and A. Buffer and adjuvant alone control groups did not induce a significant increase in the relative abundance of IL-4 or IL-13 mRNA as the FI-RSV group did (FIG. 25B). The FI-RSV vaccine group induced an average relative abundance above 1 for IL-4 and above 3 for IL-13, compared to below 0.1 and 0.3 respectively for the VXA-RSV-f and RSV2 vaccine groups (FIG. 25C).

Figure 26A:
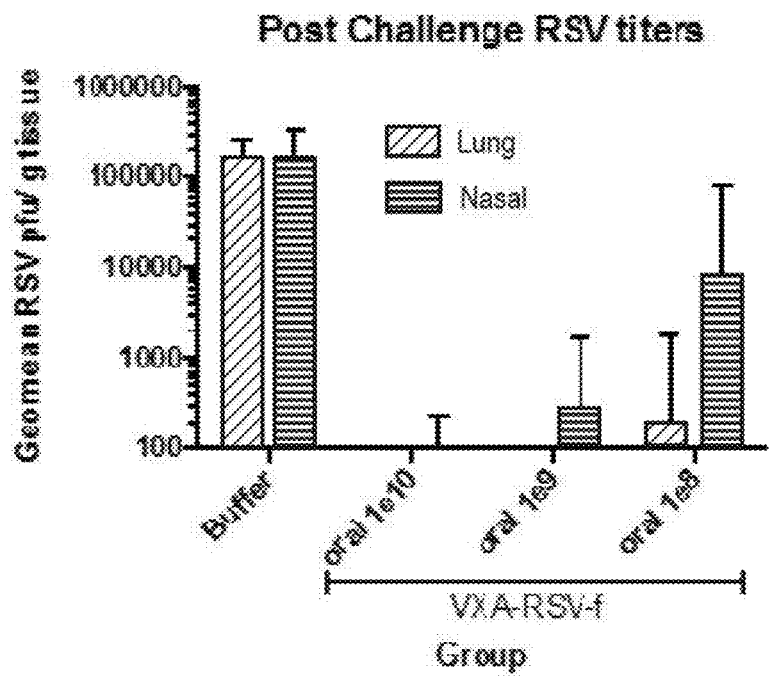
FIGS. 26A-26C shows oral immunization induces protection against RSV replication and disease. (Experiment XV-112).
Figure 26B:
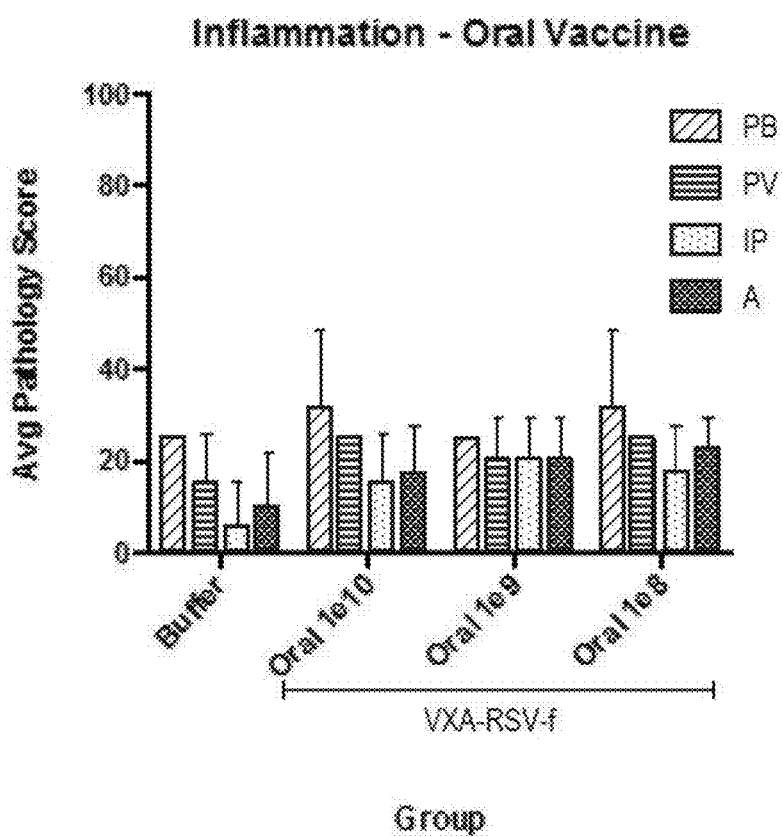
Figure 26C:
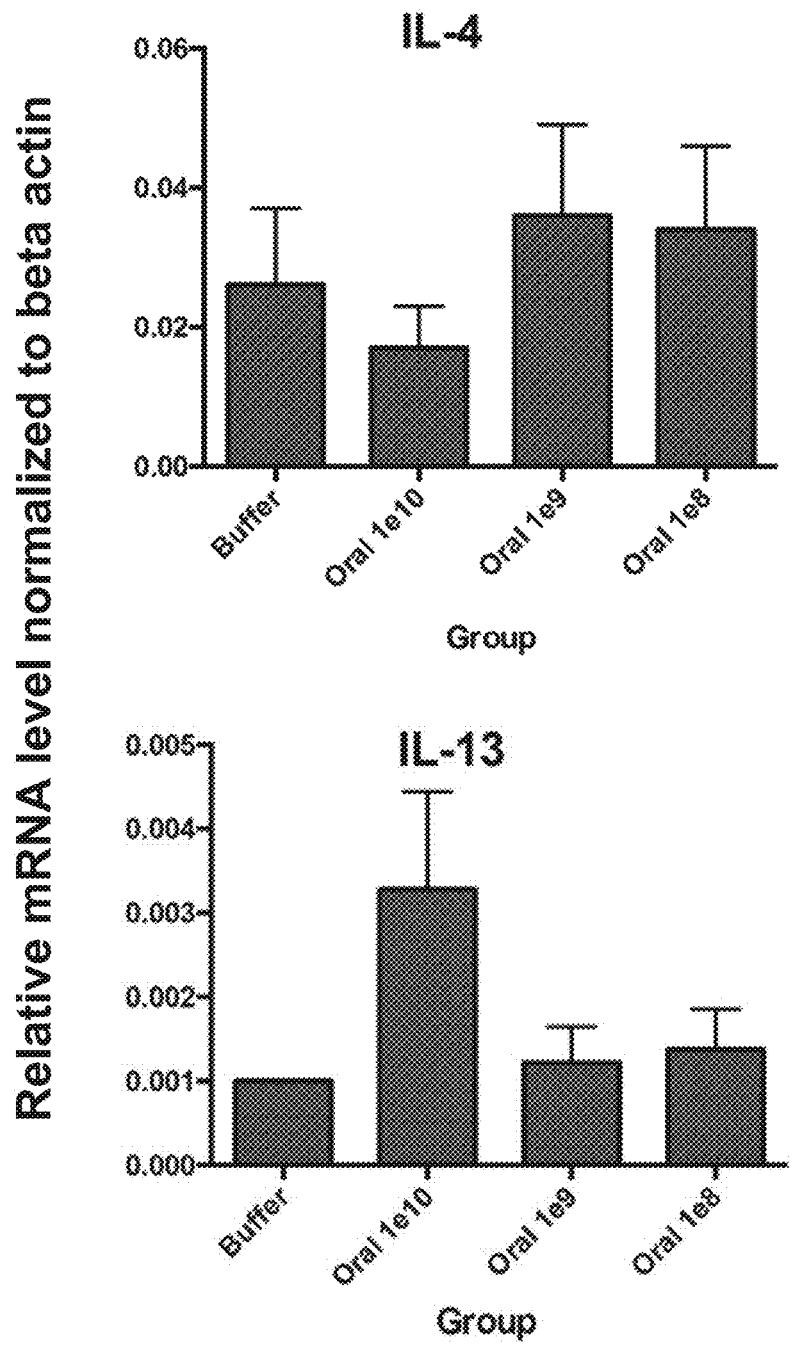

The oral cotton rat immunogenicity study (Study No. XV-112) was challenged with wild-type RSV because of the potent neutralizing antibody liters observed. Following immunization, cotton rats were given wild-type RSV strain A2 at $1 \times 10^5$ PFU at day 56. Lungs and nasal passages were harvested 5 days later and analyzed for the ability of the vaccines to protect against RSV replication and disease in cotton rat tissue. Oral immunization with the VXA-RSV-f vaccine induced dose dependent protection against RSV replication in both lungs and the nose, with the highest dose vaccine inducing complete protection in the lungs and nearly complete protection in the nose; 8 out of 8 animals were negative for RSV titers in the lungs and 7 of 8 animals were negative for RSV replication in the nose (FIG. 26A). Maximal replication (as seen in the buffer control group) had on average of 5.2 $\log_{10}$ PFU RSV/g of lung tissue, and vaccine induced immunity was able to reduce the post challenge RSV titers greater than 3 $\log_{10}$ for the $1 \times 10^9$ and $1 \times 10^{10}$ IU vaccine groups (FIG. 26A). The lowest dose group ($1 \times 10^8$ IU) also demonstrated substantial protection, with 6 of 8 animals having complete protection. Inflammation was assessed as before. The vaccine groups trended higher for inflammation compared to the buffer control group, but were not statistically different (FIG. 26B). Cytokine analysis of the lungs post challenge saw no substantial increase in the relative abundance of the IL-4 or IL-13 mRNA as measured by qRT-PCR. All vaccine and the buffer control groups had relative abundance levels of IL-4 and IL-13 mRNA below 0.04 and 0.005, respectively (FIG. 26C). These values are extremely low compared to the relative abundance levels of 1 and 3 for IL-4 and IL-13 respectively induced by the FI-RSV group in Study No. XV-95 (FIG. 25C), suggesting that no meaningful induction of these cytokines has occurred following oral delivery of VXA-RSV-f.

Example 9

High Titer Neutralizing Antibodies to Influenza Following Oral Tablet Immunization: A Randomized, Placebo-Controlled Trial Introduction Seasonal influenza vaccination requires substantial yearly campaigns to collect enough fertilized eggs and massive machinery to harvest and process each mini-egg bioreactor. Cell culture or plant derived hemagglutinin (HA) may reduce the burden of egg acquisition and processing, but these approaches still require expensive sterile fill and finish to produce individual syringe needles, that need to be disposed of as a biohazard. During a pandemic, schools can be closed and social distancing mandated, yet mass influenza immunization campaigns typically require lining up subjects at health clinics for injections. In order to circumvent this dilemma, oral influenza vaccines could be sent through the mail thus avoiding most human to human contact. Mail delivery is already used for a wide-variety of oral medications and has already been suggested as a means to deliver critical medicines to veterans during a pandemic. Further, tableting is a rapid, sanitary process that does not require the expensive sterile fill and finishing process that injected vaccines require.

Several adenoviral vector approaches have been attempted to enable oral influenza immunization. In 2011, a clinical trial using a cell-culture produced oral adenovirus vectored avian influenza (H5) vaccine was initiated. T cell responses to influenza H5 HA were measured in greater than 75% of subjects, but no neutralizing antibody responses were observed (Peters et al. Vaccine 2013; 31: 1752-8). After additional formulation development and dose optimization was performed, the clinical trial that is the subject of this report was initiated for seasonal influenza, using a tablet delivery format instead of a capsule. The same vector backbone was used as before, but with a new HA sequence from a strain similar to the H1N1 strain of the current commercial seasonal influenza vaccine (A/California/04/2009 (H1N1)) and with a 10 fold higher dose. A single dose of rAd-HA(A/CA/04/2009)-dsRNA was tested for safety and immunogenicity, in a double-blind, randomized, controlled clinical study. This report summarizes the findings of this trial.

Materials and Methods

Clinical Protocol and Enrollment

This was a phase 1, sequentially enrolled study, with a randomized and placebo-controlled cohort to evaluate safety, and immunogenicity of a recombinant Ad serotype 5 (rAd5) based oral vaccine against H1 seasonal influenza, The study was conducted in accordance with applicable Good Clinical Practice guidelines, the United States Code of Federal Regulations, and the International Conference on Harmonization guidelines. IRB approval was obtained from Aspire IRB (Santee, Calif.; AAHRPP accredited) before enrollment of subjects. Study participants were recruited using the CRO/Phase 1 Unit's existing volunteer database as well as using IRB approved advertising (print ads, radio ads and social media). Informed consent was obtained from all subjects after discussion of the study procedures and potential risks.

Subjects were pre-screened for Hemagglutination Inhibition (HAI) titers within 45 days of enrollment. In order to be eligible for study participation subjects had to have an initial HAI titer of <1:20, be between 18-49 years of age, and be in good health. Additional enrollment criteria are listed at clinicaltrials.gov under NCT01688297. The active phase of the trial was through day 28, with the follow-up phase for monitoring safety to continue for 1 year.

Randomization and Masking

The study was designed to evaluate the vaccine (VXA-A1.1) in 12 subjects at a single dose of 1×1011 infectious units (IU) with 12 subjects given a placebo control. There were 3 sequentially enrolled sentinel vaccine-treated subjects, with each subject dosed no more frequently than one every 24 h. After a week of monitoring for vaccine-related toxicities, the remaining subjects in the treated cohort (9) were randomized along with 12 placebo controls. Randomization was performed by computer generated assignment, and study drug was distributed with concealed identity to the blinded staff by the unblinded pharmacist. All investigative site staff as well as persons directly involved with immunological assays or the assessment of clinical safety remained blind to treatment assignments. All subjects were blinded in the study.

Sample Size

The overall number of volunteers per test group (n=12) was predicted to yield meaningful results. This was defined in a prior study as observing 50% of responders in the vaccine group and none in placebo group. With the sample size of 12 per group, there is 80% power to detect a group difference, assuming the proportion of response (defined as HAI>40) in vaccine group is 50% and in placebo is 0, using two-group Fisher's exact two-sided test at significance level of 0.05.

Vaccine

The rAd vector (non-replicating Ad5) carries DNA which encodes the HA (A/CA/04/2009) transgene whose expression is driven by a CMV promoter and a molecular dsRNA hairpin driven by a separate promoter, as described before (Scallan et al. Clinical and Vaccine Immunology 2013; 20(1): 85-94). GMP drug substance was produced in Wave Disposable Bioreactors (GE Healthcare, Waukesha, Wis.) at Lonza Biologicals (Houston, Tex.). Purification was performed by ion exchange chromatography, followed by buffer exchange. Purified vector was mixed with excipients, lyophilized, and then tableted at Lonza using microcrystalline cellulose and starch as tableting bulk. Tablets were enteric coated with Eudragit L100® (Evonik Industries, Darmstadt, Germany) using a Vector Hi-Coater system (Vector Freund, Cedar Rapids, Iowa). The final product was released in one lot, and titered by standard IU assay at Lonza. Placebo was prepared as similarly sized and shaped tablets containing 150 mg of microcrystalline cellulose, without enteric coating.

Safety Assessments

The principal investigator (PI) assessed solicited and unsolicited adverse events (AEs) in a blinded manner. The SMC oversaw the safety of the study but did not participate in the grading of AEs. Solicited AEs (reactogenicity) were collected with the aid of a 7-day solicited symptoms diary card. Unsolicited AEs (all other clinical AEs) were collected with the aid of an unsolicited diary card through Day 28. Investigators used the Center for Biologics Evaluation and Research (CBER) Guidance for Industry: Toxicity Grading Scale for Healthy Adult and Adolescent Volunteers Enrolled in Preventive Vaccine Trials, September 2007 to grade AEs.

Because of the novel adjuvant, we collected data on the occurrence of AEs of special interest (AESIs) and new onset of chronic illnesses (NOCIs). These include neuroinflammatory disorders, musculoskeletal disorders, gastrointestinal disorders, metabolic diseases, skin disorders and other autoimmune disorders. No AESIs or NOCIs have been reported through day 180 following immunization.

Endpoints

The primary endpoint for this study is safety and the secondary endpoint is immunogenicity through the active phase, primarily by HAI titers and HAI seroconversions. Additional immunological endpoints include MN titers and ASCs.

PBMC Isolation and Cryopreservation

Blood was collected in K3 EDTA Vacutainer® tubes (BD, Franklin Lakes, N.J.) and PBMCs were isolated the same day using Lymphoprep™ tubes (Axis-Shield, Norway).

PBMCs were frozen and thawed using serum free reagents according to the manufacturers instructions (Cellular Technology Ltd [CTL], Shaker Heights, Ohio).

Antibody Secreting Cells (ASCs)

Enzyme linked immunosorbent (ELISpot) kits for IgG and IgA secreting B cells were performed according to manufacturer's instructions (Mabtech, Mariemont, Ohio). Cells were cultured (between 1.5×10⁴ to 5×10⁵ cells per well) in triplicate wells, in CTL-Test medium to optimize spots. HA protein (Protein Sciences Corp, Meriden, Conn.) was biotinylated and quantitated at Vaxart using a biotinylation kit (Pierce, Rockford, Ill.). Spots were counted at Zellnet Consulting Inc (Fort Lee, N.J.).

Antibody Assays

HAI and MN Titers were performed by Focus Diagnostics (Cypress, Calif.) similarly as described previously (Greenberg et al. The New England Journal of Medicine 2009; 361(25): 2405-13). HAI and MN were measured against MDCK derived A/CA/07/2009 and egg derived A/CA/07/2009 respectively. HAI and MN titers less than 10 were marked as 5 as suggested by regulatory advice. Adenovirus neutralizing titers were measured as described before 2.

Statistical Analysis

In general, descriptive statistics for continuous variables included the number of subjects with data to be summarized (n), mean, standard error (std err), and 95% confidence intervals (95 CI). Titers were reported with geometric means and 95 CI. Categorical variables were presented using frequency counts and percentages. Treatment group differences were compared using two-group t test in continuous variables and Fisher's Exact test in categorical variables. All statistical tests were two-sided at a significance level of 0.05 without adjusting for multiplicity. An analysis of covariance (ANCOVA) model was used for (log transformed) HAI antibody titers, with Day 28 log-titer as dependent variable, treatment as a factor, and Day 0 log-titer as a covariate. Least square (LS) means, 95 CI of the LS means, difference of LS means and the 95 CI of the difference of LS means were obtained from the model. As an exploratory analysis for the HAI antibody titer, another ANCOVA model included age, sex, and body mass index (BMI) as covariates was performed as well.

Results

Figure 19:
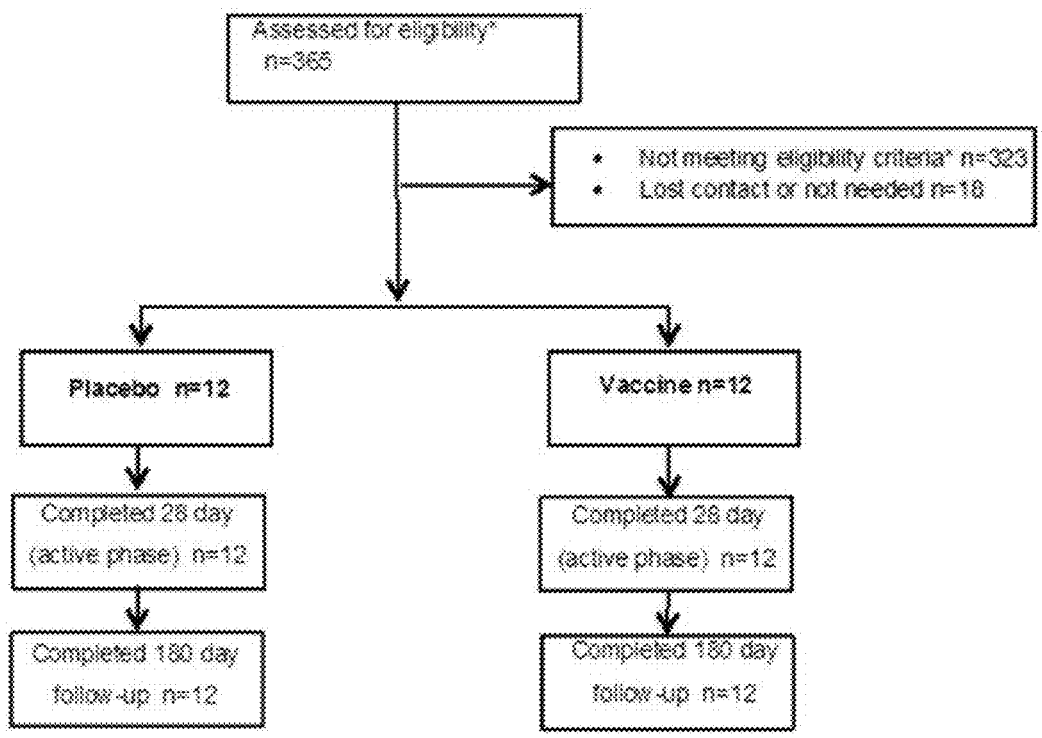
FIG. 19. Enrollment criteria for the study of "High Titer Neutralizing Antibodies to Influenza Following Oral Tablet Immunization: A Randomized, Placebo-controlled Trial." The major exclusion criteria are:
- positive for H1 influenza by HAI;
- has had an influenza vaccine in the past 2 years;
- current history of chronic alcohol consumption and/or illicit and/or recreational drug use;
- history of any confirmed or suspected immunodeficient or immunosuppressive condition;
- positive serology for HIV, HCV, or HBV;
- previous serious reactions to vaccination such as anaphylaxis, respiratory problems, hives, or abdominal pain;
- history of irritable bowel disease or other inflammatory digestive or gastrointestinal conditions that could affect the intended distribution of the vaccine targeting the mucosa of the small intestine;
- use of proton pump inhibitors (Nexium, Prilosec); and
- stool sample with occult blood at baseline exam.

Demographics 365 subjects were screened and 24 subjects were enrolled. All subjects that enrolled completed safety and immunogenicity assessments through the active phase, and through day 180 of the monitoring phase (FIG. 19). Demographics are described in Table 8 for both placebo and vaccine treated subjects.

Summary of Adverse Events

In the first 7 days following test article administration, there were 8 total solicited adverse events (AEs) reported in the VXA-A1.1 vaccine and placebo groups (Table 9). All of these AEs were grade 1 in severity. The investigator's assessment as to whether the AE was related to treatment is also indicated (Table 9). The most frequent AE was headache (2 in placebo, and 1 in the vaccine group). All other solicited AEs were single events (Table 9). There were a total of 8 unsolicited AEs in vaccine and placebo groups in the 28 days following immunization, with 3 events occurring in the placebo and 5 events occurring in the vaccine group. There were no serious adverse events reported in the study.

Clinical laboratory abnormalities were distributed across the vaccine and placebo groups. Of note, there were 6 neutropenic events in the vaccine group and 4 in the placebo group. These events occurred in a total of 8 subjects, 4 of who had pre-treatment neutropenic blood counts. Five of these subjects were also black or Japanese, which are ethnic groups that have a relatively high frequency of benign ethnic neutropenia (BEN). As is the case with (BEN), there were no clinical manifestations that resulted from any of the neutropenic events reported.

Immunogenicity Results

Figure 20A:
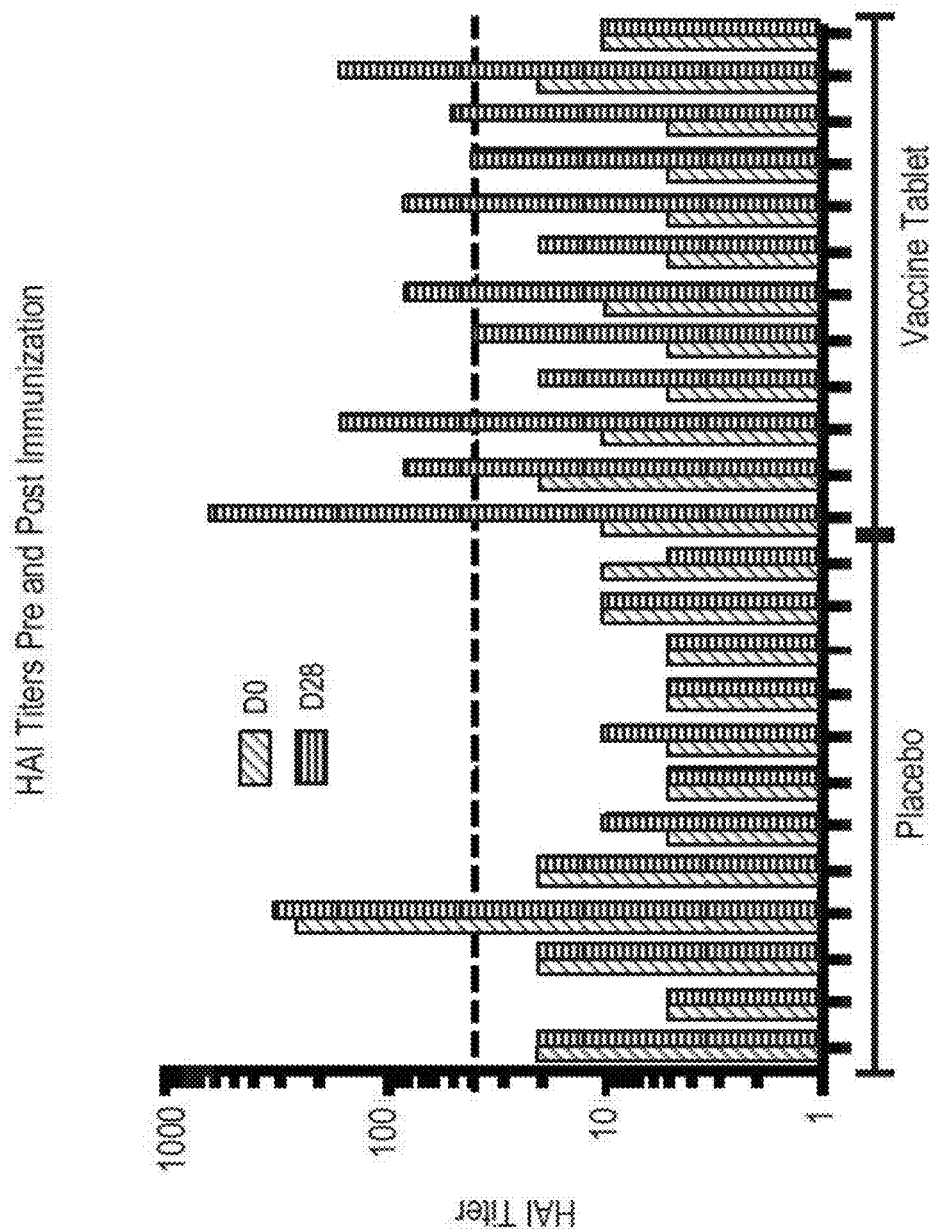
FIGS. 20A-20D. Antibody responses following a single oral immunization of a recombinant Ad serotype 5 (rAd5) based oral vaccine against H1 seasonal influenza.

HAI responses were measured on days 0 and 28 (FIG. 20A). No placebo treated subject seroconverted, but one placebo had a high day 0 value (which would have excluded the subject if measured at screening). None of the vaccine subjects had a starting HAI titer >20. After immunization, nine subjects in the vaccine group reached seroprotective levels (HAI ≥40) (FIG. 20A). Of the eleven 4-fold risers (92%), nine seroconverted (SC) with the other 2 subjects showing a 4-fold increase in HAI titer from 5 to 20. The vaccine group had a statistically significant increase in the number of 4-fold responders versus placebo (11 versus 0, with P<0.0000 by Fisher's Exact Test). Using an ANCOVA model accounting for the Day 0 log-titer as a covariant, the Geometric (LS) Mean Titer (GMT) for the vaccine group was calculated to be 71.5 (95 CI: 45-114) on Day 28, a 7.7-fold Geometric (LS) Mean Fold Rise (GMFR) over the initial GMT of 7.9 (95 CI: 4.6-13.6) on Day 0. The GMT on Day 28 for placebo group was 10.1 (95 CI: 6.4-16.2) on Day 28, a 1.1-fold GMFR over initial GMT of 11.0 (95 CI: 6.4-18.9) on Day 0. Comparing to placebo, the vaccine group had a statistically significant increase in GMT on Day 28 (p-value <0.001). The covariate effect of baseline was also statistically significant (p-value <0.001). An exploratory analysis was also carried out using another ANCOVA model, where additional covariates, age, sex and BMI were included. The effects of these covariates were not statistically significant on Day 28 [p-values: 0.993 (for age), 0.6% (for sex), 0.201 (for EMI)].

Durability of the antibody response was measured by examining HAI responses 180 days after immunization. In the vaccine-immunized group, 75% (9 of 12) of the subjects were seroprotected on day 28 and 75% (9 of 12) were still seroprotected on day 180. The HAI GMT were plotted (FIG. 20B), and the decrease in the GMT was found to be 29% between 28 and 180 days post immunization.

Figure 20B:
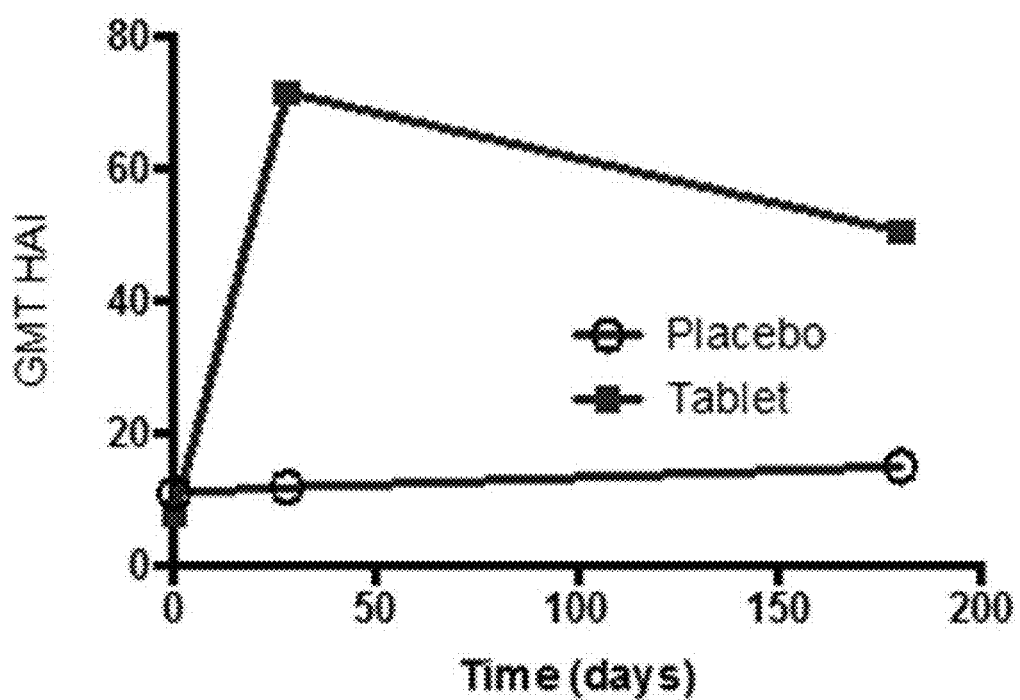
Figure 20C:
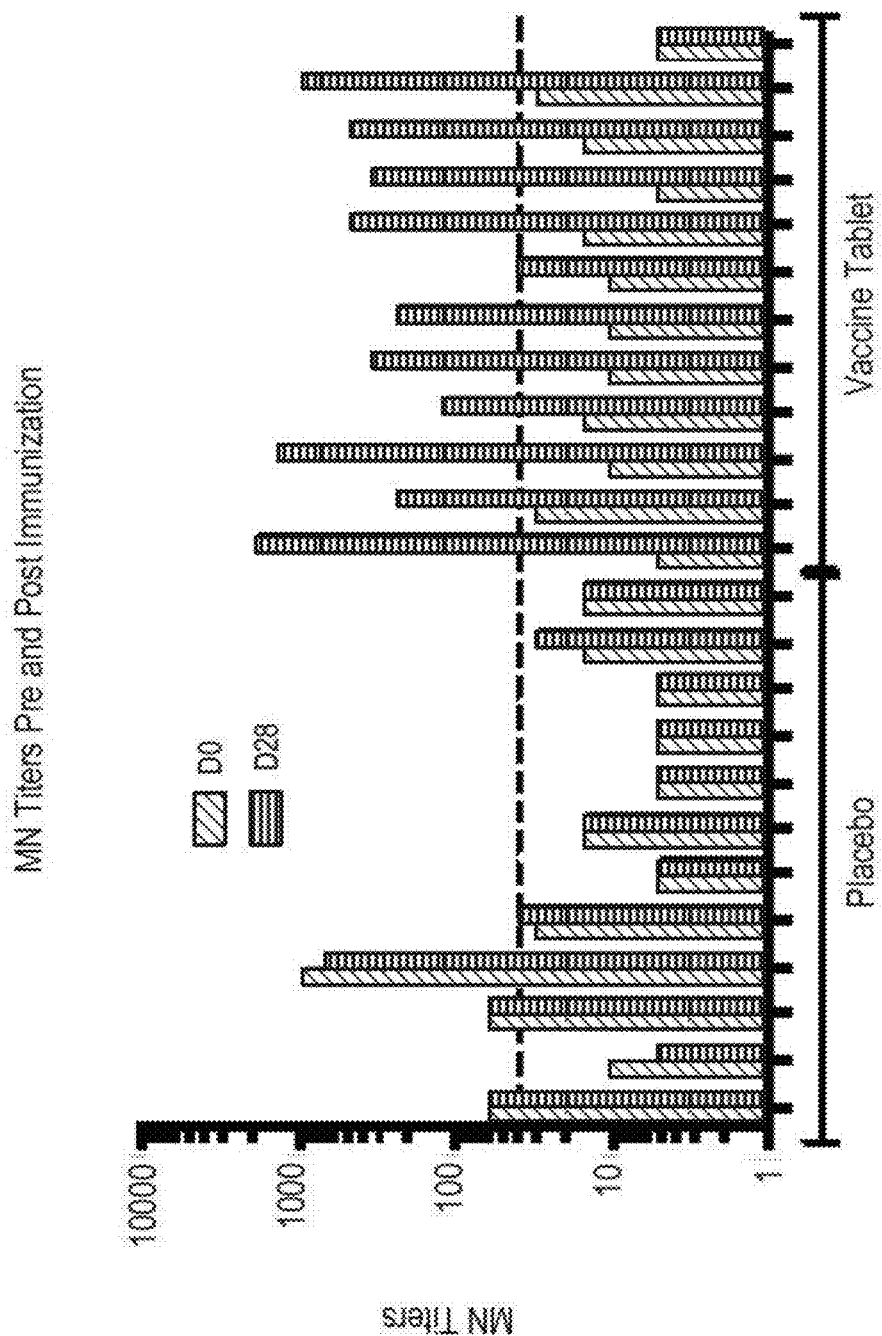

Neutralizing antibody responses to influenza were measured by MN assay. Significant increases in the MN titers in the treated group versus the placebo control were observed (FIG. 20C). The frequency of 4-fold MN responders in the vaccine treated group was significantly different than the placebo group, with 11 subjects responding in the vaccine treated group versus 0 in the placebo group (P<0.0000 by Fisher's exact test).

After removing subjects that had baseline MN titers (and HAI titers) greater than 40, the geometric mean titers (GMT) were calculated in the remaining subjects on days 0 and 28 (Table 10). The GMT for the vaccine group rose to 247 (95 CI: 89-685) versus no rise in the placebo for a day 28 GMT of 9.6 (95 CI: 5-18). These calculations had no impact on the vaccine group, as none of the subjects had high initial MN or HAI titers. These results show that neutralizing antibody titers to influenza are generated by oral immunization, with a greater than 20-fold increase in the GMT after immunization in the vaccine-treated group.

Figure 20D:
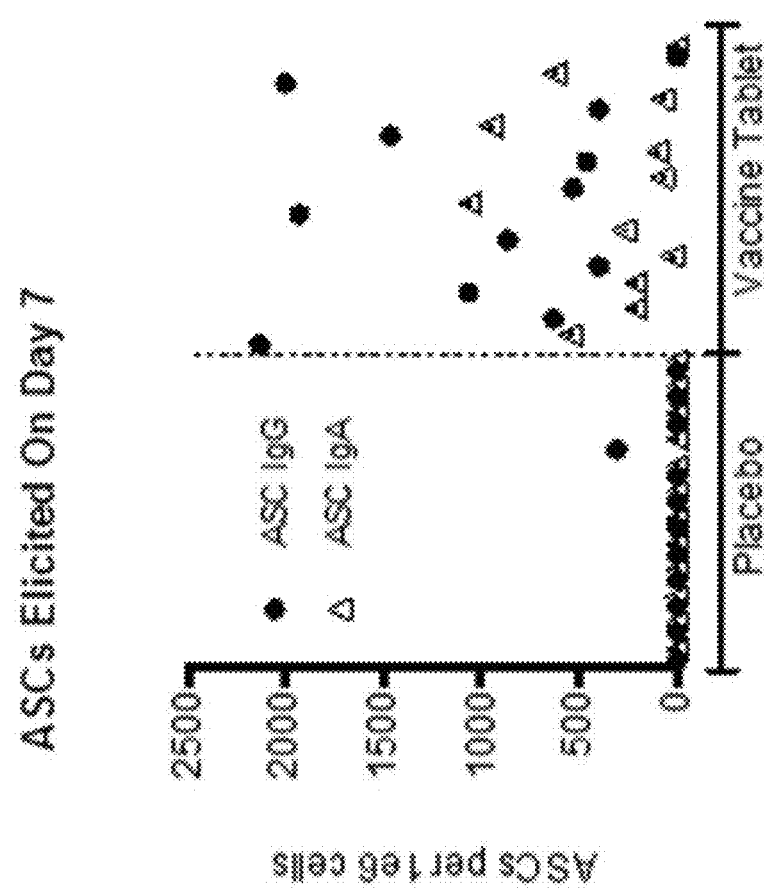

In order to measure total antibody responses to HA, the numbers of circulating pre-plasma B cells in peripheral blood were measured by ASC assay on days 0 and 7 after immunization. Results show that ASCs could be reliably measured on day 7 in the vaccine-treated group (FIG. 20D). Background ASCs were generally negligible on day 0. For the vaccine treated group, an average of 992 (+/−std err 209, 95 CI: 532-1452) IgG ASCs and 337 IgA ASCs (+/−std err 104, 95 CI: 117-580) each per 1×106 PBMC were found for day 7, with only one subject out of 12 having no detectable ASC response. The placebo group had no IgA spots on day 7, but one subject had a high background smear and a measurable IgG ASC response with smaller spots than normally observed. The treated group was significantly different than placebo in terms of the ability to elicit an IgG or an IgA ASC response at day 7 (P=0.0007 and P=0.008 respectively by T Test).

Subjects were measured for their anti-vector titers pre- and post-immunization. Following oral immunization, a few vaccine-treated subjects had an increase in neutralizing antibody responses to Ad5, which led to a 2.6-fold increase in the GM neutralizing antibody titers, compared to 1.0-fold GM fold rise in the placebo treated subjects. In the vaccine group, HAI and MN responses trended similarly for individual subjects. Eight subjects were Ad5 negative before immunization, and four were Ad5 positive before immunization. One subject that was Ad5 positive did not HAI seroconvert, however, one subject that was Ad5 positive had the highest increase in HAI titers (64 fold) of any of the subjects in the study (FIG. 21B). This same subject had a gain in MN titers of 362 fold (FIG. 21A) without any increase in the Ad5 neutralizing antibody titers pre and post immunization. There was no observed correlation between starting Ad5 titers versus fold MN response (or HAI response) for the subjects immunized with the tablet vaccine (FIGS. 21A and 21B).

Discussion

When the US military conducted an independent study to measure the effects of their seasonal vaccine campaigns on neutralizing antibody responses in military personnel, they reported a MN Titer GMFR of 5.6 after trivalent inactivated vaccine (TIV) injection and a GMFR of 2.2 following live-attenuated influenza vaccine (LAN) intranasal administration after accounting for subjects that had MN titers above 40 to start (Faix et al. PloS one 2012; 7(4): e34581). In this study, the MN GMFR was calculated at 29 for the 12 vaccine treated subjects (Table 10) with 92% of subjects showing a greater than 4-fold rise in MN titers. In the study by Gordon, et al, the SC rate to H1N1 was found to be 45% for one injection of 45 ug of HA protein (without adjuvant) (Gordon et al. Vaccine 2012; 30(36): 5407-16). This contrasts with the results published by Greenberg, et al, (supra) where the H1N1 vaccine was highly immunogenic and a 78% SC rate was observed after 1 dose of a split vaccine. In our tablet study, the HAI SC rate among vaccine treated subjects was 75% with over 92% of subjects having a 4-fold rise in HAI titers (FIG. 20A). It is not clear why our MN titers are much higher than the HAI liters. It is possible that the MN assay is just more sensitive or that the oral rAd based vaccine elicits stronger neutralizing responses outside the head region than protein injected vaccines. In either case, our early stage results suggest that an oral tablet vaccine would be competitive with existing vaccines in terms of eliciting neutralizing antibody responses to influenza.

Individuals with pre-existing immunity to influenza H1N1 were excluded from study participation. This was helpful in analysis of immune responses in this Phase 1 study to better understand effects of the vaccine. In practice, in the "real world", individuals with and without pre-existing immunity to influenza are immunized. Enrollment in Phase 2 and 3 studies will include individuals with and without detectable antibody levels to vaccine antigen at baseline.

HAI responses are elicited with injected commercial vaccines, but HAI titers are known to wane. In a study by Crum-Cianflone, et al, non-HIV infected volunteers had a 67% drop in GMT HAI titers between 1 and 6 months post immunization (Crum-Cianflone et al. Vaccine 2011; 29(17): 3183-91). Similarly, the percentage of seroprotected subjects dropped from 75% to 56% for HIV negative subjects that enrolled with seronegative HAI titers (≤1:10)10. Studies with pandemic influenza vaccines have also shown decreases in durability. In the AS03 avian influenza vaccine study by Leroux-Roels, et al, the GMT reached 563 after 2 vaccine doses, but at 6 months post immunization, the GMT had dropped to 18, a 96% decrease (Leroux-Roels et al. Vaccine 2010; 28(3): 849-57). In our tablet vaccine study that enrolled seronegative subjects (all subjects ≤1:20), the percentage of seroprotected subjects remained constant at 75% at 1 and 6 months post immunization, and the HM GMT titer drop was less dramatic showing only a 29% decrease (FIG. 20B). While unproven, one possibility is that the durability is better for vector-based vaccines because of enhanced T cell responses. These preliminary data are at least encouraging that the tablet vaccine can provide antibody durability.

The numbers of clinical reported adverse events were similar to those observed before fa other adenoviral vectored based vaccines of the invention. In this study, 17 clinical adverse events were reported though day 28 following immunization and are reasonably evenly distributed between placebo and treated groups. In a published study of an recombinant adenovirus EBOV vaccine injected into humans, the frequency of any adverse event was 55% among vaccine recipients and 25% among placebo recipients, with the most common reported adverse event being headaches (55%), myalgia (46%), and chills (27%) in the high dose vaccine group (Ledgerwood et al. Vaccine 2010; 29(2): 304-13). The most frequently reported adverse event in our vaccine tablet study was headache (reported in 1 vaccine and 2 placebo subjects).

Although Ad5 immunity can be an issue with injected vaccines, it may not be the case with oral immunization with a non-replicating vector where neutralizing antibody titers do not seem to hinder performance (Xiang et al. Journal of virology 2003; 77(20): 10780-9). The ability to elicit a neutralizing immune response to influenza did not appear to be impacted after oral immunization with the vaccine tablet (FIG. 21). One of the subjects with the highest anti-Ad5 titer to start had the highest measured increase in neutralizing antibody responses by MN and HAI assay (FIG. 21). While i.m. immunization can cause 100% Ad5 seroconversion and GMTs to rise greater than 50 fold (estimated from FIG. 2b from O'Brien et al. Nat Med 2009; 15(8): 873-5), the increase in neutralizing titers with the 1×1011 IU tablet were much more modest. Oral immunization appears to lead to a much more selective increase in the immune response to transgene compared to vector with a GMT MN titer rise of 29 compared to Ad5 titer increase of 2.6. In contrast to results with non-replicating Ad5 based vaccine in humans, oral administration of replicating vectors shows the opposite trend where the antibody responses to the vector far exceeds the antibody responses to transgene. As an example, in an oral replicating Ad4-HA study, 80% of subjects seroconverted to Ad4 on the first immunization, but did not have significant neutralizing antibody responses to HA after 3 immunizations (with a maximum of 19% SC in a vaccine group) (Gurwith et al. The Lancet infectious diseases 2013; 13(3): 238-50).

An oral formulation could greatly facilitate vaccine administration, particularly during a pandemic when rapid distribution is needed. During the 2009 H1N1 pandemic, when vaccine was in short supply, individual county health departments in California had to have a plan for distribution. In Los Angeles County, approximately 60 points of distribution (PODs) were tasked to administer the vaccine. Approximately 247 persons per hour lined up, and the rate of immunization was approximately 239 person per hour at each POD (Saha et al. Emerging infectious diseases 2014; 20(4): 590-5). For the PODs in Los Angeles County, this translated to 143,000 people per day. In a city of 9 million, assuming supplies or qualified personnel were not in short supply, it would take more than 60 days to complete an immunization campaign. As an alternative, if the H1N1 pandemic vaccine was delivered by US mail and self-administered by tablet, all 9 million subjects could be immunized within a single day without people having to stand in line, and risking exposure to the growing outbreak. While there are regulatory hurdles to overcome, our tablet vaccine appears to be stable at room temperature for greater than 270 days and can tolerate short-term excursions at higher temperatures (G. Trager, unpublished data), which should make this approach technically feasible.

In summary, oral influenza vaccine based on rAd administration can elicit antibody responses to influenza in greater than 90% of subjects. While this is an early clinical stage study and several studies will need to be completed that address issues such as interference and repeated seasonal use, these results look encouraging for safety and immunogenicity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, websites, and database accession entries cited herein are hereby incorporated by reference in their entirety for all purposes.

REFERENCES

1. Kariko K, Bhuyan P, Capodici J, Weissman D. 2004. Small interfering RNAs mediate sequence-independent gene suppression and induce immune activation by signaling through toll-like receptor 3. J Immunol 172:6545-6549.
2. Boukhvalova M S, Blanco J C. 2013. The cotton rat *Sigmodon hispidus* model of respiratory syncytial virus infection. Curr Top Microbiol Immunol 372:347-358.
3. Prince G A, Curtis S J, Yim K C, Porter D D. 2001. Vaccine-enhanced respiratory syncytial virus disease in cotton rats following immunization with Lot 100 or a newly prepared reference vaccine. J Gen Virol 82:2881-2888.
4. Liebowitz D, Lindblom J D, Brandl J R, Garg S J, Tucker S N. 2015. High Titer Neutralizing Antibodies to Influenza Following Oral Tablet Immunization: A Randomized, Placebo-controlled Trial Lancet Infect Dis 15:1041-1048.
5. Schagen F H, Rademaker H J, Fallaux F J, Hoeben R C. 2000. Insertion vectors for gene therapy. Gene Ther 7:271-272.
6. Harui A, Suzuki S, Kochanek S, Mitani K. 1999. Frequency and stability of chromosomal integration of adenovirus vectors. J Virol 73:6141-6146.
7. Russell W C. 2000. Update on adenovirus and its vectors. J Gen Virol 81:2573-2604.
8. Paielli D L, Wing M S, Rogulski K R, Gilbert J D, Kolozsvary A, Kim J H, Hughes J, Schnell M, Thompson T, Freytag S O. 2000. Evaluation of the biodistribution, persistence, toxicity, and potential of germ-line transmission of a replication-competent human adenovirus following intraprostatic administration in the mouse. Mol Ther 1:263-274.
9. Sheets R L, Stein J, Bailer R T, Koup R A, Andrews C, Nason M, He B, Koo E, Trotter H, Duffy C, Manetz T S, Gomez P. 2008. Biodistribution and toxicological safety of adenovirus type 5 and type 35 vectored vaccines against human immunodeficiency virus-1 (HIV-1), Ebola, or Marburg are similar despite differing adenovirus serotype vector, manufacturer's construct, or gene inserts. J Immunotoxicol 5:315-335.
10. Thou D, Cun A, Li Y, Xiang Z, Ertl H C. 2006. A chimpanzee-origin adenovirus vector expressing the rabies virus glycoprotein as an oral vaccine against inhalation infection with rabies virus. Mol Thor 14:662-672.
11. Scallan C D, Tingley D W, Lindbloom J D, Toomey J S, Tucker S N. 2013. An adenovirus-based vaccine with a double-stranded RNA adjuvant protects mice and ferrets against H5N1 avian influenza in oral delivery models. Clin Vaccine Immunol 20:85-94.

What is claimed is:

1. An immunogenic composition for eliciting serum IgG and intestinal secretory IgA immune responses in a human, the composition comprising:
   (i) an E1/E3-deleted replication-incompetent serotype 5 adenoviral vector comprising a nucleic acid sequence encoding a viral protein 1 (VP1) polypeptide of norovirus and a nucleic acid sequence encoding a dsRNA adjuvant, encompassed by (ii) an enteric coating having a threshold pH of 5.8-7.0 that directs delivery and release of the adenoviral vector to the ileum of the human;
   wherein the nucleic acid encoding the VP1 polypeptide has at least 90% identity to SEQ ID NO:3 or at least 90% identity to SEQ ID NO:1.

2. The immunogenic composition of claim 1, wherein the VP1 polypeptide has at least 95% identity to SEQ ID NO:4 or SEQ ID NO:2.

3. The immunogenic composition of claim 1, wherein the VP1 polypeptide is encoded by a nucleic acid sequence having at least 95% identity to SEQ ID NO:3 or at least 95% identity to SEQ ID NO:1.

4. The immunogenic composition of claim 1, wherein the VP1 polypeptide is encoded by a nucleic acid sequence having at least 98% identity to SEQ ID NO:3 or at least 98% identity to SEQ ID NO:1.

5. The immunogenic composition of claim 1, wherein enteric coating has a threshold pH of 5.9-6.1.

6. The immunogenic composition of claim 1, wherein the dsRNA adjuvant is a TLR3 agonist.

7. The immunogenic composition of claim 1, wherein the enteric coating comprises poly(methacrylic acid-co-methyl methacrylate) 1:1.

8. The immunogenic composition of claim 1, wherein the enteric coating comprises a mixture of poly(methacrylic acid-co-methyl methacrylate) 1:1 and poly(methacrylic acid-co-ethyl acrylate) 1:1.

9. The immunogenic composition of claim 8, wherein the ratio of poly(methacrylic acid-co-methyl methacrylate) 1:1 to poly(methacrylic acid-co-ethyl acrylate) 1:1 is 1:4 to 4:1.

10. The immunogenic composition of claim 1, wherein the enteric coating comprises poly(methacrylic acid-co-methyl methacrylate) 1:1 and poly(methacrylic acid-co-methyl methacrylate) 1:2.

11. The immunogenic composition of claim 1, wherein the ratio of poly(methacrylic acid-co-methyl methacrylate) 1:1 to poly(methacrylic acid-co-methyl acrylate) 1:2 is 1:2 to 2:1.

12. The immunogenic composition of claim 1, wherein the enteric coating comprises a mixture of poly(methacrylic acid-co-methyl methacrylate) 1:2 and poly(methacrylic acid-co-ethyl acrylate) 1:1.

13. The immunogenic composition of claim 12, wherein the ratio of poly(methacrylic acid-co-methyl methacrylate) 1:2 to poly(methacrylic acid-co-ethyl acrylate) 1:1 is 1:4 to 4:1.

14. The immunogenic composition of claim 1, wherein the composition is in the form of a compressed tablet.

15. An expression vector comprising a heterologous nucleic acid encoding a viral protein 1 (VP1) of norovirus, wherein the heterologous nucleic acid comprises a nucleic acid sequence having at least 90% identity to SEQ ID NO:3 or SEQ ID NO:1.

16. The expression vector of claim 11, wherein the nucleic acid sequence has at least 95% identity to SEQ ID NO:3 or SEQ ID NO:1.

* * * * *

SEQUENCE LISTING

<160> NUMBER OF SEQ ID NOS: 11

<210> SEQ ID NO 1
<211> LENGTH: 1593
<212> TYPE: DNA
<213> ORGANISM: Artificial Sequence
<220> FEATURE:
<223> OTHER INFORMATION: synthetic nucleotide sequence - Codon optimized
      DNA encoding the 58 kd capsid protein [Norwalk virus] (insert in
      VXA-G1.1-NN)

<400> SEQUENCE: 1

| | | | | | |
|---|---|---|---|---|---|
| atgatgatgg | cgagtaaaga | cgctacatcc | tccgtggatg | gggcctctgg | agcaggtcag | 60 |
| ctggtgccgg | aggtgaacgc | atcagatcct | cttgctatgg | acccagtggc | aggaagcagt | 120 |
| actgcagtcg | ctactgctgg | acaagtaaat | cccatcgatc | cctggatcat | caataacttc | 180 |
| gtgcaggccc | cacaaggcga | atttactatt | tcccccaaca | cacgcctgg | cgatgtgttg | 240 |
| ttcgatctgt | ctcttggccc | ccatctgaac | ccctttctgt | tgcatctctc | ccagatgtac | 300 |
| aatggctggg | tggcaatat | gcgcgtgcgc | attatgttgg | ccggtaacgc | gtttacagct | 360 |
| ggaaaaataa | tcgtgagctg | cattcctccc | ggcttcggtt | cccataatct | gacaatagcg | 420 |
| caggctaccc | tgttccctca | cgtgatcgcg | gatgtgagaa | cacttgatcc | catagaggtg | 480 |
| cctctggaag | acgtgagaaa | tgtcttgttc | cataataatg | accggaatca | acaaacaatg | 540 |
| aggctggtgt | gcatgttgta | cacacctctg | cggacgggcg | gcggaacagg | ggactcattt | 600 |
| gtagtggcag | gaagagtgat | gacctgccct | tctcccgact | tcaatttcct | gttttttggtt | 660 |
| cctcccacag | tcgagcagaa | gactaggcca | tttaccctgc | ccaatctccc | gcttagctca | 720 |
| ctgtctaatt | caagagcacc | gctgccaatt | tcttcaatgg | gcatttcccc | ggacaatgtg | 780 |
| cagtccgttc | aattccagaa | cggcaggtgt | acgctggatg | gcagacttgt | cggcactaca | 840 |
| ccggtcagcc | tctcacacgt | tgccaaaatt | cggggtactt | ccaacggcac | ggtcatcaac | 900 |
| ttgaccgagc | tggacgggac | cccgttccac | cccttgagg | gccccgctcc | tatcgggttt | 960 |
| cccgatctgg | gagggtgtga | ttggcacatc | aacatgacac | agtttgggca | tagctcacag | 1020 |
| acgcagtacg | acgtcgatac | caccctgac | acattcgtgc | cgcatctcgg | ctcaatccag | 1080 |
| gcaaacggca | tagggagtgg | taattatgtc | ggtgtcttga | gttggatctc | tccgccctct | 1140 |
| caccttccg | gttcccaagt | agacctctgg | aagatcccca | attacggctc | ctctatcacc | 1200 |
| gaggccaccc | acttggcccc | atccgtctat | cccccaggat | tcgggaggt | actcgttttc | 1260 |
| ttcatgagta | agatgcctgg | tcctggcgcc | tacaatctgc | cttgcttgtt | gccccaggag | 1320 |
| tacattagcc | acctggcctc | tgaacaggcc | ccaccgtgg | gagaagccgc | tttgttgcat | 1380 |
| tacgtcgacc | ccgacaccgg | tagaaacctg | ggagagttta | agcatatcc | tgatgggttc | 1440 |
| cttacctgcg | tgcccaatgg | cgcatcatct | ggccccagc | agctgccgat | caatggcgtt | 1500 |
| ttcgtctttg | tgtcctgggt | atcccgcttc | taccagctga | agccggttgg | cacagcctca | 1560 |
| tcagcacgcg | gcagactggg | cctcagaaga | taa | | | 1593 |

<210> SEQ ID NO 2
<211> LENGTH: 530
<212> TYPE: PRT
<213> ORGANISM: Unknown
<220> FEATURE:
<223> OTHER INFORMATION: Norwalk virus - 58 kd capsid protein

<400> SEQUENCE: 2

Met Met Met Ala Ser Lys Asp Ala Thr Ser Ser Val Asp Gly Ala Ser

-continued

```
1               5               10              15
Gly Ala Gly Gln Leu Val Pro Glu Val Asn Ala Ser Asp Pro Leu Ala
                20              25              30

Met Asp Pro Val Ala Gly Ser Ser Thr Ala Val Ala Thr Ala Gly Gln
            35              40              45

Val Asn Pro Ile Asp Pro Trp Ile Ile Asn Asn Phe Val Gln Ala Pro
        50              55              60

Gln Gly Glu Phe Thr Ile Ser Pro Asn Thr Pro Gly Asp Val Leu
 65              70              75              80

Phe Asp Leu Ser Leu Gly Pro His Leu Asn Pro Phe Leu Leu His Leu
                85              90              95

Ser Gln Met Tyr Asn Gly Trp Val Gly Asn Met Arg Val Arg Ile Met
            100             105             110

Leu Ala Gly Asn Ala Phe Thr Ala Gly Lys Ile Ile Val Ser Cys Ile
            115             120             125

Pro Pro Gly Phe Gly Ser His Asn Leu Thr Ile Ala Gln Ala Thr Leu
        130             135             140

Phe Pro His Val Ile Ala Asp Val Arg Thr Leu Asp Pro Ile Glu Val
145             150             155             160

Pro Leu Glu Asp Val Arg Asn Val Leu Phe His Asn Asn Asp Arg Asn
                165             170             175

Gln Gln Thr Met Arg Leu Val Cys Met Leu Tyr Thr Pro Leu Arg Thr
            180             185             190

Gly Gly Gly Thr Gly Asp Ser Phe Val Val Ala Gly Arg Val Met Thr
            195             200             205

Cys Pro Ser Pro Asp Phe Asn Phe Leu Phe Leu Val Pro Pro Thr Val
        210             215             220

Glu Gln Lys Thr Arg Pro Phe Thr Leu Pro Asn Leu Pro Leu Ser Ser
225             230             235             240

Leu Ser Asn Ser Arg Ala Pro Leu Pro Ile Ser Ser Met Gly Ile Ser
                245             250             255

Pro Asp Asn Val Gln Ser Val Gln Phe Gln Asn Gly Arg Cys Thr Leu
            260             265             270

Asp Gly Arg Leu Val Gly Thr Thr Pro Val Ser Leu Ser His Val Ala
            275             280             285

Lys Ile Arg Gly Thr Ser Asn Gly Thr Val Ile Asn Leu Thr Glu Leu
        290             295             300

Asp Gly Thr Pro Phe His Pro Phe Glu Gly Pro Ala Pro Ile Gly Phe
305             310             315             320

Pro Asp Leu Gly Gly Cys Asp Trp His Ile Asn Met Thr Gln Phe Gly
                325             330             335

His Ser Ser Gln Thr Gln Tyr Asp Val Asp Thr Thr Pro Asp Thr Phe
            340             345             350

Val Pro His Leu Gly Ser Ile Gln Ala Asn Gly Ile Gly Ser Gly Asn
            355             360             365

Tyr Val Gly Val Leu Ser Trp Ile Ser Pro Pro Ser His Pro Ser Gly
        370             375             380

Ser Gln Val Asp Leu Trp Lys Ile Pro Asn Tyr Gly Ser Ser Ile Thr
385             390             395             400

Glu Ala Thr His Leu Ala Pro Ser Val Tyr Pro Pro Gly Phe Gly Glu
                405             410             415

Val Leu Val Phe Phe Met Ser Lys Met Pro Gly Pro Gly Ala Tyr Asn
            420             425             430
```

```
Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530
```

<210> SEQ ID NO 3
<211> LENGTH: 1623
<212> TYPE: DNA
<213> ORGANISM: Artificial Sequence
<220> FEATURE:
<223> OTHER INFORMATION: synthetic nucleotide sequence - Codon Optimized sequence encoding Norovirus Hu/GII.4/Sydney/NSW0514/2012/AU (insert in VXA-G2.4-NS)

<400> SEQUENCE: 3

```
atgaagatgg ctagcagcga tgccaatccg agtgatgggt ccgcagccaa tctggtcccg     60
gaggttaaca atgaagtgat ggctctggaa cctgtggtgg gtgctgcaat cgccgcacct    120
gttgcagggc agcagaacgt tattgatccc tggatcagga acaacttcgt gcaagcaccc    180
ggcggtgaat tcaccgtgag ccccaggaac gccccaggcg aaattctgtg gtctgcccca    240
ctggggcctg atctgaaccc ctatctgtct cacctggcaa gaatgtataa cgggtatgcc    300
ggagggtttg aggtccaggt catcctggcg ggaaacgcct ttactgcagg caaggtgata    360
tttgcggccg tacctcccaa ttttccaacc gagggactta gcccatccca ggtgacaatg    420
tttcctcaca tcgtggtcga tgtgcgccag cttgagccag tcctgattcc actgccagac    480
gtgagaaata acttttatca ttacaatcaa tcaaacgacc caaccatcaa actgatcgcc    540
atgctgtaca ctcctcttcg cgccaacaac gctggtgacg atgtgtttac agtgtcttgt    600
cgggtcctca ctcgcccctc cccagatttt gactttattt ttctcgtgcc gccaacggtt    660
gaaagtagga caaagccttt ctccgtacca gtgctcactg tggaggagat gaccaacagc    720
cggtttccga tccctctgga gaaactgttc acggggcctt ctagtgcttt cgtggttcag    780
ccacaaaacg ggaggtgcac cacagatggc gtactgcttg ggactaccca gcttagcccc    840
gtgaatattt gtaccttccg gggggatgtg acacacatta ccggctccag gaactatacc    900
atgaatctgg cctcccaaaa ttggaacgac tatgatccca ccgaggagat ccctgcccct    960
ctgggcactc ctgactttgt tggaaagata cagggcgtcc tgacacaaac aacaagaacc   1020
gatggctcta cccgggggca taaggcaacc gtgtacactg ggtccgctga ctttgcgccc   1080
aaactgggac gggtccaatt cgagactgac acagaccgag acttcgaggc gaatcagaac   1140
acaaagttca cccctgtcgg tgtgattcag gacgggggca ccactcatcg gaacgagccc   1200
caacagtggg tcttgccctc ctactccggg aggaatactc acaatgttca cctggccccc   1260
gccgtggccc ccacgttccc aggtgaacaa ctgctgtttt ttagatctac tatgcctggt   1320
tgttccggct atccaaacat ggaccttgat tgtctgctgc cacaggagtg ggtgcagtat   1380
```

```
ttctaccagg aagcagcccc agcccagtca gatgttgcct tgcttcggtt cgtgaatcct   1440
gataccggga gggttctctt cgaatgcaag ctgcacaaat ctggctacgt gacggtagcg   1500
catactggac agcatgacct cgtcattccc ccaaacggat actttcgatt cgatagctgg   1560
gtaaaccagt tttatacact ggcacctatg ggcaacggga ccggcaggag gcgggcggtg   1620
taa                                                                 1623
```

<210> SEQ ID NO 4
<211> LENGTH: 540
<212> TYPE: PRT
<213> ORGANISM: Unknown
<220> FEATURE:
<223> OTHER INFORMATION: Norovirus Hu/GII.4/Sydney/NSW0514/2012/AU

<400> SEQUENCE: 4

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
```

```
                305                 310                 315                 320
Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
                340                 345                 350

Thr Gly Ser Ala Asp Phe Ala Pro Lys Leu Gly Arg Val Gln Phe Glu
                355                 360                 365

Thr Asp Thr Asp Arg Asp Phe Glu Ala Asn Gln Asn Thr Lys Phe Thr
            370                 375                 380

Pro Val Gly Val Ile Gln Asp Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
                420                 425                 430

Phe Phe Arg Ser Thr Met Pro Gly Cys Ser Gly Tyr Pro Asn Met Asp
                435                 440                 445

Leu Asp Cys Leu Leu Pro Gln Glu Trp Val Gln Tyr Phe Tyr Gln Glu
                450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
                500                 505                 510

Gly Tyr Phe Arg Phe Asp Ser Trp Val Asn Gln Phe Tyr Thr Leu Ala
                515                 520                 525

Pro Met Gly Asn Gly Thr Gly Arg Arg Arg Ala Val
                530                 535                 540

<210> SEQ ID NO 5
<211> LENGTH: 1725
<212> TYPE: DNA
<213> ORGANISM: Artificial Sequence
<220> FEATURE:
<223> OTHER INFORMATION: synthetic nucleotide sequence - Codon optimized
      sequence for the RSV A2 Fusion glycoprotein F0

<400> SEQUENCE: 5
atggagctgc ccatccttaa ggcaaatgcc attacgacaa tcctgcggc cgtcaccttc      60 tgctttgcca gctcacagaa tatcactgag gagttttacc agtctacatg ttcagcggtc     120
tccaaagggt acttgagtgc gctccgaacc ggatggtaca caagcgtcat caccatagaa     180
ctgtccaata taaggagaa taatgcaat gggaccgatg caaagttaa actcatcaaa        240 caggaactcg acaagtacaa gaatgccgtg acggagctcc agctgctgat gcagtctaca     300
cctgcagcta caacagggc aaggcgcgaa ctcccaagat tcatgaatta cactgaac        360 aacacgaaga gaccaatgt tacactgagc aagaaacgaa agcgccgctt ctcggattt       420 cttcttggcg tagggtccgc catcgcatca ggtatcgcag tgagcaaagt tctccatctc     480
gagggcgagt aaacaagat aaaatccgca ttgctcagca ccaacaaggc tgtggtgtcc      540
ttgagcaatg gcgtatcagt gctgaccagc aaggttctgg atctcaagaa ctatattgac     600
aaacagctgc tgcctattgt gaacaagcag tcttgtagaa ttagcaacat cgagaccgtc     660
attgagttcc agcagaaaaa taatagattg ctggagatca cgcgggagtt cagcgttaat    720
```

```
gctggagtca caaccCctgt tagcacgtat atgctgacca acagcgagtt gcttagcttg    780
atcaatgata tgccgataac gaatgatcag aagaaattga tgtccaacaa tgtccagatc    840
gtgcgacagc agagctactc catcatgtca attatcaagg aggaagtgct cgcatacgtg    900
gtccagctcc cattgtacgg cgtgatcgac actccatgct ggaagctgca cacatcacct    960
ctgtgcacca ctaacactaa agaaggttca aatatctgtc tcacaaggac cgaccgaggg   1020
tggtattgcg ataacgctgg atctgtgagt ttttcctc aggctgagac atgcaaagtg     1080
caaagcaacc gagtattctg tgacacaatg aactcactta ccctcccatc cgaggtgaat   1140
ctctgtaacg tggacatatt taaccctaag tacgattgta agatcatgac ctctaaaaca   1200
gatgtcagta gttctgtgat taccagtttg ggtgcaatag tcagctgcta tgggaaaact   1260
aaatgtacag cttctaataa gaaccgaggg atcatcaaga ccttctctaa tggatgtgac   1320
tatgttagca acaaggggt tgcacagtg tccgtaggca acactctgta ttatgtaaac    1380
aagcaggaag gaaaaagtct ctacgtcaag ggagaaccga tcattaattt ctacgatccg   1440
ttggtcttcc cctccgatga attcgacgcg agtatatccc aggtcaatga aaaattaat    1500
cagagccttg ctttatcag gaagagtgat gagcttctcc accatgtcaa tgctggcaaa   1560
tccacaacaa acatcatgat cactaccatc atcatcgtga tcattgtgat tctcttgagc   1620
ctcatcgctg ttggactgct tctgtactgt aaggcacgct ctactcctgt tactctctcc   1680
aaagatcagc tctccggtat caataatatc gcatttagca attga                  1725
```

<210> SEQ ID NO 6
<211> LENGTH: 566
<212> TYPE: PRT
<213> ORGANISM: respiratory syncytial virus
<220> FEATURE:
<221> NAME/KEY: MISC_FEATURE
<222> LOCATION: (1)..(566)
<223> OTHER INFORMATION: RSV A2 Fusion glycoprotein F0

<400> SEQUENCE: 6

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

```
Ala Val Val Ser Leu Ser Asn Gly Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
        500                 505                 510

Leu His His Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
        530                 535                 540

Gly Leu Leu Leu Tyr Cys Lys Ala Arg Ser Thr Pro Val Thr Leu Ser
545                 550                 555                 560

Lys Asp Gln Leu Ser Gly
                565

<210> SEQ ID NO 7
<211> LENGTH: 30098
<212> TYPE: DNA
```

<213> ORGANISM: Artificial Sequence
<220> FEATURE:
<223> OTHER INFORMATION: synthetic nucleotide sequence - Adenoviral vector backbone
<220> FEATURE:
<221> NAME/KEY: misc_feature
<222> LOCATION: (30089)..(30093)
<223> OTHER INFORMATION: n is a, c, g or t

<400> SEQUENCE: 7

```
taaggatccc atcatcaata atatacctta ttttggattg aagccaatat gataatgagg      60
gggtggagtt tgtgacgtgg cgcggggcgt gggaacgggg cgggtgacgt agtagtgtgg     120
cggaagtgtg atgttgcaag tgtggcggaa cacatgtaag cgacggatgt ggcaaaagtg     180
acgttttttgg tgtgcgccgg tgtacacagg aagtgacaat tttcgcgcgg ttttaggcgg     240
atgttgtagt aaatttgggc gtaaccgagt aagatttggc cattttcgcg ggaaaactga     300
ataagaggaa gtgaaatctg aataattttg tgttactcat agcgcgtaat gtgggaaaga     360
atatataagg tgggggtctt atgtagtttt gtatctgttt tgcagcagcc gccgccgcca     420
tgagcaccaa ctcgtttgat ggaagcattg tgagctcata tttgacaacg cgcatgcccc     480
catgggccgg ggtgcgtcag aatgtgatgg gctccagcat tgatggtcgc cccgtcctgc     540
ccgcaaactc tactaccttg acctacgaga ccgtgtctgg aacgccgttg gagactgcag     600
cctccgccgc cgcttcagcc gctgcagcca ccgcccgcgg gattgtgact gactttgctt     660
tcctgagccc gcttgcaagc agtgcagctt cccgttcatc cgcccgcgat gacaagttga     720
cggctctttt ggcacaattg gattctttga cccgggaact taatgtcgtt tctcagcagc     780
tgttggatct gcgccagcag gtttctgccc tgaaggcttc ctcccctccc aatgcggttt     840
aaaacataaa taaaaaacca gactctgttt ggatttggat caagcaagtg tcttgctgtc     900
tttatttagg ggttttgcgc gcgcggtagg cccgggacca gcggtctcgg tcgttgaggg     960
tcctgtgtat tttttccagg acgtggtaaa ggtgactctg gatgttcaga tacatgggca    1020
taagcccgtc tctggggtgg aggtagcacc actgcagagc ttcatgctgc ggggtggtgt    1080
tgtagatgat ccagtcgtag caggagcgct gggcgtggtg cctaaaaatg tctttcagta    1140
gcaagctgat tgccaggggc aggcccttgg tgtaagtgtt tacaaagcgg ttaagctggg    1200
atgggtgcat acgtggggat atgagatgca tcttggactg tattttagg ttggctatgt    1260
tcccagccat atccctccgg ggattcatgt tgtgcagaac caccagcaca gtgtatccgg    1320
tgcacttggg aaatttgtca tgtagcttag aaggaaatgc gtggaagaac ttggagacgc    1380
ccttgtgacc tccaagattt tccatgcatt cgtccataat gatggcaatg gcccacggg    1440
cggcggcctg ggcgaagata tttctgggat cactaacgtc atagttgtgt tccaggatga    1500
gatcgtcata ggccattttt acaaagcgcg gcggagggt gccagactgc ggtataatgg    1560
ttccatccgg cccaggggcg tagttaccct cacagatttg catttcccac gctttgagtt    1620
cagatggggg gatcatgtct acctgcgggg cgatgaagaa acggttttcc ggggtagggg    1680
agatcagctg gaagaaagc aggttcctga gcagctgcga cttaccgcag ccggtgggcc    1740
cgtaaatcac acctattacc gggtgcaact ggtagttaag agagctgcag ctgccgtcat    1800
ccctgagcag gggggccact tcgttaagca tgtccctgac tcgcatgttt tccctgacca    1860
aatccgccag aaggcgctcg ccgcccagcg atagcagttc ttgcaaggaa gcaaagttt    1920
tcaacggttt gagaccgtcc gccgtaggca tgctttgag cgtttgacca agcagttcca    1980
ggcggtccca cagctcggtc acctgctcta cggcatctcg atccagcata tctcctcgtt    2040
```

```
tcgcgggttg gggcggcttt cgctgtacgg cagtagtcgg tgctcgtcca gacgggccag    2100
ggtcatgtct ttccacgggc gcagggtcct cgtcagcgta gtctgggtca cggtgaaggg    2160
gtgcgctccg ggctgcgcgc tggccagggt gcgcttgagg ctggtcctgc tggtgctgaa    2220
gcgctgccgt tcttcgccct gcgcgtcggc caggtagcat ttgaccatgg tgtcatagtc    2280
cagcccctcc gcggcgtggc ccttggcgcg cagcttgccc ttggaggagg cgccgcacga    2340
ggggcagtgc agacttttga gggcgtagag cttgggcgcg agaaataccg attccgggga    2400
gtaggcatcc gcgccgcagg ccccgcagac ggtctcgcat tccacgagcc aggtgagctc    2460
tggccgttcg gggtcaaaaa ccaggtttcc cccatgcttt ttgatgcgtt tcttacctct    2520
ggtttccatg agccggtgtc cacgctcggt gacgaaaagg ctgtccgtgt ccccgtatac    2580
agacttgaga ggcctgtcct cgagcggtgt tccgcggtcc tcctcgtata gaaactcgga    2640
ccactctgag acaaaggctc gcgtccaggc cagcacgaag gaggctaagt gggaggggta    2700
gcggtcgttg tccactaggg ggtccactcg ctccagggtg tgaagacaca tgtcgccctc    2760
ttcggcatca aggaaggtga ttggtttgta ggtgtaggcc acgtgaccgg tgttcctga    2820 aggggggcta taaagggggg tggggcgcg ttcgtcctca ctctcttccg catcgctgtc    2880
tgcgagggcc agctgttggg gtgagtactc cctctgaaaa gcgggcatga cttctgcgct    2940
aagattgtca gtttccaaaa acgaggagga tttgatattc acctggcccg cggtgatgcc    3000
tttgagggtg gccgcatcca tctggtcaga aaagacaatc ttttttgttgt caagcttggt    3060 ggcaaacgac ccgtagaggg cgttggacag caacttggcg atggagcgca gggtttggtt    3120
tttgtcgcga tcgcgcgct ccttggccgc gatgtttagc tgcacgtatt cgcgcgcaac    3180
gcaccgccat tcgggaaaga cggtggtgcg ctcgtcgggc accaggtgca cgcgccaacc    3240
gcggttgtgc agggtgacaa ggtcaacgct ggtggctacc tctccgcgta ggcgctcgtt    3300
ggtccagcag aggcggccgc ccttgcgcga gcagaatggc ggtaggggt ctagctgcgt    3360 ctcgtccggg gggtctgcgt ccacggtaaa gaccccgggc agcaggcgcg cgtcgaagta    3420
gtctatcttg catccttgca agtctagcgc ctgctgccat gcgcgggcgg caagcgcgcg    3480
ctcgtatggg ttgagtgggg gaccccatgg catggggtgg gtgagcgcgg aggcgtacat    3540
gccgcaaatg tcgtaaacgt agaggggctc tctgagtatt ccaagatatg tagggtagca    3600
tcttccaccg cggatgctgg cgcgcacgta atcgtatagt tcgtgcgagg gagcgaggag    3660
gtcgggaccg aggttgctac gggcgggctg ctctgctcgg aagactatct gcctgaagat    3720
ggcatgtgag ttgatgata tggttggacg ctggaagacg ttgaagctgg cgtctgtgag    3780
acctaccgcg tcacgcacga aggaggcgta ggagtcgcgc agcttgttga ccagctcggc    3840
ggtgacctgc acgtctaggg cgcagtagtc cagggtttcc ttgatgatgt catacttatc    3900
ctgtcccttt ttttccaca gctcgcggtt gaggacaaac tcttcgcggt ctttccagta    3960
ctcttggatc ggaaacccgt cggcctccga acggtaagag cctagcatgt agaactggtt    4020 gacgcctgg taggcgcagc atccctttc tacgggtagc gcgtatgcct gcgcggcctt    4080
ccggagcgag gtgtgggtga gcgcaaaggt gtccctgacc atgactttga ggtactggta    4140
tttgaagtca gtgtcgtcgc atccgccctg ctcccagagc aaaaagtccg tgcgcttttt    4200
ggaacgcgga tttggcaggg cgaaggtgac atcgttgaag agtatctttc ccgcgcgagg    4260
cataaagttg cgtgtgatgc ggaagggtcc cggcacctcg gaacggttgt taattacctg    4320
ggcggcgagc acgatctcgt caaagccgtt gatgttgtgg cccacaatgt aaagttccaa    4380
gaagcgcggg atgcccttga tggaaggcaa ttttttaagt tcctcgtagg tgagctcttc    4440
```

```
aggggagctg agcccgtgct ctgaaagggc ccagtctgca agatgagggt tggaagcgac    4500
gaatgagctc cacaggtcac gggccattag catttgcagg tggtcgcgaa aggtcctaaa    4560
ctggcgacct atggccattt tttctggggt gatgcagtag aaggtaagcg ggtcttgttc    4620
ccagcggtcc catccaaggt tcgcggctag gtctcgcgcg gcagtcacta gaggctcatc    4680
tccgccgaac ttcatgacca gcatgaaggg cacgagctgc ttcccaaagg cccccatcca    4740
agtataggtc tctacatcgt aggtgacaaa gagacgctcg gtgcgaggat gcgagccgat    4800
cgggaagaac tggatctccc gccaccaatt ggaggagtgg ctattgatgt ggtgaaagta    4860
gaagtccctg cgacgggccg aacactcgtg ctggcttttg taaaaacgtg cgcagtactg    4920
gcagcggtgc acgggctgta catcctgcac gaggttgacc tgacgaccgc gcacaaggaa    4980
gcagagtggg aatttgagcc cctcgcctgg cgggtttggc tggtggtctt ctacttcggc    5040
tgcttgtcct tgaccgtctg gctgctcgag gggagttacg gtggatcgga ccaccacgcc    5100
gcgcgagccc aaagtccaga tgtccgcgcg cggcggtcgg agcttgatga caacatcgcg    5160
cagatgggag ctgtccatgg tctggagctc ccgcggcgtc aggtcaggcg ggagctcctg    5220
caggtttacc tcgcatagac gggtcagggc gcgggctaga tccaggtgat acctaatttc    5280
caggggctgg ttggtggcgg cgtcgatggc ttgcaagagg ccgcatcccc gcggcgcgac    5340
tacggtaccg cgcggcgggc ggtgggccgc ggggtgtcc ttggatgatg catctaaaag    5400
cggtgacgcg ggcgagcccc cggaggtagg gggggctccg gacccgccgg gagaggggc    5460 aggggcacgt cggcgccgcg cgcgggcagg agctggtgct gcgcgcgtag gttgctggcg    5520
aacgcgacga cgcggcggtt gatctcctga atctggcgcc tctgcgtgaa gacgacgggc    5580
ccggtgagct tgagcctgaa agagagttcg acagaatcaa tttcggtgtc gttgacggcg    5640
gcctggcgca aaatctcctg cacgtctcct gagttgtctt gataggcgat ctcggccatg    5700
aactgctcga tctcttcctc ctggagatct ccgcgtccgg ctcgctccac ggtggcggcg    5760
aggtcgttgg aaatgcgggc catgagctgc gagaaggcgt tgaggcctcc ctcgttccag    5820
acgcggctgt agaccacgcc cccttcggca tcgcgggcgc gcatgaccac ctgcgcgaga    5880
ttgagctcca cgtgccgggc gaagacggcg tagtttcgca ggcgctgaaa gaggtagttg    5940
agggtggtgg cggtgtgttc tgccacgaag aagtacataa cccagcgtcg caacgtggat    6000
tcgttgatat ccccccaaggc ctcaaggcgc tccatggcct cgtagaagtc cacggcgaag    6060
ttgaaaaact gggagttgcg cgccgacacg gttaactcct cctccagaag acggatgagc    6120
tcggcgacag tgtcgcgcac ctcgcgctca aggctacag gggcctcttc ttcttcttca    6180
atctcctctt ccataagggc ctccccttct tcttcttctg gcggcggtgg gggagggggg    6240
acacggcggc gacgacggcg caccgggagg cggtcgacaa agcgctcgat catctccccg    6300
cggcgacggc gcatggtctc ggtgacggcg cggccgttct cgcggggcg cagttggaag    6360 acgccgcccg tcatgtcccg gttatgggtt ggcgggggc tgccatgcgg cagggatacg    6420
gcgctaacga tgcatctcaa caattgttgt gtaggtactc cgccgccgag ggacctgagc    6480
gagtccgcat cgaccggatc ggaaaacctc tcgagaaagg cgtctaacca gtcacagtcg    6540
caaggtaggc tgagcaccgt ggcgggcggc agcgggcggc ggtcgggtt gtttctggcg    6600 gaggtgctgc tgatgatgta attaaagtag gcggtcttga acggcggat ggtcgacaga    6660 agcaccatgt ccttgggtcc ggcctgctga atgcgcaggc ggtcggccat gcccaggct    6720 tcgttttgac atcggcgcag gtctttgtag tagtcttgca tgagcctttc taccggcact    6780
```

```
tcttcttctc cttcctcttg tcctgcatct cttgcatcta tcgctgcggc ggcggcggag    6840
tttggccgta ggtggcgccc tcttcctccc atgcgtgtga ccccgaagcc cctcatcggc    6900
tgaagcaggg ctaggtcggc gacaacgcgc tcggctaata tggcctgctg cacctgcgtg    6960
agggtagact ggaagtcatc catgtccaca aagcggtggt atgcgcccgt gttgatggtg    7020
taagtgcagt tggccataac ggaccagtta acggtctggt gacccggctg cgagagctcg    7080
gtgtacctga gacgcgagta agccctcgag tcaaatacgt agtcgttgca agtccgcacc    7140
aggtactggt atcccaccaa aaagtgcggc ggcggctggc ggtagagggg ccagcgtagg    7200
gtggccgggg ctccggggc gagatcttcc aacataaggc gatgatatcc gtagatgtac     7260
ctggacatcc aggtgatgcc ggcggcggtg gtggaggcgc gcggaaagtc gcggacgcgg    7320
ttccagatgt tgcgcagcgg caaaaagtgc tccatggtcg ggacgctctg gccggtcagg    7380
cgcgcgcaat cgttgacgct ctaccgtgca aaggagagc ctgtaagcgg gcactcttcc     7440
gtggtctggt ggataaattc gcaagggtat catggcggac gaccggggtt cgagcccgt     7500 atccggccgt ccgccgtgat ccatgcggtt accgcccgcg tgtcgaaccc aggtgtgcga    7560
cgtcagacaa cggggagtg ctccttttgg cttccttcca ggcgcggcgg ctgctgcgct     7620
agcttttttg gccactggcc gcgcgcagcg taagcggtta ggctggaaag cgaaagcatt    7680
aagtggctcg ctccctgtag ccggagggtt attttccaag ggttgagtcg cgggaccccc    7740
ggttcgagtc tcggaccggc cggactgcgg cgaacggggg tttgcctccc cgtcatgcaa    7800
gaccccgctt gcaaattcct ccggaaacag ggacgagccc cttttttgct tttcccagat    7860
gcatccggtg ctgcggcaga tgcgcccccc tcctcagcag cggcaagagc aagagcagcg    7920
gcagacatgc agggcaccct cccctcctcc taccgcgtca ggaggggcga catccgcggt    7980
tgacgcggca gcagatggtg attacgaacc cccgcggcgc cgggcccggc actacctgga    8040
cttggaggag ggcgagggcc tggcgcggct aggagcgccc tctcctgagc ggtacccaag    8100
ggtgcagctg aagcgtgata cgcgtgaggc gtacgtgccg cggcagaacc tgtttcgcga    8160
ccgcgaggga gaggagcccg aggagatgcg ggatcgaaag ttccacgcag ggcgcgagct    8220
gcggcatggc ctgaatcgcg agcggttgct cgcgaggag gactttgagc ccgacgcgcg     8280
aaccgggatt agtcccgcgc gcgcacacgt ggcggccgcc gacctggtaa ccgcatacga    8340
gcagacggtg aaccaggaga ttaactttca aaaagctttt aacaaccacg tgcgtacgct    8400
tgtggcgcgc gaggaggtgg ctataggact gatgcatctg tgggactttg taagcgcgct    8460
ggagcaaaac ccaaatagca agccgctcat ggcgcagctg ttccttatag tgcagcacag    8520
cagggacaac gaggcattca gggatgcgct gctaaacata gtagagcccg agggccgctg    8580
gctgctcgat ttgataaaca tcctgcagag catagtggtg caggagcgca gcttgagcct    8640
ggctgacaag gtggccgcca tcaactattc catgcttagc ctgggcaagt tttacgcccg    8700
caagatatac catccccctt acgttccat agacaaggag gtaaagatcg aggggttcta     8760
catgcgcatg gcgctgaagg tgcttacctt gagcgacgac ctgggcgttt atcgcaacga    8820
gcgcatccac aaggccgtga gcgtgagccg gcggcgcgag ctcagcgacc gcgagctgat    8880
gcacagcctg caaagggccc tggctggcac gggcagcggc gatagagagg ccgagtccta    8940 cttttgacgcg ggcgctgacc tgcgctgggc cccaagccga cgcgccctgg aggcagctgg   9000
ggccggacct gggctggcgg tggcaccgc gcgcgctggc aacgtcggcg cgtggagga     9060 atatgacgag gacgatgagt acgagccaga ggacggcgag tactaagcgg tgatgtttct    9120
gatcagatga tgcaagacgc aacggacccg gcggtgcggg cggcgctgca gagccagccg    9180
```

```
tccggcctta actccacgga cgactggcgc caggtcatgg accgcatcat gtcgctgact    9240
gcgcgcaatc ctgacgcgtt ccggcagcag ccgcaggcca accggctctc cgcaattctg    9300
gaagcggtgg tcccggcgcg cgcaaacccc acgcacgaga aggtgctggc gatcgtaaac    9360
gcgctggccg aaaacagggc catccggccc gacgaggccg gcctggtcta cgacgcgctg    9420
cttcagcgcg tggctcgtta acagcggc aacgtgcaga ccaacctgga ccggctggtg    9480
ggggatgtgc gcgaggccgt ggcgcagcgt gagcgcgcgc agcagcaggg caacctgggc    9540
tccatggttg cactaaacgc cttcctgagt acacagcccg ccaacgtgcc gcggggacag    9600
gaggactaca ccaactttgt gagcgcactg cggctaatgg tgactgagac accgcaaagt    9660
gaggtgtacc agtctgggcc agactatttt ttccagacca gtagacaagg cctgcagacc    9720
gtaaacctga gccaggcttt caaaaacttg caggggctgt gggggtgcg ggctcccaca    9780 ggcgaccgcg cgaccgtgtc tagcttgctg acgcccaact cgcgcctgtt gctgctgcta    9840
atagcgccct tcacggacag tggcagcgtg tcccgggaca catacctagg tcacttgctg    9900
acactgtacc gcgaggccat aggtcaggcg catgtggacg agcatacttt ccaggagatt    9960
acaagtgtca gccgcgcgct ggggcaggag gacacgggca gcctggaggc aaccctaaac   10020
tacctgctga ccaaccggcg gcagaagatc ccctcgttgc acagtttaaa cagcgaggag   10080
gagcgcattt tgcgctacgt gcagcagagc gtgagcctta acctgatgcg cgacggggta   10140
acgcccagcg tggcgctgga catgaccgcg cgcaacatgg aaccgggcat gtatgcctca   10200
aaccggccgt ttatcaaccg cctaatggac tacttgcatc gcgcggccgc cgtgaacccc   10260
gagtatttca ccaatgccat cttgaacccg cactggctac cgccccctgg tttctacacc   10320
gggggattcg aggtgcccga gggtaacgat ggattcctct gggacgacat agacgacagc   10380
gtgttttccc cgcaaccgca gaccctgcta gagttgcaac agcgcgagca ggcagaggcg   10440
gcgctgcgaa aggaaagctt ccgcaggcca agcagcttgt ccgatctagg cgctgcggcc   10500
ccgcggtcag atgctagtag cccatttcca agcttgatag ggtctcttac cagcactcgc   10560
accacccgcc cgcgcctgct gggcgaggag gagtacctaa caactcgct gctgcagccg   10620 cagcgcgaaa aaaacctgcc tccggcattt cccaacaacg ggatagagag cctagtggac   10680
aagatgagta gatggaagac gtacgcgcag gagcacaggg acgtgccagg cccgcgcccg   10740
cccacccgtc gtcaaaggca cgaccgtcag cggggtctgg tgtgggagga cgatgactcg   10800
gcagacgaca gcagcgtcct ggatttggga gggagtggca acccgtttgc gcaccttcgc   10860
cccaggctgg ggagaatgtt ttaaaaaaaa aaagcatga tgcaaaataa aaaactcacc   10920
aaggccatgg caccgagcgt tggttttctt gtattcccct tagtatgcgg cgcgcggcga   10980
tgtatgagga aggtcctcct ccctcctacg agagtgtggt gagcgcggcg ccagtggcgg   11040
cggcgctggg ttctcccttc gatgctcccc tggacccgcc gtttgtgcct ccgcggtacc   11100
tgcggcctac cgggggaga aacagcatcc gttactctga gttggcaccc ctattcgaca   11160
ccacccgtgt gtacctggtg acaacaagt caacggatgt ggcatccctg aactaccaga   11220
acgaccacag caactttctg accacggtca ttcaaaacaa tgactacagc ccgggggagg   11280
caagcacaca gaccatcaat cttgacgacc ggtcgcactg gggcggcgac ctgaaaacca   11340
tcctgcatac caacatgcca aatgtgaacg agttcatgtt taccaataag tttaaggcgc   11400
gggtgatggt gtcgcgcttg cctactaagg acaatcaggt ggagctgaaa tacgagtggg   11460
tggagttcac gctgcccgag ggcaactact ccgagaccat gaccatagac cttatgaaca   11520
```

```
acgcgatcgt ggagcactac ttgaaagtgg gcagacagaa cggggttctg gaaagcgaca    11580
tcggggtaaa gtttgacacc cgcaacttca gactggggtt tgaccccgtc actggtcttg    11640
tcatgcctgg ggtatataca aacgaagcct tccatccaga catcattttg ctgccaggat    11700
gcggggtgga cttcacccac agccgcctga gcaacttgtt gggcatccgc aagcggcaac    11760
ccttccagga gggctttagg atcacctacg atgatctgga gggtggtaac attcccgcac    11820
tgttggatgt ggacgcctac caggcgagct gaaagatga caccgaacag ggcggggtg    11880 gcgcaggcgg cagcaacagc agtggcagcg gcgcggaaga gaactccaac gcggcagccg    11940
cggcaatgca gccggtggag gacatgaacg atcatgccat tcgcggcgac acctttgcca    12000
cacgggctga ggagaagcgc gctgaggccg aagcagcggc cgaagctgcc gccccgctg    12060 cgcaacccga ggtcgagaag cctcagaaga aaccggtgat caaaccctg acagaggaca    12120 gcaagaaacg cagttacaac ctaataagca atgacagcac cttcacccag taccgcagct    12180
ggtaccttgc atacaactac ggcgaccctc agaccggaat ccgctcatgg accctgcttt    12240
gcactcctga cgtaacctgc ggctcggagc aggtctactg gtcgttgcca gacatgatgc    12300
aagaccccgt gaccttccgc tccacgcgcc agatcagcaa cttccggtg gtgggcgccg    12360 agctgttgcc cgtgcactcc aagagcttct acaacgacca ggccgtctac tcccaactca    12420
tccgccagtt tacctctctg acccacgtgt tcaatcgctt tcccgagaac cagattttgg    12480
cgcgcccgcc agcccccacc atcaccaccg tcagtgaaaa cgttcctgct ctcacagatc    12540
acgggacgct accgctgcgc aacagcatcg gaggagtcca gcgagtgacc attactgacg    12600
ccagacgccg cacctgcccc tacgtttaca aggccctggg catagtctcg ccgcgcgtcc    12660
tatcgagccg cacttttga gcaagcatgt ccatccttat atcgcccagc aataacacag    12720 gctgggcct cgcttccca agcaagatgt ttggcgggc caagaagcgc tccgaccaac    12780
acccagtgcg cgtgcgcggg cactaccgcg cgccctgggg cgcgcacaaa gcggccgca    12840 ctgggcgcac caccgtcgat gacgccatcg acgcggtggt ggaggaggcg cgcaactaca    12900
cgcccacgcc gccaccagtg tccacagtgg acgcggccat tcagaccgtg gtgcgcggag    12960
cccggcgcta tgctaaaatg aagagacggc ggaggcgcgt agcacgtcgc caccgccgcc    13020
gacccggcac tgccgcccaa cgcgcggcgg cggccctgct taaccgcgca cgtcgcaccg    13080
gccgacgggc ggccatgcgg gccgctcgaa ggctggccgc gggtattgtc actgtgcccc    13140
ccaggtccag gcgacgagcg gccgccgcag cagccgcggc cattagtgct atgactcagg    13200
gtcgcagggg caacgtgtat tgggtgcgcg actcggttag cggcctgcgc gtgcccgtgc    13260
gcacccgccc cccgcgcaac tagattgcaa gaaaaaacta cttagactcg tactgttgta    13320
tgtatccagc ggcggcggcg cgcaacgaag ctatgtccaa gcgcaaaatc aaagaagaga    13380
tgctccaggt catcgcgccg gagatctatg ccccccgaa gaaggaagag caggattaca    13440
agccccgaaa gctaaagcgg gtcaaaaaga aaagaaaga tgatgatgat gaacttgacg    13500
acgaggtgga actgctgcac gctaccgcgc ccaggcgacg ggtacagtgg aaaggtcgac    13560
gcgtaaaacg tgttttgcga cccggcacca ccgtagtctt tacgcccggt gagcgctcca    13620
cccgcaccta caagcgcgtg tatgatgagg tgtacggcga cgaggacctg cttgagcagg    13680
ccaacgagcg cctcggggag tttgcctacg gaaagcggca taaggacatg ctggcgttgc    13740
cgctggacga gggcaaccca acacctagcc taaagcccgt aacactgcag caggtgctgc    13800
ccgcgcttgc accgtccgaa gaaaagcgcg gcctaaagcg cgagtctggt gacttggcac    13860
ccaccgtgca gctgatggta cccaagcgcc agcgactgga agatgtcttg gaaaaaatga    13920
```

```
ccgtggaacc tgggctggag cccgaggtcc gcgtgcggcc aatcaagcag gtggcgccgg   13980
gactgggcgt gcagaccgtg gacgttcaga tacccactac cagtagcacc agtattgcca   14040
ccgccacaga gggcatggag acacaaacgt ccccggttgc ctcagcggtg gcggatgccg   14100
cggtgcaggc ggtcgctgcg gccgcgtcca agacctctac ggaggtgcaa acggaccgt    14160 ggatgtttcg cgtttcagcc ccccggcgcc cgcgcggttc gaggaagtac ggcgccgcca   14220
gcgcgctact gcccgaatat gccctacatc cttccattgc gcctacccccc ggctatcgtg  14280 gctacaccta ccgccccaga agacgagcaa ctacccgacg ccgaaccacc actggaaccc   14340
gccgccgccg tcgccgtcgc cagcccgtgc tggccccgat ttccgtgcgc agggtggctc   14400
gcgaaggagg caggaccctg gtgctgccaa cagcgcgcta ccaccccagc atcgtttaaa   14460
agccggtctt tgtggttctt gcagatatgg ccctcacctg ccgcctccgt ttccggtgc    14520 cgggattccg aggaagaatg caccgtagga ggggcatggc cggccacggc ctgacgggcg   14580
gcatgcgtcg tgcgcaccac cggcggcggc gcgcgtcgca ccgtcgcatg cgcggcggta   14640
tcctgcccct ccttattcca ctgatcgccg cggcgattgg cgccgtgccc ggaattgcat   14700
ccgtggcctt gcaggcgcag agacactgat taaaaacaag ttgcatgtgg aaaaatcaaa   14760
ataaaaagtc tggactctca cgctcgcttg gtcctgtaac tattttgtag aatggaagac   14820
atcaactttg cgtctctggc cccgcgacac ggctcgcgcc cgttcatggg aaactggcaa   14880
gatatcggca ccagcaatat gagcggtggc gccttcagct ggggctcgct gtggagcggc   14940
attaaaaatt tcggttccac cgttaagaac tatggcagca aggcctggaa cagcagcaca   15000
ggccagatgc tgagggataa gttgaaagag caaaatttcc aacaaaaggt ggtagatggc   15060
ctggcctctg gcattagcgg ggtggtggac ctggccaacc aggcagtgca aaataagatt   15120
aacagtaagc ttgatccccg ccctcccgta gaggagcctc caccggccgt ggagacagtg   15180
tctccagagg ggcgtggcga aaagcgtccg cgccccgaca gggaagaaac tctggtgacg   15240
caaatagacg agcctccctc gtacgaggag gcactaaagc aaggcctgcc caccacccgt   15300
cccatcgcgc ccatggctac cggagtgctg ggccagcaca cacccgtaac gctggacctg   15360
cctccccccg ccgacaccca gcagaaacct gtgctgccag gccgaccgc cgttgttgta    15420 acccgtccta gccgcgcgtc cctgcgccgc gccgccagcg gtccgcgatc gttgcggccc   15480
gtagccagtg gcaactggca aagcacactg aacagcatcg tgggtctggg ggtgcaatcc   15540
ctgaagcgcc gacgatgctt ctgaatagct aacgtgtcgt atgtgtgtca tgtatgcgtc   15600
catgtcgccg ccagaggagc tgctgagccg ccgcgcgccc gctttccaag atggctaccc   15660
cttcgatgat gccgcagtgg tcttacatgc acatctcggg ccaggacgcc tcggagtacc   15720
tgagccccgg gctggtgcag tttgcccgcg ccaccgagac gtacttcagc ctgaataaca   15780
agtttagaaa ccccacggtg gcgcctacgc acgacgtgac cacagaccgg tcccagcgtt   15840
tgacgctgcg gttcatccct gtggaccgtg aggatactgc gtactcgtac aaggcgcggt   15900
tcaccctagc tgtgggtgat aaccgtgtgc tggacatggc ttccacgtac tttgacatcc   15960
gcggcgtgct ggacagggc cctactttta agccctactc tggcactgcc tacaacgccc    16020
tggctcccaa gggtgcccca aatccttgcg aatgggatga agctgctact gctcttgaaa   16080
taaacctaga agaagaggac gatgacaacg aagacgaagt agacgagcaa gctgagcagc   16140
aaaaaactca cgtatttggg caggcgcctt attctggtat aaatattaca aaggagggta   16200
ttcaaatagg tgtcgaaggt caaacaccta aatatgccga taaaacattt caacctgaac   16260
```

```
ctcaaatagg agaatctcag tggtacgaaa ctgaaattaa tcatgcagct gggagagtcc   16320
ttaaaaagac tacccaatg aaaccatgtt acggttcata tgcaaaaccc acaaatgaaa    16380
atggagggca aggcattctt gtaaagcaac aaaatggaaa gctagaaagt caagtggaaa   16440
tgcaattttt ctcaactact gaggcgaccg caggcaatgg tgataacttg actcctaaag   16500
tggtattgta cagtgaagat gtagatatag aaaccccaga cactcatatt tcttacatgc   16560
ccactattaa ggaaggtaac tcacgagaac taatgggcca acaatctatg cccaacaggc   16620
ctaattacat tgcttttagg gacaattta ttggtctaat gtattacaac agcacgggta    16680
atatgggtgt tctggcgggc caagcatcgc agttgaatgc tgttgtagat ttgcaagaca   16740
gaaacacaga gctttcatac cagcttttgc ttgattccat tggtgataga accaggtact   16800
tttctatgtg gaatcaggct gttgacagct atgatccaga tgttagaatt attgaaaatc   16860
atggaactga agatgaactt ccaaattact gctttccact gggaggtgtg attaatacag   16920
agactcttac caaggtaaaa cctaaaacag gtcaggaaaa tggatgggaa aaagatgcta   16980
cagaattttc agataaaaat gaaataagag ttggaaataa ttttgccatg gaaatcaatc   17040
taaatgccaa cctgtggaga aatttcctgt actccaacat agcgctgtat ttgcccgaca   17100
agctaaagta cagtccttcc aacgtaaaaa tttctgataa cccaaacacc tacgactaca   17160
tgaacaagcg agtggtggct cccgggttag tggactgcta cattaaccct ggagcacgct   17220
ggtcccttga ctatatggac aacgtcaacc catttaacca ccaccgcaat gctggcctgc   17280
gctaccgctc aatgttgctg gcaatggtc gctatgtgcc cttccacatc caggtgcctc    17340
agaagttctt tgccattaaa aacctccttc tcctgccggg ctcatacacc tacgagtgga   17400
acttcaggaa ggatgttaac atggttctgc agagctccct aggaaatgac ctaagggttg   17460
acggagccag cattaagttt gatagcattt gcctttacgc caccttcttc cccatggccc   17520
acaacaccgc ctccacgctt gaggccatgc ttagaaacga caccaacgac cagtccttta   17580
acgactatct ctccgccgcc aacatgctct accctatacc cgccaacgct accaacgtgc   17640
ccatatccat cccctcccgc aactgggcgg ctttccgcgg ctgggccttc acgcgcctta   17700
agactaagga aaccccatca ctgggctcgg gctacgaccc ttattacacc tactctggct   17760
ctatacccta cctagatgga accttttacc tcaaccacac ctttaagaag gtggccatta   17820
cctttgactc ttctgtcagc tggcctggca atgaccgcct gcttaccccc aacgagtttg   17880
aaattaagcg ctcagttgac ggggagggtt acaacgttgc ccagtgtaac atgaccaaag   17940
actggttcct ggtacaaatg ctagctaact acaacattgg ctaccagggc ttctatatcc   18000
cagagagcta caaggaccgc atgtactcct tctttagaaa cttccagccc atgagccgtc   18060
aggtggtgga tgatactaaa tacaaggact accaacaggt gggcatccta caccaacaca   18120
acaactctgg atttgttggc taccttgccc ccaccatgcg cgaaggacag gcctaccctg   18180
ctaacttccc ctatccgctt ataggcaaga ccgcagttga cagcattacc cagaaaaagt   18240
ttctttgcga tcgcacccct tggcgcatcc cattctccag taactttatg tccatgggcg   18300
cactcacaga cctgggccaa aaccttctct acgccaactc cgcccacgcg ctagacatga   18360
cttttgaggt ggatcccatg gacgagccca cccttcttta tgttttgttt gaagtctttg   18420
acgtggtccg tgtgcaccgg ccgcaccgcg gcgtcatcga aaccgtgtac ctgcgcacgc   18480
ccttctcggc cggcaacgcc acaacataaa gaagcaagca acatcaacaa cagctgccgc   18540
catgggctcc agtgagcagg aactgaaagc cattgtcaaa gatcttggtt gtgggccata   18600
ttttttgggc acctatgaca agcgctttcc aggctttgtt tctccacaca agctcgcctg   18660
```

```
cgccatagtc aatacggccg gtcgcgagac tggggggcgta cactggatgg cctttgcctg   18720
gaacccgcac tcaaaaacat gctacctctt tgagcccttt ggcttttctg accagcgact   18780
caagcaggtt taccagtttg agtacgagtc actcctgcgc cgtagcgcca ttgcttcttc   18840
ccccgaccgc tgtataacgc tggaaaagtc cacccaaagc gtacaggggc ccaactcggc   18900
cgcctgtgga ctattctgct gcatgtttct ccacgccttt gccaactggc cccaaactcc   18960
catggatcac aaccccacca tgaacctttat taccgggggta cccaactcca tgctcaacag   19020
tccccaggta cagcccaccc tgcgtcgcaa ccaggaacag ctctacagct tcctggagcg   19080
ccactcgccc tacttccgca gccacagtgc gcagattagg agcgccactt cttttttgtca   19140 cttgaaaaac atgtaaaaat aatgtactag agacactttc aataaaggca aatgcttttta   19200 tttgtacact ctcgggtgat tatttacccc cacccttgcc gtctgcgccg tttaaaaatc   19260 aaagggggttc tgccgcgcat cgctatgcgc cactggcagg gacacgttgc gatactggtg   19320
tttagtgctc cacttaaact caggcacaac catccgcggc agctcggtga agttttcact   19380
ccacaggctg cgcaccatca ccaacgcgtt tagcaggtcg ggcgccgata tcttgaagtc   19440
gcagttgggg cctccgccct gcgcgcgcga gttgcgatac acagggttgc agcactggaa   19500
cactatcagc gccgggtggt gcacgctggc cagcacgctc ttgtcggaga tcagatccgc   19560
gtccaggtcc tccgcgttgc tcagggcgaa cggagtcaac tttggtagct gccttcccaa   19620
aaagggcgcg tgcccaggct ttgagttgca ctcgcaccgt agtggcatca aaggtgacc   19680 gtgcccggtc tgggcgttag gatacagcgc ctgcataaaa gccttgatct gcttaaaagc   19740
cacctgagcc tttgcgcctt cagagaagaa catgccgcaa gacttgccgg aaaactgatt   19800
ggccggacag gccgcgtcgt gcacgcagca ccttgcgtcg gtgttggaga tctgcaccac   19860
atttcggccc caccggttct tcacgatctt ggccttgcta gactgctcct tcagcgcgcg   19920
ctgcccgttt tcgctcgtca catccatttc aatcacgtgc tccttattta tcataatgct   19980
tccgtgtaga cacttaagct cgccttcgat ctcagcgcag cggtgcagcc acaacgcgca   20040
gcccgtgggc tcgtgatgct tgtaggtcac ctctgcaaac gactgcaggt acgcctgcag   20100
gaatcgcccc atcatcgtca caaaggtctt gttgctggtg aaggtcagct gcaacccgcg   20160
gtgctcctcg ttcagccagg tcttgcatac ggccgccaga gcttccactt ggtcaggcag   20220
tagtttgaag ttgcccttta gatcgttatc cacgtggtac ttgtccatca gcgcgcgcgc   20280
agcctccatg cccttctccc acgcagacac gatcggcaca ctcagcgggt tcatcaccgt   20340
aatttcactt tccgcttcgc tgggctcttc ctcttcctct tgcgtccgca taccacgcgc   20400
cactgggtcg tcttcattca gccgccgcac tgtgcgctta cctcctttgc catgcttgat   20460
tagcaccggt gggttgctga aacccaccat ttgtagcgcc acatcttctc tttcttcctc   20520
gctgtccacg attacctctg gtgatggcgg gcgctcgggc ttgggagaag ggcgcttctt   20580
tttcttcttg ggcgcaatgg ccaaatccgc cgccgaggtc gatggccgcg ggctgggtgt   20640
gcgcggcacc agcgcgtctt gtgatgagtc ttcctcgtcc tcggactcga tacgccgcct   20700
catccgcttt tttgggggcg cccgggggagg cggcggcgac ggggacgggg acgacacgtc   20760
ctccatggtt ggggggacgtc gcgccgcacc gcgtccgcgc tcggggtgg tttcgcgctg   20820 ctcctcttcc cgactggcca tttccttctc ctataggcag aaaaagatca tggagtcagt   20880
cgagaagaag gacagcctaa ccgcccctc tgagttcgcc accaccgcct ccaccgatgc   20940
cgccaacgcg cctaccacct tccccgtcga ggcaccccccg cttgaggagg aggaagtgat   21000
```

```
tatcgagcag gacccaggtt ttgtaagcga agacgacgag gaccgctcag taccaacaga    21060
ggataaaaag caagaccagg acaacgcaga ggcaaacgag gaacaagtcg ggcgggggga    21120
cgaaaggcat ggcgactacc tagatgtggg agacgacgtg ctgttgaagc atctgcagcg    21180
ccagtgcgcc attatctgcg acgcgttgca agagcgcagc gatgtgcccc tcgccatagc    21240
ggatgtcagc cttgcctacg aacgccacct attctcaccg cgcgtacccc ccaaacgcca    21300
agaaaacggc acatgcgagc ccaacccgcg cctcaacttc taccccgtat ttgccgtgcc    21360
agaggtgctt gccacctatc acatcttttt ccaaaactgc aagataccccc tatcctgccg    21420 tgccaaccgc agccgagcgg acaagcagct ggccttgcgg cagggcgctg tcatacctga    21480
tatcgcctcg ctcaacgaag tgccaaaaat ctttgagggt cttggacgcg acgagaagcg    21540
cgcggcaaac gctctgcaac aggaaaaacag cgaaaatgaa agtcactctg gagtgttggt    21600
ggaactcgag ggtgacaacg cgcgcctagc cgtactaaaa cgcagcatcg aggtcaccca    21660
ctttgcctac ccggcactta acctacccccc caaggtcatg agcacagtca tgagtgagct    21720
gatcgtgcgc cgtgcgcagc ccctggagag ggatgcaaat ttgcaagaac aaacagagga    21780
gggcctaccc gcagttggcg acgagcagct agcgcgctgg cttcaaacgc gcgagcctgc    21840
cgacttggag gagcgacgca aactaatgat ggccgcagtg ctcgttaccg tggagcttga    21900
gtgcatgcag cggttctttg ctgacccgga gatgcagcgc aagctagagg aaacattgca    21960
ctacaccttt cgacagggct acgtacgcca ggcctgcaag atctccaacg tggagctctg    22020
caacctggtc tcctaccttg gaattttgca cgaaaaccgc cttgggcaaa acgtgcttca    22080
ttccacgctc aagggcgagg cgcgccgcga ctacgtccgc gactgcgttt acttatttct    22140
atgctacacc tggcagacgg ccatgggcgt ttggcagcag tgcttggagg agtgcaacct    22200
caaggagctg cagaaactgc taaagcaaaa cttgaaggac ctatggacgg ccttcaacga    22260
gcgctccgtg gccgcgcacc tggcggacat cattttcccc gaacgcctgc ttaaaaccct    22320
gcaacagggt ctgccagact tcaccagtca aagcatgttg cagaacttta ggaacttat    22380 cctagagcgc tcaggaatct tgcccgccac ctgctgtgca cttcctagcg actttgtgcc    22440
cattaagtac cgcgaatgcc ctccgccgct ttggggccac tgctaccttc tgcagctagc    22500
caactacctt gcctaccact ctgacataat ggaagacgtg agcggtgacg tctactgga    22560 gtgtcactgt cgctgcaacc tatgcacccc gcaccgctcc ctggtttgca attcgcagct    22620
gcttaacgaa agtcaaatta tcggtacctt tgagctgcag ggtccctcgc ctgacgaaaa    22680
gtccgcggct ccggggttga aactcactcc ggggctgtgg acgtcggctt accttcgcaa    22740
atttgtacct gaggactacc acgcccacga gattaggttc tacgaagacc aatcccgccc    22800
gccaaatgcg gagcttaccg cctgcgtcat tacccagggc cacattcttg gccaattgca    22860
agccatcaac aaagcccgcc aagagtttct gctacgaaag ggacgggggg tttacttgga    22920
cccccagtcc ggcgaggagc tcaacccaat ccccccgccg ccgcagccct atcagcagca    22980
gccgcgggcc cttgcttccc aggatggcac ccaaaaagaa gctgcagctg ccgccgccac    23040
ccacggacga ggaggaatac tgggacagtc aggcagagga ggttttggac gaggaggagg    23100
aggacatgat ggaagactgg gagagcctag acgaggaagc ttccgaggtc gaagaggtgt    23160
cagacgaaac accgtcaccc tcggtcgcat tcccctcgcc ggcgcccag aaatcggcaa    23220 ccggttccag catggctaca acctccgctc ctcaggcgcc gccggcactg cccgttcgcc    23280
gacccaaccg tagatgggac accactggaa ccagggccgg taagtccaag cagccgccgc    23340
cgttagccca agagcaacaa cagcgccaag gctaccgctc atggcgcggg cacaagaacg    23400
```

```
ccatagttgc ttgcttgcaa gactgtgggg gcaacatctc cttcgcccgc cgctttcttc    23460
tctaccatca cggcgtggcc ttcccccgta acatcctgca ttactaccgt catctctaca    23520
gcccatactg caccggcggc agcggcagcg gcagcaacag cagcggccac acagaagcaa    23580
aggcgaccgg atagcaagac tctgacaaag cccaagaaat ccacagcggc ggcagcagca    23640
ggaggaggag cgctgcgtct ggcgcccaac gaacccgtat cgaccgcga gcttagaaac     23700 aggatttttc ccactctgta tgctatattt caacagagca ggggccaaga acaagagctg    23760
aaaataaaaa acaggtctct gcgatccctc acccgcagct gcctgtatca caaaagcgaa    23820
gatcagcttc ggcgcacgct ggaagacgcg gaggctctct tcagtaaata ctgcgcgctg    23880
actcttaagg actagtttcg cgccctttct caaatttaag cgcgaaaact acgtcatctc    23940
cagcggccac acccggcgcc agcacctgtc gtcagcgcca ttatgagcaa ggaaattccc    24000
acgccctaca tgtggagtta ccagccacaa atgggacttg cggctggagc tgcccaagac    24060
tactcaaccc gaataaacta catgagcgcg ggaccccaca tgatatcccg ggtcaacgga    24120
atccgcgccc accgaaaccg aattctcttg gaacaggcgg ctattaccac cacacctcgt    24180
aataaccttA atccccgtag ttggcccgct gccctggtgt accaggaaag tcccgctccc    24240
accactgtgg tacttcccag agacgcccag gccgaagttc agatgactaa ctcaggggcg    24300
cagcttgcgg gcggctttcg tcacagggtg cggtcgcccg ggcagggtat aactcacctg    24360
acaatcagag ggcgaggtat tcagctcaac gacgagtcgg tgagctcctc gcttggtctc    24420
cgtccggacg ggacatttca gatcggcggc gccggccgtc cttcattcac gcctcgtcag    24480
gcaatcctaa ctctgcagac ctcgtcctct gagccgcgct ctggaggcat tggaactctg    24540
caatttattg aggagtttgt gccatcggtc tactttaacc ccttctcggg acctcccggc    24600
cactatccgg atcaatttat tcctaacttt gacgcggtaa aggactcggc ggacggctac    24660
gactgaatgt taagtggaga ggcagagcaa ctgcgcctga acacctggt ccactgtcgc      24720 cgccacaagt gctttgcccg cgactccggt gagttttgct actttgaatt gcccgaggat    24780
catatcgagg gccggcgca cggcgtccgg cttaccgccc agggagagct tgcccgtagc     24840
ctgattcggg agtttaccca gcgcccctg ctagttgagc gggacagggg accctgtgtt    24900
ctcactgtga tttgcaactg tcctaacctt ggattacatc aagatcctct agttataact    24960
agagtacccg gggatcttat tccctttaac taataaaaaa aaataataaa gcatcactta    25020
cttaaaatca gttagcaaat ttctgtccag tttattcagc agcacctcct tgccctcctc    25080
ccagctctgt tattgcagct tcctcctggc tgcaaacttt ctccacaatc taaatggaat    25140
gtcagtttcc tcctgttcct gtccatccgc acccactatc ttcatgttgt tgcagatgaa    25200
gcgcgcaaga ccgtctgaag ataccttcaa ccccgtgtat ccatatgaca cggaaaccgg    25260
tcctccaact gtgccttttc ttactcctcc ctttgtatcc cccaatgggt ttcaagagag    25320 tcccctggg gtactctctt tgcgcctatc cgaacctcta gttacctcca atggcatgct      25380
tgcgctcaaa atgggcaacg gcctctctct ggacgaggcc ggcaaccta cctcccaaaa     25440 tgtaaccact gtgagcccac ctctcaaaaa aaccaagtca aacataaacc tggaaatatc    25500 tgcaccctc acagttacct cagaagccct aactgtggct gccgccgcac ctctaatggt    25560
cgcgggcaac acactcacca tgcaatcaca ggccccgcta accgtgcacg actccaaact    25620
tagcattgcc acccaaggac ccctcacagt gtcagaagga aagctagccc tgcaaacatc    25680
aggccccctc accaccaccg atagcagtac ccttactatc actgcctcac cccctctaac    25740
```

```
tactgccact ggtagcttgg gcattgactt gaaagagccc atttatacac aaaatggaaa   25800
actaggacta aagtacgggg ctcctttgca tgtaacagac gacctaaaca ctttgaccgt   25860
agcaactggt ccaggtgtga ctattaataa tacttccttg caaactaaag ttactggagc   25920
cttgggtttt gattcacaag gcaatatgca acttaatgta gcaggaggac taaggattga   25980
ttctcaaaac agacgcctta tacttgatgt tagttatccg tttgatgctc aaaaccaact   26040
aaatctaaga ctaggacagg gccctctttt tataaactca gcccacaact tggatattaa   26100
ctacaacaaa ggcctttact tgtttacagc ttcaaacaat tccaaaaagc ttgaggttaa   26160
cctaagcact gccaaggggt tgatgtttga cgctacagcc atagccatta atgcaggaga   26220
tgggcttgaa tttggttcac ctaatgcacc aaacacaaat cccctcaaaa caaaaattgg   26280
ccatggccta gaatttgatt caaacaaggc tatggttcct aaactaggaa ctggccttag   26340
ttttgacagc acaggtgcca ttacagtagg aaacaaaaat aatgataagc taactttgtg   26400
gaccacacca gctccatctc ctaactgtag actaaatgca gagaaagatg ctaaactcac   26460
tttggtctta acaaaatgtg gcagtcaaat acttgctaca gtttcagttt tggctgttaa   26520
aggcagtttg gctccaatat ctggaacagt tcaaagtgct catcttatta taagatttga   26580
cgaaaatgga gtgctactaa acaattcctt cctggaccca gaatattgga actttagaaa   26640
tggagatctt actgaaggca cagcctatac aaacgctgtt ggatttatgc ctaacctatc   26700
agcttatcca aaatctcacg gtaaaactgc caaagtaac attgtcagtc aagtttactt   26760
aaacggagac aaaactaaac ctgtaacact aaccattaca ctaaacggta cacaggaaac   26820
aggagacaca actccaagtg catactctat gtcattttca tgggactggt ctggccacaa   26880
ctacattaat gaaatatttg ccacatcctc ttacactttt tcatacattg cccaagaata   26940
aagaatcgtt tgtgttatgt ttcaacgtgt ttatttttca attgcagaaa atttcaagtc   27000
atttttcatt cagtagtata gccccaccac cacatagctt atacagatca ccgtacctta   27060
atcaaactca cagaaccctagtattcaacc tgccacctcc ctcccaacac acagagtaca   27120
cagtcctttc tccccggctg gccttaaaaa gcatcatatc atgggtaaca gacatattct   27180
taggtgttat attccacacg gtttcctgtc gagccaaacg ctcatcagtg atattaataa   27240
actcccgggg cagctcactt aagttcatgt cgctgtccag ctgctgagcc acaggctgct   27300
gtccaacttg cggttgctta acgggcggcg aaggagaagt ccacgcctac atgggggtag   27360
agtcataatc gtgcatcagg atagggcggt ggtgctgcag cagcgcgcga ataaactgct   27420
gccgccgccg ctccgtcctg caggaataca acatggcagt ggtctcctca gcgatgattc   27480
gcaccgcccg cagcataagg cgccttgtcc tccgggcaca gcagcgcacc ctgatctcac   27540
ttaaatcagc acagtaactg cagcacagca ccacaatatt gttcaaaatc ccacagtgca   27600
aggcgctgta tccaaagctc atggcgggga ccacagaacc cacgtggcca tcataccaca   27660
agcgcaggta gattaagtgg cgaccctca taaacacgct ggacataaac attacctctt   27720
ttggcatgtt gtaattcacc acctcccggt accatataaa cctctgatta acatggcgc   27780 catccaccac catcctaaac cagctggcca aaacctgccc gccggctata cactgcaggg   27840
aaccgggact ggaacaatga cagtggagag cccaggactc gtaaccatgg atcatcatgc   27900
tcgtcatgat atcaatgttg gcacaacaca ggcacacgtg catacacttc ctcaggatta   27960
caagctcctc ccgcgttaga accatatccc agggaacaac ccattcctga atcagcgtaa   28020
atcccacact gcagggaaga cctcgcacgt aactcacgtt gtgcattgtc aaagtgttac   28080
attcgggcag cagcggatga tcctccagta tggtagcgcg ggtttctgtc tcaaaaggag   28140
```

-continued

```
gtagacgatc cctactgtac ggagtgcgcc gagacaaccg agatcgtgtt ggtcgtagtg    28200
tcatgccaaa tggaacgccg gacgtagtca tatttcctga agcaaaacca ggtgcgggcg    28260
tgacaaacag atctgcgtct ccggtctcgc cgcttagatc gctctgtgta gtagttgtag    28320
tatatccact ctctcaaagc atccaggcgc ccctggctt cgggttctat gtaaactcct     28380
tcatgcgccg ctgccctgat aacatccacc accgcagaat aagccacacc cagccaacct    28440
acacattcgt tctgcgagtc acacacggga ggagcgggaa gagctggaag aaccatgttt    28500
tttttttat tccaaaagat tatccaaaac ctcaaaatga agatctatta agtgaacgcg      28560
ctcccctccg gtggcgtggt caaactctac agccaaagaa cagataatgg catttgtaag    28620
atgttgcaca atggcttcca aaaggcaaac ggccctcacg tccaagtgga cgtaaaggct    28680
aaacccttca gggtgaatct cctctataaa cattccagca ccttcaacca tgcccaaata    28740
attctcatct cgccaccttc tcaatatatc tctaagcaaa tcccgaatat taagtccggc    28800
cattgtaaaa atctgctcca gagcgccctc caccttcagc ctcaagcagc gaatcatgat    28860
tgcaaaaatt caggttcctc acagacctgt ataagattca aaagcggaac attaacaaaa    28920
ataccgcgat cccgtaggtc ccttcgcagg gccagctgaa cataatcgtg caggtctgca    28980
cggaccagcg cggccacttc cccgccagga accttgacaa aagaacccac actgattatg    29040
acacgcatac tcggagctat gctaaccagc gtagccccga tgtaagcttt gttgcatggg    29100
cggcgatata aaatgcaagg tgctgctcaa aaaatcaggc aaagcctcgc gcaaaaaga    29160
aagcacatcg tagtcatgct catgcagata aaggcaggta agctccggaa ccaccacaga    29220
aaaagacacc atttttctct caaacatgtc tgcgggtttc tgcataaaca caaaataaaa    29280
taacaaaaaa acatttaaac attagaagcc tgtcttacaa caggaaaaac aaccccttata   29340
agcataagac ggactacggc catgccggcg tgaccgtaaa aaaactggtc accgtgatta    29400
aaaagcacca ccgacagctc ctcggtcatg tccggagtca taatgtaaga ctcggtaaac    29460
acatcaggtt gattcatcgg tcagtgctaa aaagcgaccg aaatagcccg ggggaataca    29520
tacccgcagg cgtagagaca acattacagc ccccatagga ggtataacaa aattaatagg    29580
agagaaaaac acataaacac ctgaaaaacc ctcctgccta ggcaaaatag caccctcccg    29640
ctccagaaca acatacagcg cttcacagcg gcagcctaac agtcagcctt accagtaaaa   29700
aagaaaacct attaaaaaaa caccactcga cacggcacca gctcaatcag tcacagtgta    29760
aaaaagggcc aagtgcagag cgagtatata taggactaaa aaatgacgta acggttaaag    29820
tccacaaaaa acacccagaa aaccgcacgc gaacctacgc ccagaaacga aagccaaaaa    29880
acccacaact tcctcaaatc gtcacttccg ttttcccacg ttacgtaact tcccatttta    29940
agaaaactac aattcccaac acatacaagt tactccgccc taaaacctac gtcacccgcc    30000
ccgttcccac gccccgcgcc acgtcacaaa ctccaccccc tcattatcat attggcttca    30060
atccaaaata aggtatatta ttgatgatnn nnnttaat                            30098
```

<210> SEQ ID NO 8
<211> LENGTH: 22
<212> TYPE: DNA
<213> ORGANISM: Artificial Sequence
<220> FEATURE:
<223> OTHER INFORMATION: synthetic nucleotide - forward primer for ND
      1.1

<400> SEQUENCE: 8
gctcgctatt gtgtctctag tg                                                22

```
<210> SEQ ID NO 9
<211> LENGTH: 21
<212> TYPE: DNA
<213> ORGANISM: Artificial Sequence
<220> FEATURE:
<223> OTHER INFORMATION: synthetic nucleotide - reverse primer for ND
      1.1

<400> SEQUENCE: 9
tgtcttgggc atgagtaact g                                            21

<210> SEQ ID NO 10
<211> LENGTH: 26
<212> TYPE: DNA
<213> ORGANISM: Artificial Sequence
<220> FEATURE:
<223> OTHER INFORMATION: synhetic nucleotide - probe for ND 1.1
<220> FEATURE:
<221> NAME/KEY: misc_feature
<222> LOCATION: (1)..(1)
<223> OTHER INFORMATION: 5' labeled with 56-FAM (carboxyfluorescein)
<220> FEATURE:
<221> NAME/KEY: misc_feature
<222> LOCATION: (9)..(10)
<223> OTHER INFORMATION: ZEN (non-abbreviation) quencher incorporate
      between C (position 9) and T (position 10)
<220> FEATURE:
<221> NAME/KEY: misc_feature
<222> LOCATION: (26)..(26)
<223> OTHER INFORMATION: 3' end labeled with 3IABkFQ (Iowa black
      fluorescein quencher)

<400> SEQUENCE: 10
tcgacctgct ctgttgagtt attggc                                       26

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
gaaacgatat gggctgaata c                                            21
```